United States Patent
Kayal et al.

(10) Patent No.: US 11,590,016 B1
(45) Date of Patent: Feb. 28, 2023

(54) OSTOMY SYSTEM

(71) Applicant: Kayal Medical Products LLC, Jackson, NJ (US)

(72) Inventors: Thomas J Kayal, Jackson, NJ (US); Anastasios A Iliadis, Freehold, NJ (US); Andrew Rivera, Plainsboro, NJ (US)

(73) Assignee: Kayal Medical Products LLC, Jackson, NJ (US)

( * ) Notice: Subject to any disclaimer, the term of this patent is extended or adjusted under 35 U.S.C. 154(b) by 383 days.

(21) Appl. No.: 16/774,406

(22) Filed: Jan. 28, 2020

(51) Int. Cl.
*A61F 5/448* (2006.01)
*A61F 5/443* (2006.01)
*A61F 5/44* (2006.01)

(52) U.S. Cl.
CPC .............. *A61F 5/448* (2013.01); *A61F 5/443* (2013.01)

(58) Field of Classification Search
CPC ............. A61F 5/448; A61F 5/443; A61F 5/44
See application file for complete search history.

(56) References Cited

U.S. PATENT DOCUMENTS

| | | | |
|---|---|---|---|
| 2,048,392 A | 7/1936 | Koenig | |
| 2,496,175 A | 1/1950 | Perry | |
| 2,505,664 A | 4/1950 | Edwards | |
| 2,549,649 A | 4/1951 | Van Hove | |
| 2,595,934 A | 5/1952 | Ginsburg | |
| 2,638,898 A | 5/1953 | Perry | |
| 2,684,675 A | 7/1954 | Perry | |
| 2,721,553 A | 10/1955 | Perry | |
| 2,796,063 A * | 6/1957 | Smelser | A61F 5/448 604/342 |
| 3,089,493 A * | 5/1963 | Galindo | A61F 5/445 604/344 |
| 3,398,744 A * | 8/1968 | Hooper | A61F 5/445 604/340 |
| 3,523,534 A | 8/1970 | Nolan | |
| 3,690,320 A | 9/1972 | Riely | |
| 3,736,934 A | 6/1973 | Hennessy | |
| 3,827,435 A | 8/1974 | Marsan | |
| 3,865,109 A * | 2/1975 | Elmore | A61F 5/441 604/339 |
| 3,970,085 A | 7/1976 | Mersan | |
| 4,268,286 A | 5/1981 | Steer et al. | |
| 4,294,252 A * | 10/1981 | Einset | A61F 5/448 604/345 |

(Continued)

FOREIGN PATENT DOCUMENTS

EP 0598625 B1 1/1999

*Primary Examiner* — Guy K Townsend

(57) ABSTRACT

In an embodiment of the invention, an ostomy system may comprise a stationary ring and a movable ring, hingedly connected to each other. One of the rings may include a deformable lip usable in creating a seal. The inner pouch may comprise a film material and a sealing member such as a gasket that is grippable between the two rings. The sealing member may be stiff when dry but may quickly become soft upon immersion in water, and may comprise paper material. The outer pouch may comprise a blister or pleat that is flexible and deformable between a compact position and an extended position. The outer pouch may comprise a storage region capable of containing at least one unused inner pouch. The system may comprise a wafer and an outer pouch and an inner pouch as separately replaceable parts.

6 Claims, 38 Drawing Sheets

(56) References Cited

U.S. PATENT DOCUMENTS

| | | | |
|---|---|---|---|
| 4,359,051 A * | 11/1982 | Oczkowski | A61F 5/448 604/339 |
| 4,411,659 A | 10/1983 | Jensen et al. | |
| 4,419,100 A | 12/1983 | Alexander | |
| 4,460,363 A | 7/1984 | Steer et al. | |
| 4,465,486 A | 8/1984 | Hill | |
| 4,561,858 A | 12/1985 | Allen, Jr. et al. | |
| 4,610,676 A | 9/1986 | Schneider et al. | |
| 4,685,990 A | 8/1987 | Ferguson | |
| 4,701,169 A | 10/1987 | Steer et al. | |
| 4,784,656 A * | 11/1988 | Christian | A61F 5/441 604/355 |
| 4,816,027 A | 3/1989 | Gilchrist et al. | |
| 4,826,495 A | 5/1989 | Petersen | |
| 4,828,553 A * | 5/1989 | Nielsen | A61F 5/448 604/339 |
| 4,834,730 A | 5/1989 | Holtermann et al. | |
| 4,846,798 A | 7/1989 | Holtermann et al. | |
| 4,846,820 A | 7/1989 | Jensen | |
| 4,872,869 A | 10/1989 | Johns | |
| 4,917,689 A | 4/1990 | Coombes | |
| 4,917,691 A * | 4/1990 | Briggs | A61F 5/448 604/339 |
| 5,125,133 A | 6/1992 | Morrison | |
| 5,135,519 A | 8/1992 | Helmer | |
| 5,139,492 A | 8/1992 | Leise, Jr. et al. | |
| 5,163,930 A | 11/1992 | Blum | |
| 5,185,008 A * | 2/1993 | Lavender | A61F 5/448 604/338 |
| 5,209,744 A | 5/1993 | Abe et al. | |
| 5,312,381 A | 5/1994 | Brooks | |
| 5,312,382 A | 5/1994 | Metz | |
| 5,322,523 A * | 6/1994 | Olsen | A61F 5/448 604/338 |
| 5,364,378 A * | 11/1994 | Denard | A61F 5/445 604/335 |
| 5,423,782 A | 6/1995 | Wolrich | |
| 5,429,625 A | 7/1995 | Holmberg | |
| 5,429,626 A | 7/1995 | Fenton | |
| 5,496,296 A | 3/1996 | Holmberg | |
| 5,501,677 A * | 3/1996 | Jensen | A61F 5/448 604/338 |
| 5,520,670 A | 5/1996 | Blum | |
| 5,617,616 A | 4/1997 | Cutts, Sr. | |
| 5,722,965 A | 3/1998 | Kuczynski | |
| 5,833,915 A | 11/1998 | Shah | |
| 5,843,053 A * | 12/1998 | Steer | A61F 5/448 604/338 |
| 5,865,819 A * | 2/1999 | Cisko, Jr. | A61F 5/445 604/338 |
| 5,938,647 A | 8/1999 | Smith | |
| 5,947,941 A | 9/1999 | Leise, Jr. et al. | |
| 5,968,023 A | 10/1999 | Olsen | |
| 6,409,710 B1 | 6/2002 | Holtermann | |
| 6,485,476 B1 | 11/2002 | von Dyck et al. | |
| 6,537,261 B1 * | 3/2003 | Steer | A61F 5/448 604/342 |
| 6,544,241 B2 | 4/2003 | Morton | |
| 6,673,056 B2 | 1/2004 | Metz et al. | |
| 6,702,794 B2 | 3/2004 | Blum et al. | |
| 6,709,422 B2 | 3/2004 | Hessel et al. | |
| 6,723,079 B2 | 4/2004 | Cline | |
| 6,902,551 B2 | 6/2005 | Hansen et al. | |
| 7,087,042 B2 | 8/2006 | Montgomery | |
| 7,179,245 B2 | 2/2007 | Glori | |
| 7,422,578 B2 | 9/2008 | Shan et al. | |
| 7,470,263 B2 | 12/2008 | Strobech | |
| 7,556,707 B2 | 7/2009 | Giori | |
| 7,879,016 B2 | 2/2011 | Mandzij et al. | |
| 7,947,025 B2 | 5/2011 | Buglino et al. | |
| 8,096,980 B2 | 1/2012 | Cline | |
| 8,100,875 B2 | 1/2012 | Cline et al. | |
| 8,105,298 B2 * | 1/2012 | Mullejans | A61F 5/448 604/338 |
| 8,118,797 B2 | 2/2012 | Giori et al. | |
| 8,142,406 B2 | 3/2012 | Blum | |
| 8,211,072 B2 | 7/2012 | Smith et al. | |
| 8,328,779 B2 | 12/2012 | Fenton | |
| 8,343,121 B2 * | 1/2013 | Cramer | A61F 5/445 604/344 |
| 8,574,207 B2 | 11/2013 | Lundholt et al. | |
| 8,690,848 B2 | 4/2014 | Cason | |
| 8,740,832 B2 * | 6/2014 | Smith | A61F 5/445 604/8 |
| 9,033,944 B2 | 5/2015 | Wolrich | |
| 9,233,019 B2 | 1/2016 | Lykke et al. | |
| 9,333,110 B2 | 5/2016 | March et al. | |
| 9,345,612 B2 | 5/2016 | Hanuka et al. | |
| 9,452,079 B2 | 9/2016 | Lykke et al. | |
| 9,498,372 B2 * | 11/2016 | Fattman | A61F 5/448 |
| 9,532,609 B2 * | 1/2017 | Stevenson | A41D 13/02 |
| 9,539,137 B2 | 1/2017 | Smith | |
| 9,545,329 B2 | 1/2017 | Salama | |
| 9,629,779 B2 | 4/2017 | Grum-Schwensen et al. | |
| 9,795,501 B2 * | 10/2017 | Nassopoulos | A61F 5/445 |
| 10,022,260 B2 * | 7/2018 | Richmann | A61F 5/4407 |
| 10,537,462 B1 | 1/2020 | Hatchett | |
| 11,154,415 B2 * | 10/2021 | Johnson | A61F 5/4404 |
| 2002/0010444 A1 | 1/2002 | Wiltshire et al. | |
| 2002/0114539 A1 | 8/2002 | Strevey et al. | |
| 2003/0023210 A1 | 1/2003 | Bedard et al. | |
| 2004/0059306 A1 * | 3/2004 | Tsai | A61F 5/4404 604/332 |
| 2004/0184876 A1 * | 9/2004 | Hessel | A61F 5/448 403/326 |
| 2008/0033380 A1 | 2/2008 | Andersen | |
| 2010/0114045 A1 * | 5/2010 | Cramer | A61F 5/445 604/338 |
| 2010/0241093 A1 | 9/2010 | Hooper | |
| 2011/0166539 A1 | 7/2011 | Eakin | |
| 2011/0238024 A1 * | 9/2011 | Smith | A61F 5/445 604/336 |
| 2013/0261576 A1 | 10/2013 | Strobech et al. | |

\* cited by examiner

100

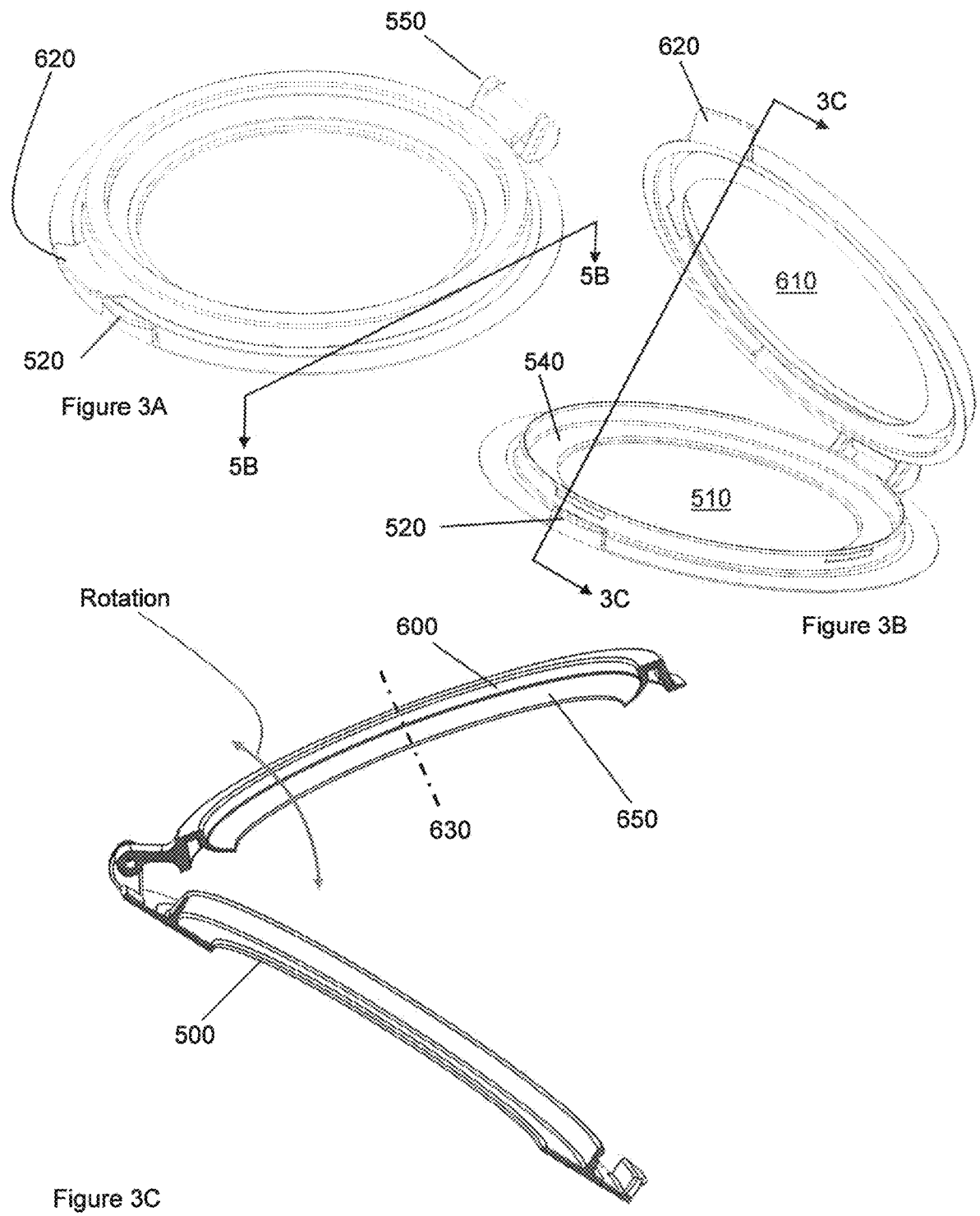

Partially open configuration

Fully open configuration

In the process of being closed

Interference between lip 650 (shown undeflected) and gasket 200

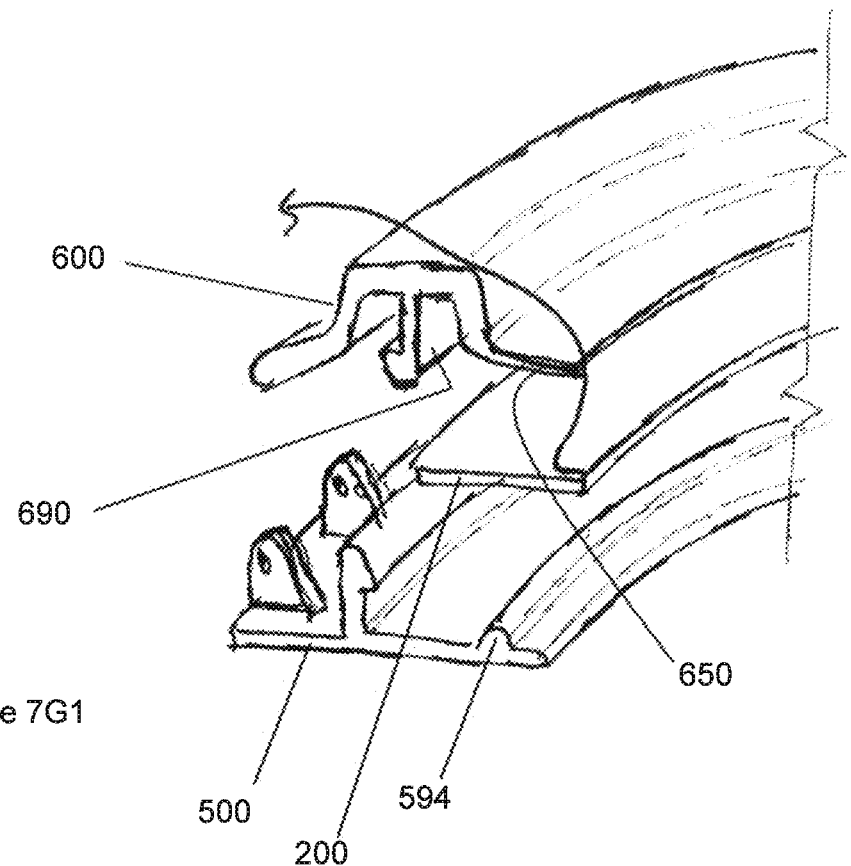
Figure 7G1
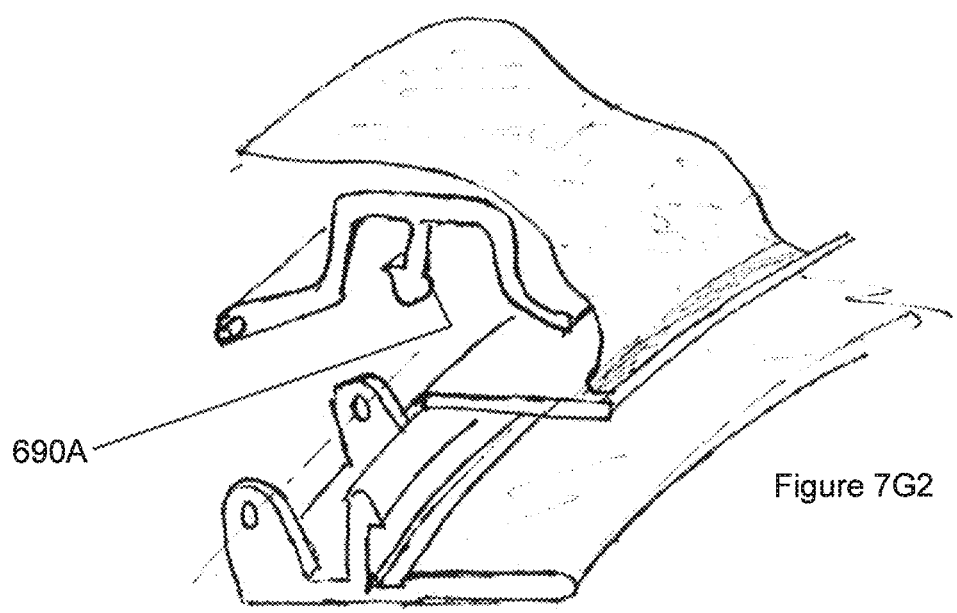
Figure 7G2

Figure 8A
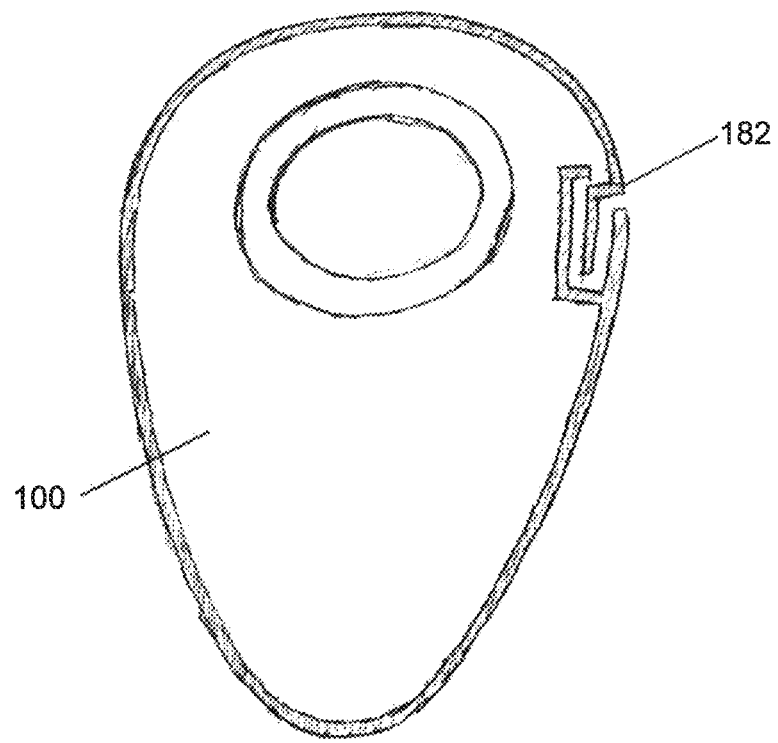
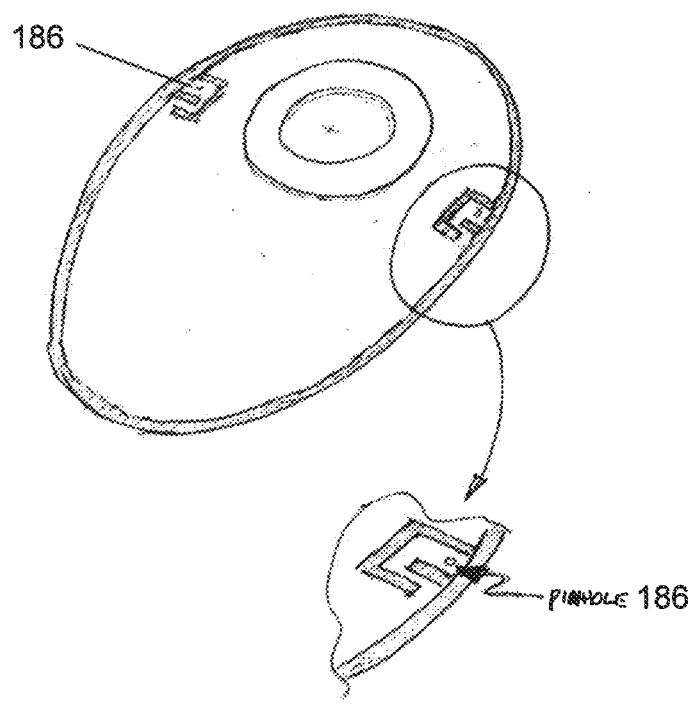
Figure 8B

Figure 8C
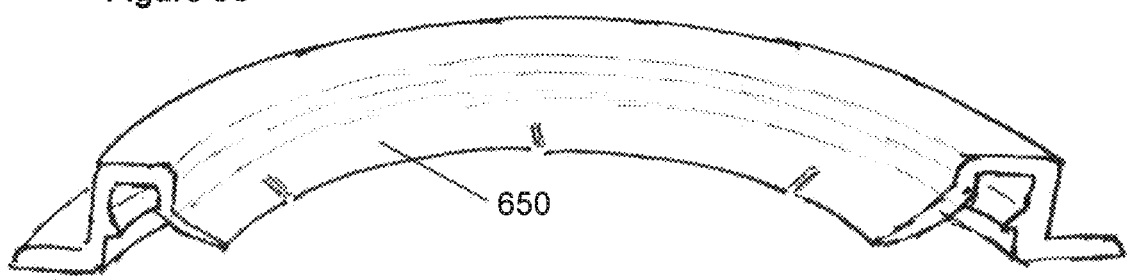
Figure 8D
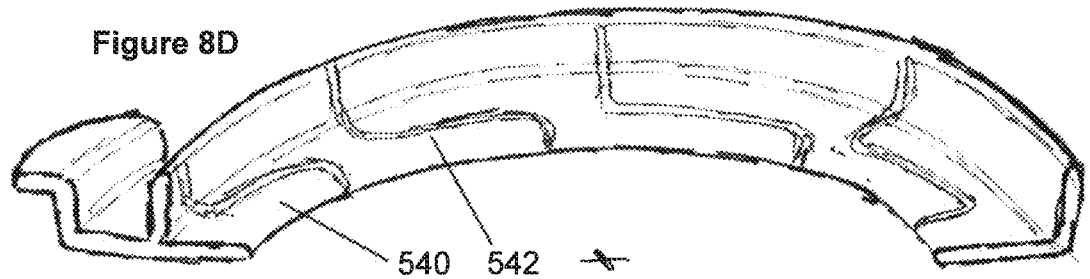
Figure 8E
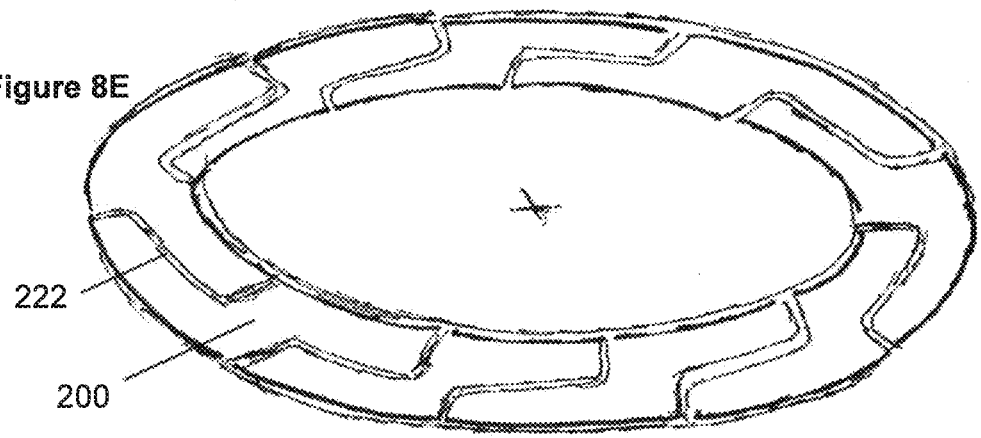
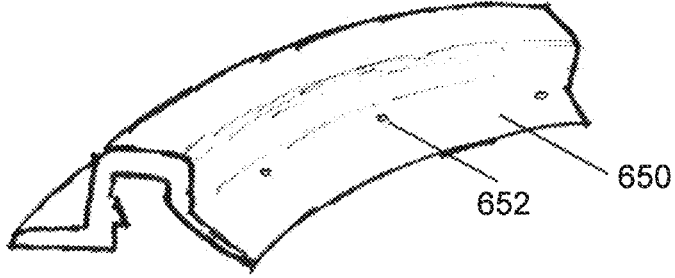
Figure 8F

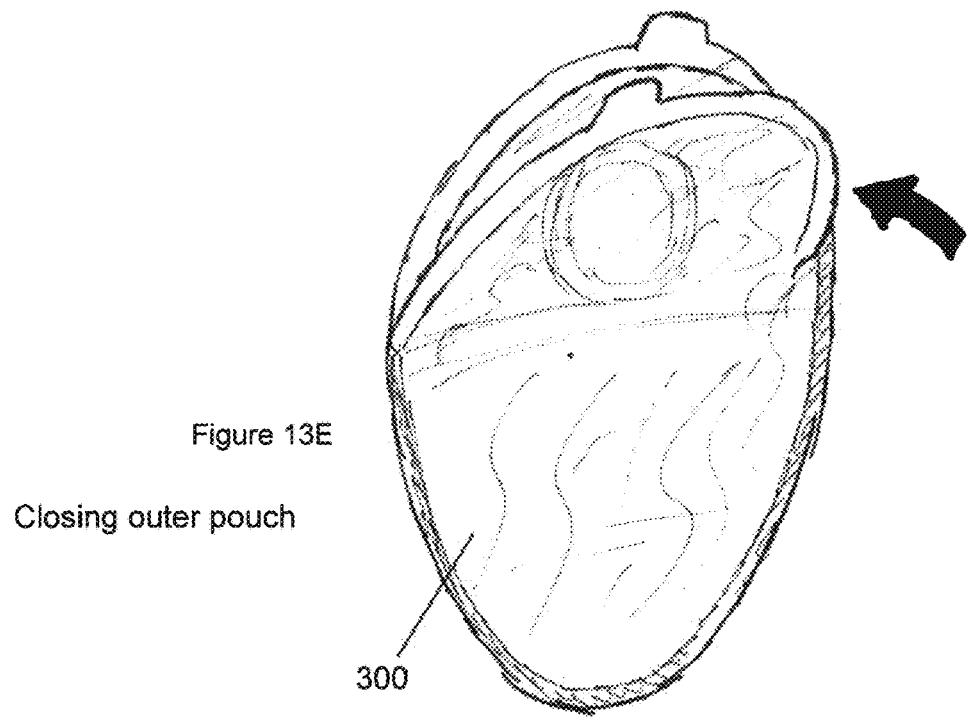
Figure 13E
Closing outer pouch
300
Figure 13F
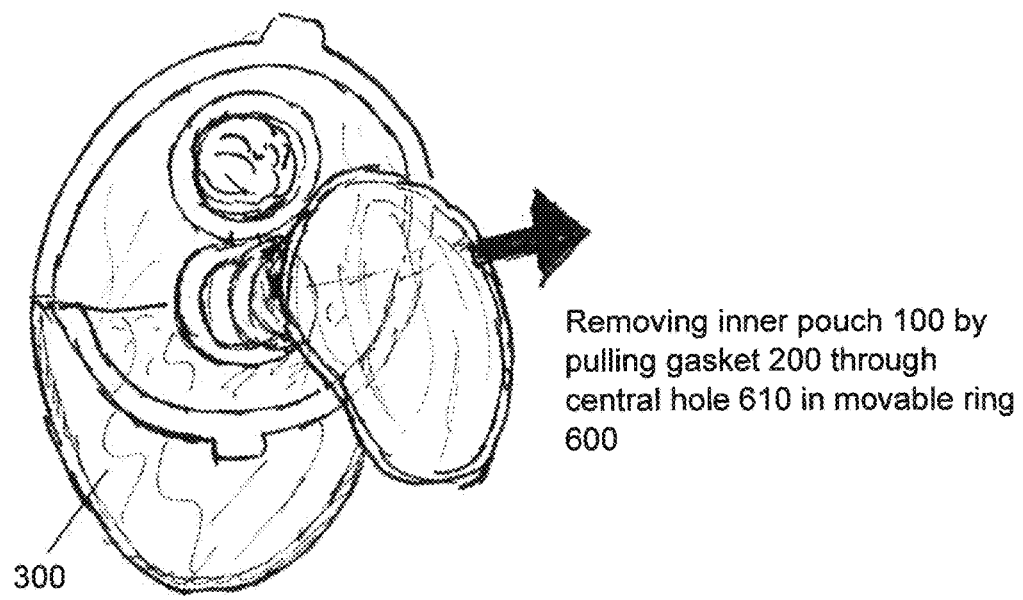
Removing inner pouch 100 by pulling gasket 200 through central hole 610 in movable ring 600
300

OSTOMY SYSTEM

FIELD OF THE INVENTION

Embodiments of the invention pertain to systems for use by ostomy patients.

BACKGROUND OF THE INVENTION

Various products currently exist to serve the needs of ostomy patients. However, all of them have shortcomings in terms of convenience, ease of use, protruding profile, etc. In general, it is desired that removing a pouch from the appliance and attaching a new pouch to the appliance be as convenient as possible.

In the case of conventional one-piece ostomy pouches that comprise the pouch and wafer in the same appliance, a shortcoming includes the need for frequent removal of the ostomy adhesive wafer from the peristomal skin once or twice daily. In the case of conventional two-piece ostomy appliances, which comprise a pouch that is removably attached to an ostomy wafer, they suffer from the relatively high cost of the pouches which include features such as multi-layer odor barrier film, molded plastic coupling components, nonwoven comfort panels, and flatus filters. Furthermore, such pouches from two-piece ostomy devices must be disposed of in household or public trash containers because the components are not degradable.

SUMMARY OF THE INVENTION

An embodiment of the invention can comprise an ostomy system, comprising: an inner pouch, the inner pouch comprising a film material defining an interior volume and comprising a sealing member, different from the film material in either its material composition or its thickness dimension or both, said sealing member being connected to or integral with the film material, the sealing member having a hole therethrough connecting with the interior volume, the inner pouch being suitable to receive waste matter from the patient; a stationary ring; and a movable ring hingedly connected to the stationary ring, the movable ring being movable between a closed configuration and an open configuration, wherein in the closed configuration the movable ring and the stationary ring cooperate suitably to grasp the sealing member between the movable ring and the stationary ring suitably to form a desired seal, without grasping the film material between the movable ring and the stationary ring in the absence of the sealing member.

An embodiment of the invention can comprise an ostomy system, comprising: an appliance that is suitable to attach or adhere to a body of an ostomy patient; an inner pouch assembly, disposed within or connected to the appliance, comprising an inner pouch, the inner pouch being suitable to receive waste matter from the patient and contain the waste matter within the inner pouch, wherein the appliance comprises a stationary ring and a movable ring, the stationary ring and the movable ring being hingedly connected to each other, the movable ring being movable between a closed configuration and an open configuration, wherein the movable ring comprises a ring structure that extends generally around a perimeter of the movable ring and comprises a deformable lip connected to or integral with the ring structure, wherein the lip and the movable ring and the stationary ring and the inner pouch assembly are disposed relative to each other such that when the movable ring and the stationary ring are in the closed configuration, a portion of the inner pouch assembly is squeezed between the lip and the stationary ring so as to create a desired seal involving the inner pouch assembly.

An embodiment of the invention can comprise an ostomy system, comprising: an appliance that is suitable to attach or adhere to a body of an ostomy patient; an inner pouch assembly, disposed within or connected to the appliance, comprising an inner pouch, the inner pouch being suitable to receive waste matter from the patient and contain the waste matter within the inner pouch, wherein the appliance comprises a stationary ring and a movable ring, the stationary ring and the movable ring being hingedly connected to each other, the movable ring being movable between a closed configuration and an open configuration, wherein the stationary ring comprises a ring structure that extends generally around a perimeter of the stationary ring and comprises a deformable lip connected to or integral with the ring structure, wherein the lip and the movable ring and the stationary ring and the inner pouch assembly are disposed relative to each other such that when the movable ring and the stationary ring are in the closed configuration, a portion of the inner pouch assembly is squeezed between the lip and the movable ring so as to create a desired seal involving the inner pouch assembly.

An embodiment of the invention can comprise an ostomy system, comprising: an appliance that is suitable to attach or adhere to a body of an ostomy patient; an inner pouch within the appliance, the inner pouch being suitable to receive waste matter from the patient and contain the waste matter within the inner pouch, wherein the inner pouch comprises an inner pouch proximal layer and an inner pouch distal layer joined to each other, wherein the inner pouch comprises a gasket connected to the inner pouch proximal layer and shares a common hole with the inner pouch proximal layer, wherein the gasket defines a closed ring shape lying in a plane and the gasket has a bending stiffness for the out-of-plane bending, wherein, in a dry state, the bending stiffness of the gasket for the out-of-plane bending that is greater than a stiffness of the inner pouch proximal layer, wherein the gasket, in a dry state, when grasped at an edge in a horizontally cantilevered configuration bearing its own weight, the gasket deflects by less than 10% of a cantilever distance, and wherein the gasket, after having been immersed in water for at least 5 seconds, or at least 10 seconds, when grasped at the edge in the horizontally cantilevered configuration bearing its own weight including weight of any water absorbed into the gasket, deflects by more than 10% of the cantilever distance.

An embodiment of the invention can comprise an ostomy system, comprising: an appliance that is suitable to attach or adhere to a body of an ostomy patient, the appliance comprising an outer pouch and an inner pouch; wherein the inner pouch is disposed suitably to receive waste matter from the patient and contain the waste matter within the inner pouch, wherein the outer pouch generally surrounds the inner pouch, wherein the outer pouch comprises an outer pouch proximal layer and an outer pouch distal layer opposed to the outer pouch proximal layer, and wherein the outer pouch distal layer comprises a deformable surface that is larger than a corresponding surface on the outer pouch proximal layer, wherein the deformable surface is flexible and deformable between a compact position and an extended position, and when in the extended position has a surface length that is greater than a surface length of a corresponding region on the outer pouch proximal layer.

An embodiment of the invention can comprise an ostomy system, comprising: an appliance that is suitable to attach or adhere to a body of an ostomy patient, the appliance comprising an outer pouch and an inner pouch the inner pouch being generally surrounded by the outer pouch; wherein the inner pouch is disposed suitably to receive waste matter from the patient and contain the waste matter within the inner pouch, wherein the outer pouch comprises a storage region comprising an additional layer connected to the outer pouch, the storage region being dimensioned appropriately to contain at least one unused inner pouch.

An embodiment of the invention can comprise an ostomy system, comprising: an inner pouch, the inner pouch comprising a film material defining an interior volume and comprising a sealing member, different from the film material, connected to or integral with the film material, the film material and the sealing member having a common hole therethrough suitable to receive waste matter from the patient such that the waste matter can be contained within the interior volume; a stationary ring; and a movable ring hingedly connected to the stationary ring, the movable ring being movable between a closed configuration and an open configuration, wherein in the closed configuration the movable ring and the stationary ring cooperate suitably to grasp the sealing member between the movable ring and the stationary ring suitably to form a desired seal, wherein in the closed configuration the movable ring and the stationary ring engage each other with a latch, wherein the stationary ring and the movable ring comprise a material having a Shore durometer property of Shore A50 or softer, and wherein the latch extends around at least 270 degrees of circumference of the stationary ring and the movable ring.

An embodiment of the invention can comprise an ostomy system, the system comprising: a wafer assembly attachable to a patient's skin, the wafer assembly comprising a wafer coupling; and an appliance comprising an appliance coupling engageable with the wafer coupling, the appliance further comprising a gripping mechanism that, while the appliance coupling is engaged with the wafer coupling, has a closed configuration in which the appliance grips an inner pouch and an open configuration in which the inner pouch is not gripped.

An embodiment of the invention can comprise a method of installing an inner pouch in an ostomy appliance, the method comprising: providing an appliance comprising an outer pouch, a stationary ring and a movable ring hingedly connected to the stationary ring, the stationary ring and the movable ring having respective central openings therethrough, the movable ring being movable between a closed configuration and an open configuration, the outer pouch having a reclosable opening; providing an inner pouch, the inner pouch comprising a sealing member and film material connected to or integral with the sealing member, at least a portion of the inner pouch being suitable to pass through the central opening of the movable ring; with the movable ring being in the open configuration, passing a portion of the inner pouch through the central opening in the movable ring; moving the movable ring to the closed configuration such that the sealing member is grasped between the movable ring and the stationary ring; and closing the reclosable opening in the outer pouch.

BRIEF DESCRIPTION OF THE ILLUSTRATIONS

Embodiments of the invention are further described in the following illustrations.

FIG. 1A is a three-dimensional view, somewhat from the front of an appliance of an embodiment of the invention. FIG. 1B is a three-dimensional view, somewhat from the rear, of an appliance of an embodiment of the invention. FIG. 1C is a three-dimensional view showing details of the purse handle closure mechanism. FIGS. 1D and 1E show a purse handle having a tab that is hinged or bendable. FIG. 1F shows a closure having a flap that overlaps with another part of the appliance and has an overlap margin having a peelable adhesive. FIG. 1G shows the flap in isolation.

FIG. 2A illustrates a three-dimensional view of an inner pouch of an embodiment of the invention, viewing the distal side of the inner pouch (the side away from the body of the wearer), and viewing the proximal side of the inner pouch (the side closest to the body of the wearer).

FIG. 2B is a cross-section of the inner pouch and its gasket. FIG. 2C is an exploded view of the components making up the inner pouch. FIG. 2D is a close-up cross-section of the inner pouch and its gasket, showing the inner pouch joined to the gasket only at the inner radius of the gasket. FIG. 2E is a close-up cross-section of the inner pouch and its gasket, showing the inner pouch joined to the gasket at a portion of a flat surface of the gasket. FIG. 2F is a close-up cross-section of the inner pouch and its gasket, showing the inner pouch joined to the gasket at almost all of a flat surface of the gasket. FIG. 2G is similar to FIG. 2F but with the attachment to an opposite side of the gasket. FIG. 2H illustrates an inner pouch having a sealing member that resembles an O-ring. FIG. 2I illustrates a gasket that is substantially undeflected. FIG. 2J illustrates some deflection of the gasket. FIG. 2K illustrates a still greater deflection of the gasket. FIG. 2L illustrates dimensions of an inner pouch in regard to the ability of the inner pouch to be flushed in a toilet.

FIG. 3A, 3B, 3C illustrates a stationary ring and a movable ring hingedly connected to each other. FIG. 3D illustrates a hinge that is a snap-together hinge. FIG. 3E illustrates a hinge that is swaged together. FIG. 3F illustrates a hinge that has an angular stop or limit of rotation. FIG. 3G shows a hinge that contains a detent as part of the hinge.

FIG. 4 illustrates finger-operable features of the stationary ring and the movable ring.

FIG. 5A illustrates latching features of the stationary ring and the movable ring. FIG. 5A is a cross-section of the stationary ring and movable ring, without an inner pouch being present. FIG. 5B is a three-dimensional view of stationary ring and the movable ring showing the locations of latches in an embodiment. FIG. 5C is a cross-section of another latch design. FIG. 5D is a cross-section of another latch design. FIG. 5E is a cross-section of yet another latch design. FIGS. 5F, 5G and 5H are sketches of designs in which the latching is continuous around the stationary ring and the movable ring.

FIG. 6A shows, in cross-section, a relationship between a gasket and a lip and other components. FIG. 6B is a close-up of FIG. 6A. FIGS. 6C-6D illustrate that there could be a flexible lip on the stationary ring.

FIG. 7A shows, in the open configuration, an inner pouch located within the movable ring as determined by the relation of the neck of the inner pouch with respect to the movable ring, in the open configuration. FIG. 7B shows, in cross-section, a situation in which the gasket outer surface is not in contact with a feature of the stationary ring. FIG. 7C shows, in cross-section, a possible location of the gasket in the closed configuration, such that the gasket outer surface is in continuous contact with a feature of the stationary ring. FIG. 7D shows a similar situation in which the gasket outer surface is in contact with isolated features (ribs) of the stationary ring. FIG. 7E shows an assembly in which the movable ring has a locating wall for locating the gasket. FIG. 7F shows a similar situation further including a groove in the stationary ring so as to provide a receiving space for the locating wall. FIGS. 7G1 and 7G2 show a partially disassembled assembly including a circumferential bump. FIG. 7H shows an assembly in which the movable ring has intermittent gasket locators that are localized ribs, and the wall in the stationary ring has interruptions suitable to accommodate the ribs or gasket locator features. FIG. 7I shows an assembly (exploded) in which the movable ring intermittent gasket locators are an interrupted wall, and the wall in the stationary ring has interruptions suitable to accommodate the gasket locator features. FIG. 7J shows an assembly similar to FIGS. 7G and 7H but with a living hinge. FIG. 7K is an illustration about hardnesses of polymeric materials and the scales for such measurements. FIG. 7L is a schematic illustration, in an unengaged situation, of a stationary ring and a movable ring in which the movable ring has a natural shape that is somewhat curved out of a planar shape. FIG. 7M is a similar schematic illustration of the two rings in an engaged situation, as a result of the movable ring undergoing bending.

FIG. 8A illustrates that a gas exit or leakage path can be provided by a slight interruption in the joint around the perimeter of the inner pouch. FIG. 8B illustrates an exit hole in the membrane material of the inner pouch. FIG. 8C is an illustration showing lip interrupted in isolated places so as to avoid exerting pressure on gasket at those places. FIG. 8D illustrates the seating surface of the stationary ring containing small grooves for passage of gas. FIG. 8E shows grooves pressed or embedded into surface of the gasket. FIG. 8F shows pinholes in the lip for passage of gas.

Figure 12A:
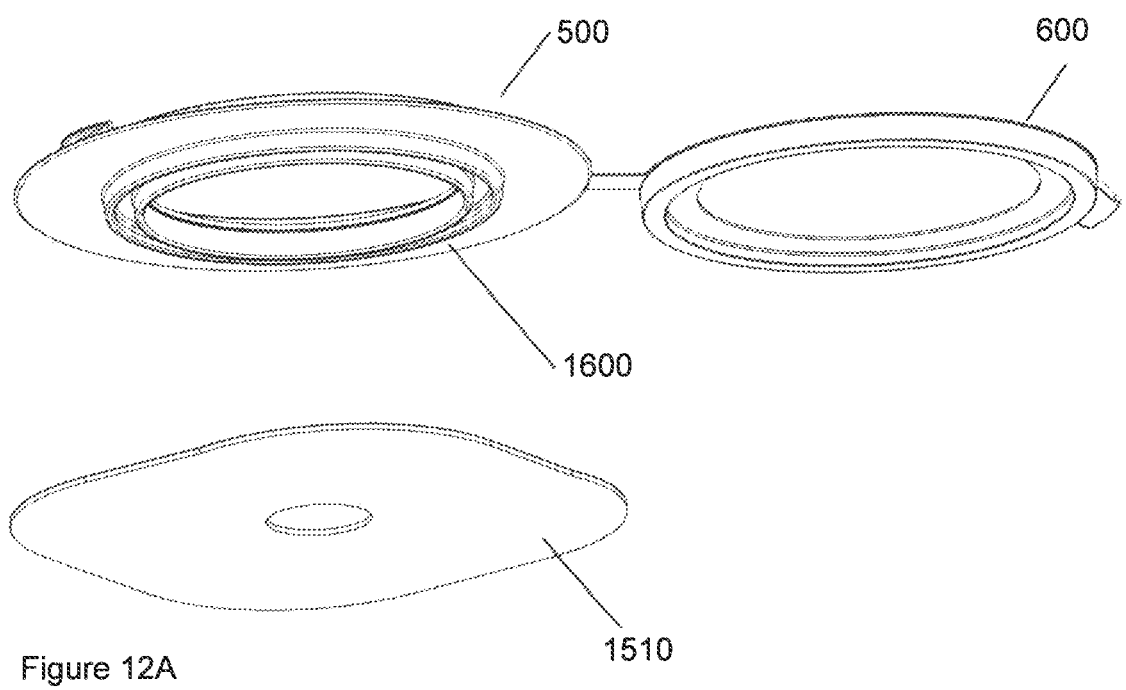
Figure 12B:
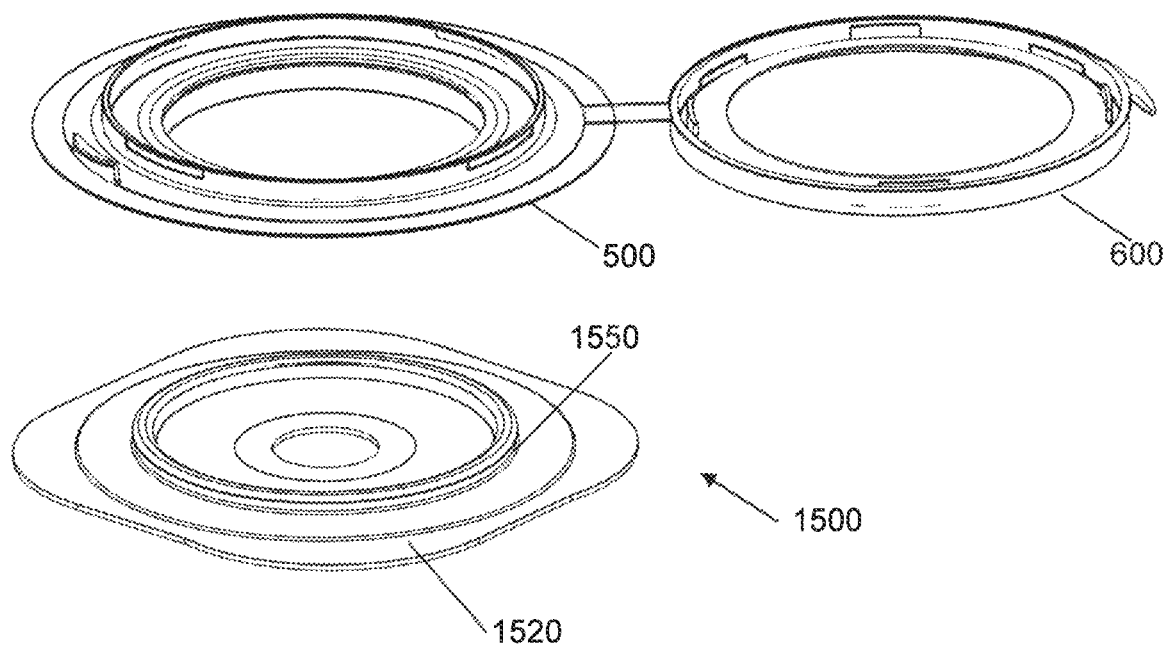
Figure 12C:
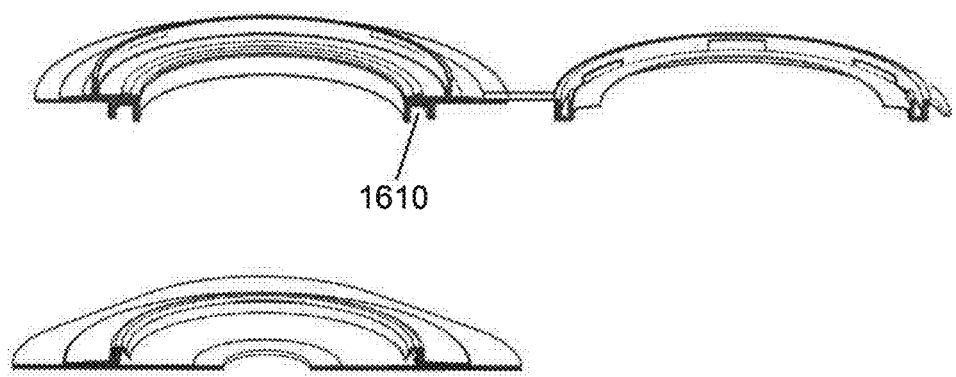
Figure 12D:
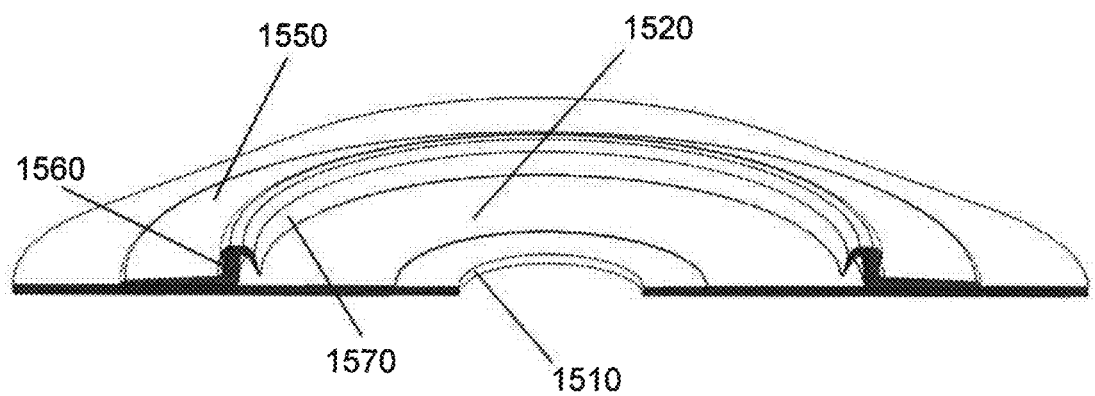
Figure 12E:
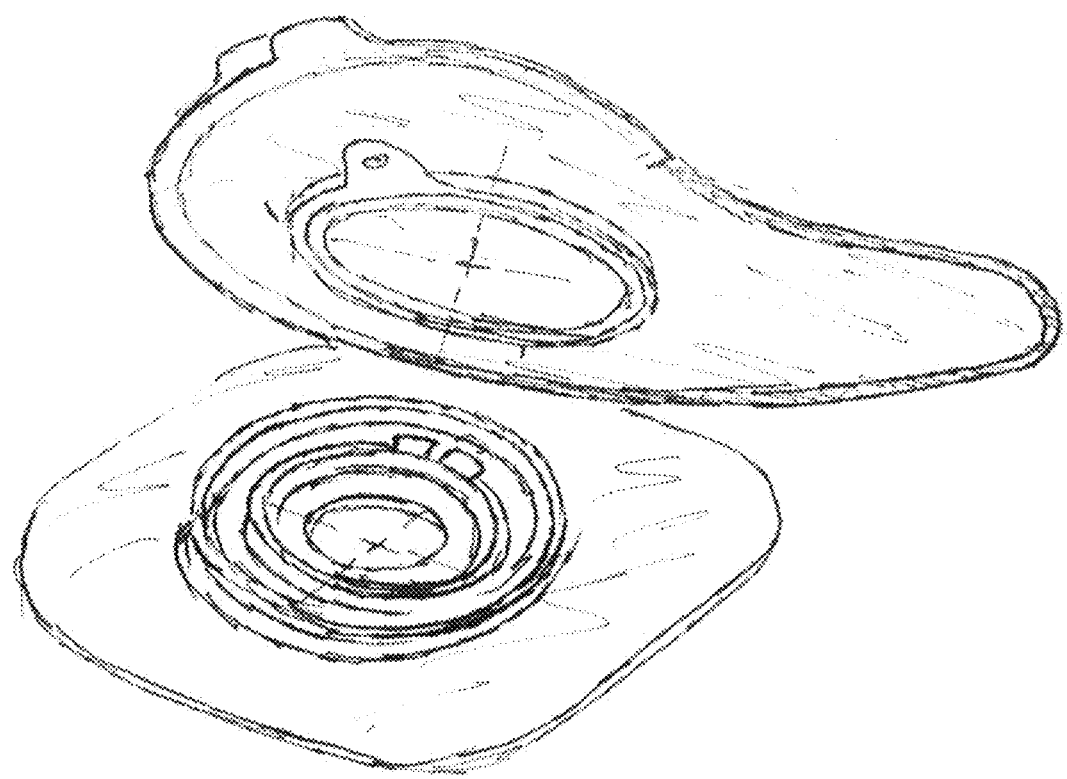

FIG. 12A, for an embodiment that has a wafer assembly and a remainder of an appliance, is an exploded view, from the body-facing side, of the wafer assembly and the combined stationary ring and movable ring. FIG. 12B is a view similar to FIG. 12A but from a vantage point away from the user's body. FIG. 12C is a cross-section of FIG. 12B. FIG. 12D is a close-up of the wafer assembly in cross-section. FIG. 12E is a sketch of the wafer assembly and the appliance about to be assembled to each other.

Figure 13A:
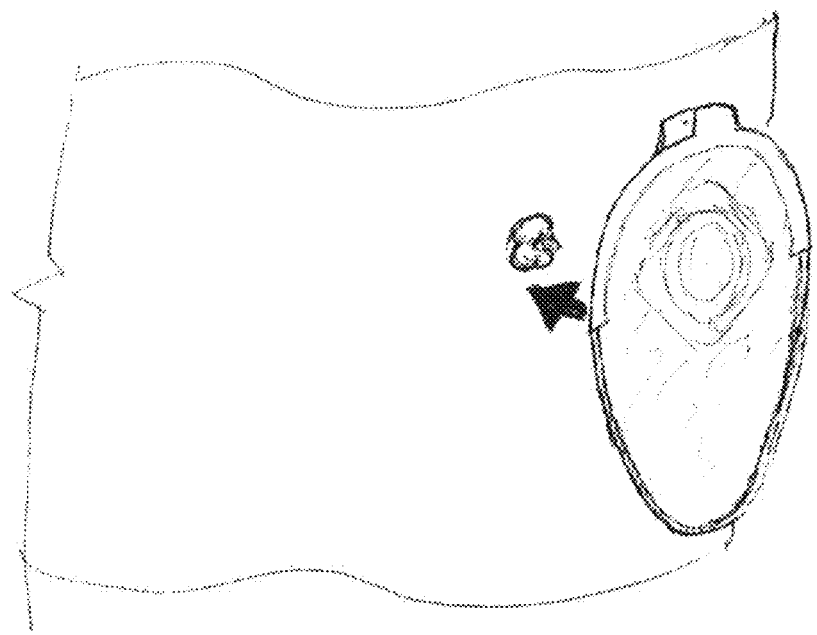
Figure 13B:
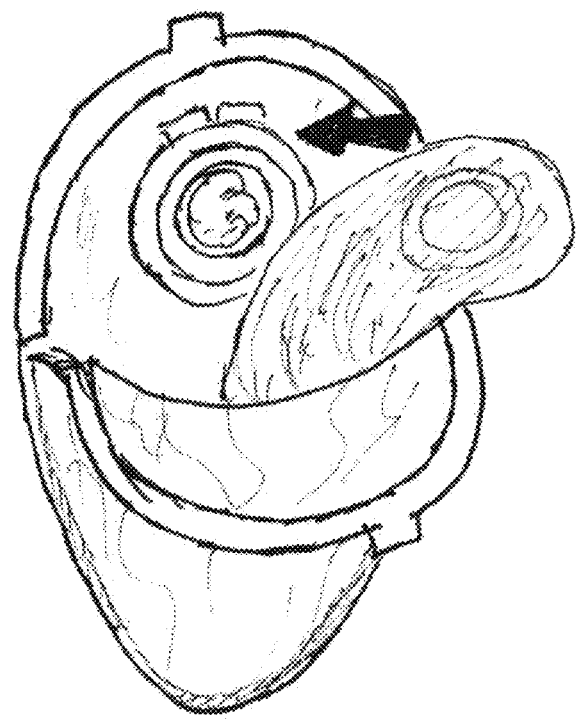
Figure 13C:
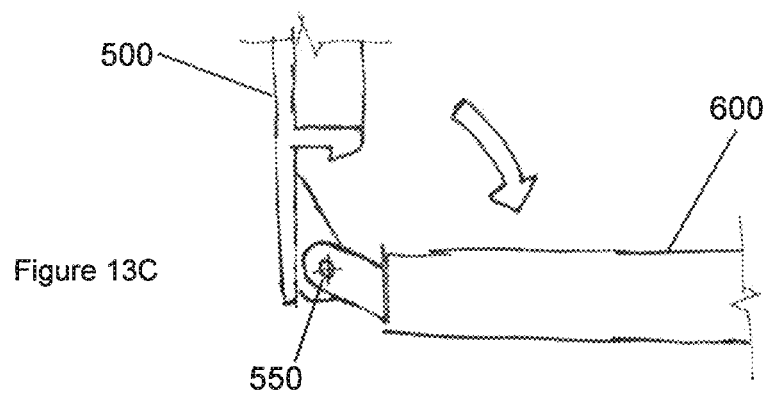
Figure 13D:
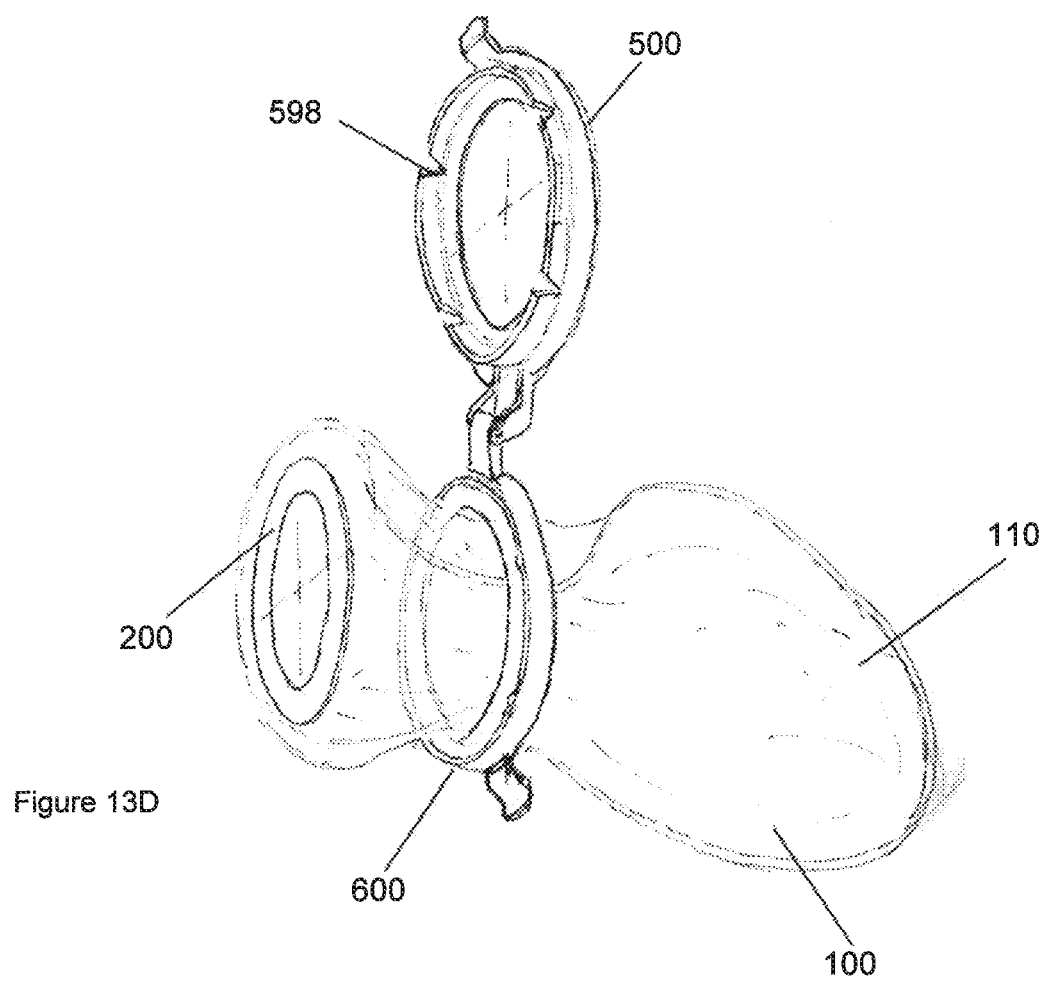

FIG. 13A shows the process of attachment of the outer pouch to patient's body. FIG. 13B shows insertion of the inner pouch into the outer pouch. FIG. 13C shows a detail of the hinge and its angular limitation. FIG. 13D shows insertion of the inner pouch into the movable ring. FIG. 13E shows closure of the outer pouch. FIG. 13F shows removing the inner pouch by pulling the gasket through the central hole in the movable ring.

DETAILED DESCRIPTION OF THE INVENTION

Herein, the terms proximal and distal are used to refer to anatomical relationships. Proximal is used herein to mean closest to the body of the user or patient who is wearing the ostomy appliance. Distal refers to a position further away from the body of the user or patient.

Herein, "sealing member" is used to refer to a sealing-involved component that is attached to or integral with the inner pouch. "Gasket" is used to refer to a sealing member that is at least somewhat flat in one of its dimensions. A gasket may have a central hole therethrough and may be generally annular in shape. A gasket could be made of a single material or of multiple materials and could have an interpenetrating or partially interpenetrating material in addition to a main material of which the gasket is made. "Wafer" is used to refer to a layer or component that, during use, is located in contact with the patient's skin. The wafer may have adhesive properties and may attach the appliance to the patient's skin. A wafer may have a central hole therethrough and may be generally annular in shape, or its external perimeter may be generally any desired shape. So-called one-piece and two-piece wafers are possible.

Appliance

Figures 1A, 1B:
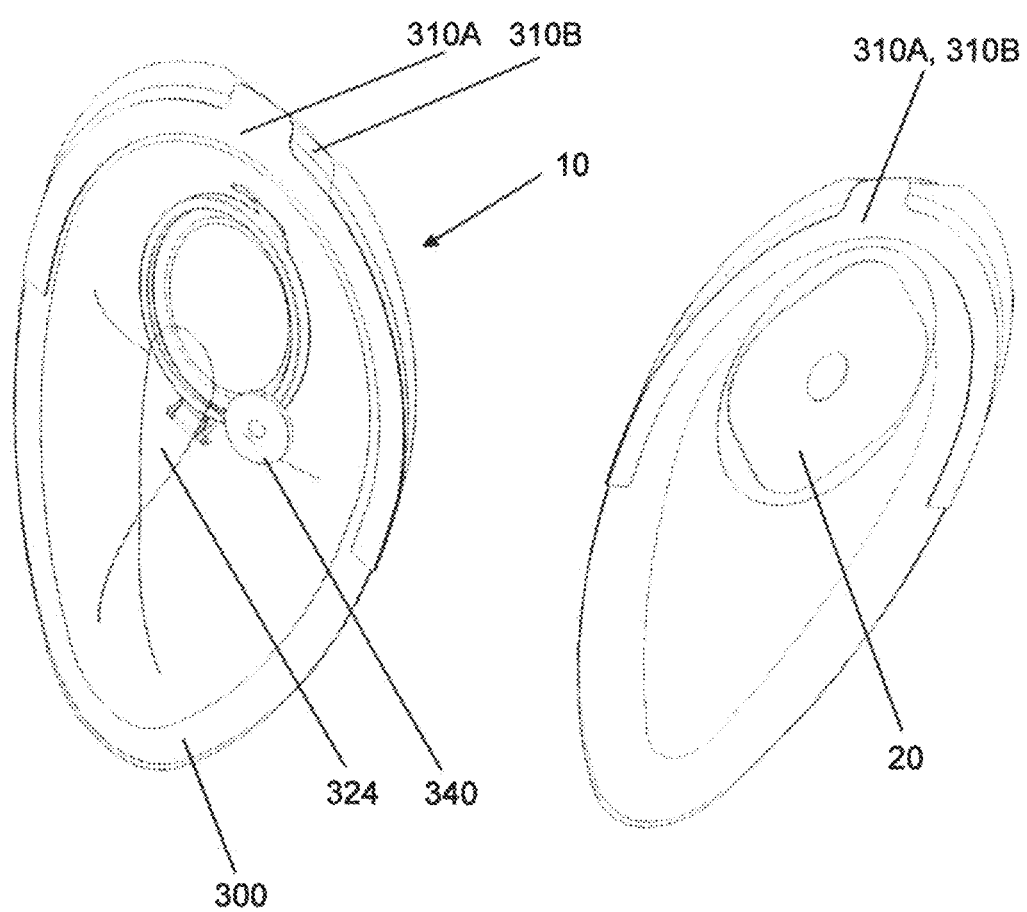

Referring now to FIGS. 1A-1B, in an embodiment of the invention, there may be provided an appliance 10, which may be attachable to a patient's body. The appliance 10 or a component thereof may be suitable to be attached to the abdominal skin of the patient surrounding the patient's stoma. The appliance 10 may be such that the appliance 10 can be worn for moderately long periods of time such as several days, but also can be removed and replaced as is occasionally needed. FIG. 1A is a three-dimensional view, somewhat from the front of an appliance of an embodiment of the invention, with the external surface of the appliance being shown as semitransparent. FIG. 1B is a three-dimensional view, somewhat from the rear, of an appliance of an embodiment of the invention, without any surfaces being shown as semitransparent. The appliance 10 may comprise an adhesive or an adhesive-coated surface, sometimes referred to as a wafer 20, for purpose of being attached to the abdominal skin of the patient. The wafer could be integral with appliance 10 but does not have to be integral with appliance 10.

The appliance 10 may comprise or may be suitable to contain therewithin an inner pouch 100, which may comprise a gasket 200. The appliance 10 may further comprise an outer pouch 300, with the inner pouch 100 generally being contained within outer pouch 300.

Outer Pouch

The outer pouch 300 may serve any one or more of various purposes. The outer pouch 300 may generally define the overall external visual appearance of the appliance 10. The outer pouch 300 may be robust against possible mechanical insult or minor abrasion, thereby protecting the inner pouch 100 from those same factors. The outer pouch 300 may be substantially waterproof so as to serve as a secondary containment for waste matter in the event that the inner pouch 100 for any reason leaks or ruptures. The outer pouch 300 may be sufficiently large so as to contain the inner pouch 100 even when inner pouch 100 is in a full load condition, and the outer pouch 300 further may have extra space in addition to that amount of space.

The outer pouch 300 may comprise an outer pouch proximal layer 322 and an outer pouch distal layer 324. Outer pouch proximal layer 322 and outer pouch distal layer 324 may be originally-separate pieces of material that are joined to each other to form outer pouch 300. Joining could be performed by thermal joining, laser welding, adhesive, stitching, or by other methods known in the relevant art. More specifically, in the region of the lower portion of the appliance 10, the outer pouch proximal layer 322 and the outer pouch distal layer 324 may be joined to each other by a seam or joint. Alternatively, it is also possible that outer pouch 300 could be made as a unitary construct of appropriate shape, such as by blow-molding or by other methods.

In the region of the upper portion of the appliance 10, the outer pouch 300 may be able to be opened or closed to provide access for installing and removing inner pouch 100. There may also be a filter 340 attached to outer pouch distal layer 324.

The outer pouch proximal layer 322 may have a hole therethrough for access to the patient's stoma. On the proximal side of the outer pouch proximal layer 322 there may be attached thereto wafer 20, which may be or may include adhesive, to accomplish attachment of the appliance 10 to the patient's abdomen. The wafer 20 may have a hole therethrough, which may at least approximately align with the hole through the outer pouch proximal layer 322.

The outer pouch 300 may be constructed of a plastic film with odor barrier properties. Such films may comprise multiple layers, such as a layer of PVDC (polyvinylidene chloride) in combination with layers of ethylene vinyl acetate film, although other odor barrier films and alternate means of construction may be used. The outer pouch 300 may also contain a filter 340 that can allow passage therethrough of gas such as flatus gas, and may also absorb odors if desired. The filter 340 may, for example comprise activated charcoal for absorption of odors.

Purse Handle

Figure 1C:
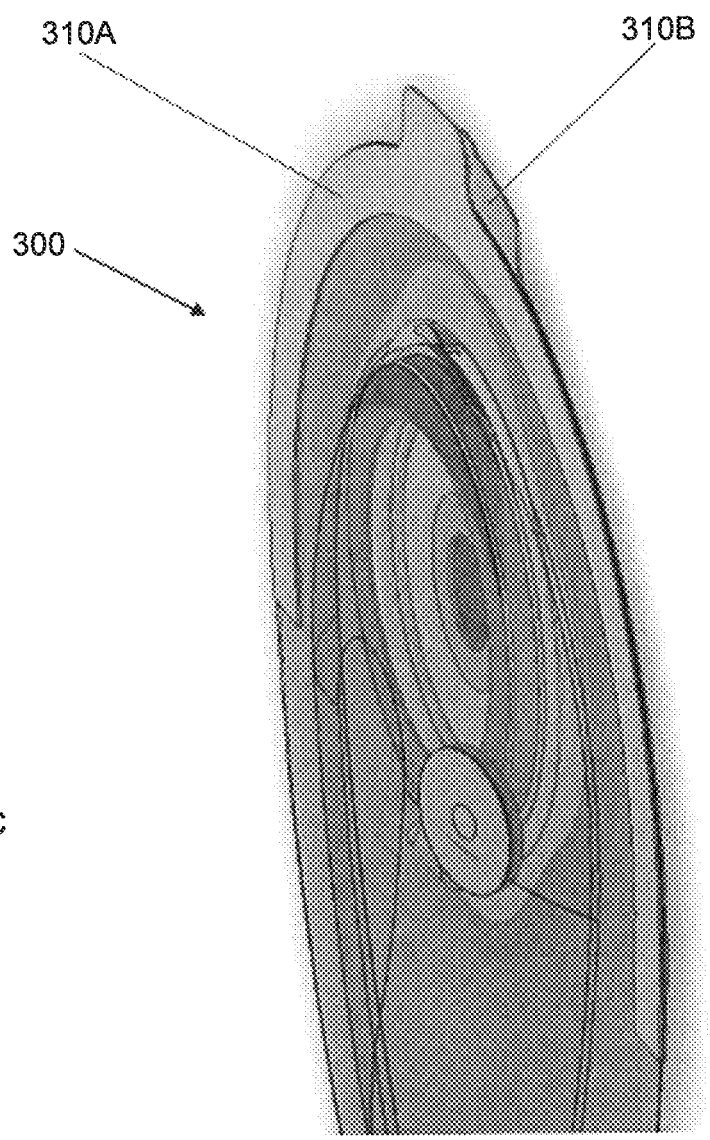

Referring now to FIG. 1C, in the region of the upper portion of the appliance 10, the outer pouch proximal layer 322 and the outer pouch distal layer 324 may be able to participate in an arrangement for opening and closing so as to provide access to inner pouch 100 when such access is desired and to enclose and contain inner pouch 100 when containment is desired. The closure may be provided by first purse handle segment 310A and second purse handle segment 310B. One of the purse handle segments may be part of or attached to outer pouch proximal layer 322 and the other of the purse handle segments may be part of or attached to the outer pouch distal layer 324. First purse handle segment 310A and second purse handle segment 310B may be designed resembling the design of a traditional purse (i.e., clothing accessory). These parts 310A, 310B may engage with each other to form a closure, but also may be easily disengaged from each other.

The engagement of the purse handle segments 310A, 310B with each other may be by an adhesive engagement, which might advantageously also provide a barrier to passage of gas therethrough. Other possible arrangements include a Velcro® (hook-and-loop) fastener or a snap arrangement. In a preferred embodiment, the mating surfaces of one or both purse handle segments 310A, 310B may have adhesive properties to enable the purse handle segments 310A, 310B to removably and sealably attach to one another. The adhesive may be a two-sided adhesive applied to the mating surfaces. The adhesive may be applied to the mating surface in liquid or spray form. In atypical embodiment, the adhesive surface could be protected by a release liner, such as silicone treated paper or plastic film, such that the release liner would prevent unwanted contact with the adhesive surface until the time of use, at which time the release liner would be removed.

Figure 1D:
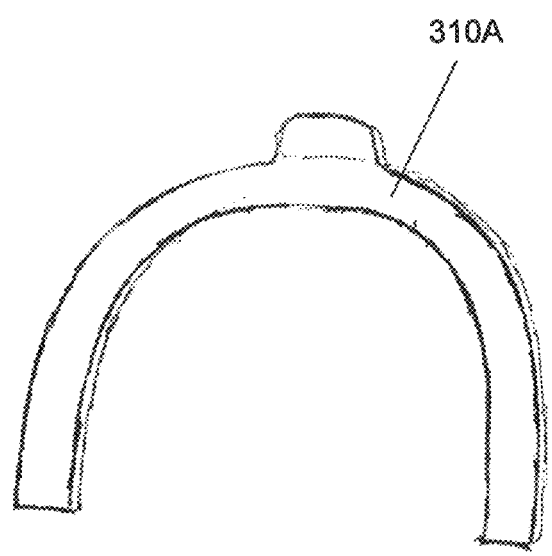
Figure 1E:
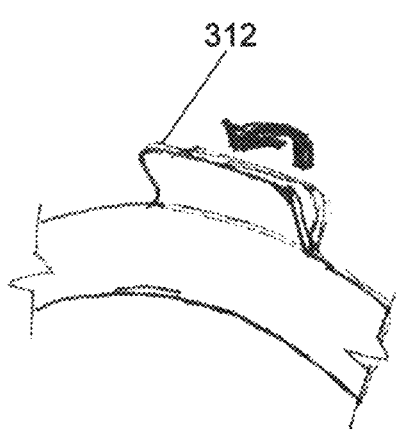

In an embodiment, as illustrated in FIGS. 1D-1E, the purse handle segments 310A, 310B may comprise tabs 312 that can be grasped to assist in separation of purse handle segments 310A, 310B and alignment of purse handle segments 310A, 310B when reclosing them. The purse handle segments 310A, 310B may have a greater bending stiffness than the material of which the rest of outer pouch 300 is made. The purse handle segments 310A, 310B may be designed so that engagement with each other may be suitable to be performed in a one-handed manner, and disengagement may be suitable to be performed in a one-handed manner. Alternatively, engagement and disengagement may be accomplished in a two-handed manner. Alternatively, it is possible that the purse handle segments 310A, 310B could be flexible to a degree comparable to the flexibility of the outer pouch distal layer 324, and the action of disconnecting the outer pouch distal layer 324 from the outer pouch proximal layer 322 could be an action like peeling a layer away from another layer by a peeling action, with the reverse being true for connecting the layers. In yet another embodiment, purse handle segments 310A, 310B may be able to be peeled from each other in order to open appliance 10, and they may be able to be rolled back into adhesive contact with each other when it is desired to close appliance 10.

In an embodiment, as shown in FIGS. 1D-1E, the tabs 312 may comprise a hinge feature that allows the tabs to bend outward from the body to prevent discomfort when the purse handle segments 310A, 310B come in contact with the wearer's skin.

The outer pouch distal layer 324 may have enough flexibility to allow it to fold or bend outward and downward to provide access to inner pouch 100. This could include flexibility in the blister that is described elsewhere herein. The flexibility or stiffness of the outer pouch distal layer 324 could be the same as the flexibility or stiffness of the outer pouch proximal layer 322, although if desired it could be different.

Figure 1F:
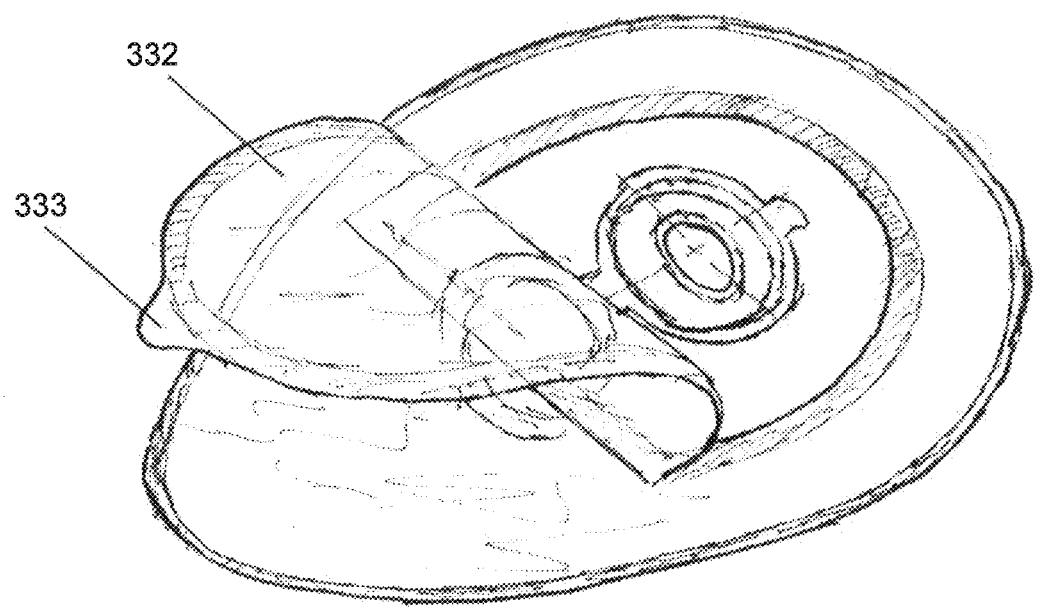
Figure 1G:
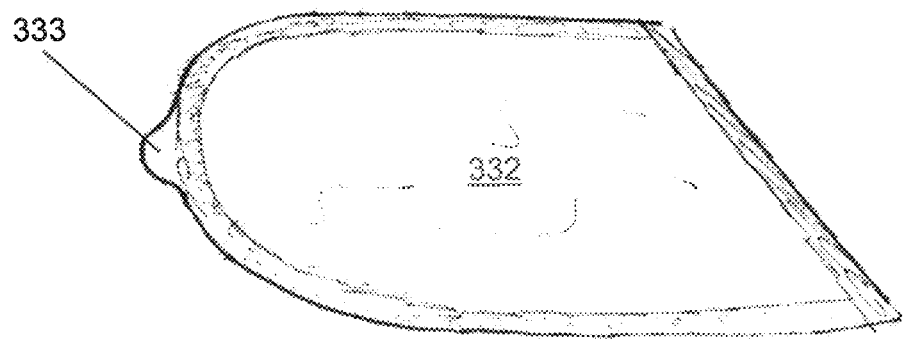

Another embodiment is illustrated in FIGS. 1F-1G. FIG. 1F shows a closure having a flap 332 that overlaps with outer pouch distal later 324 and has an overlap margin such that closure is achieved by a peelable adhesive. FIG. 10 shows the flap 332 in isolation. In such embodiment, the appliance 10 could comprise a outer pouch distal layer 324 comprising an opening, wherein the opening is large enough to allow access to the interior region of the outer pouch 300; and additionally the appliance 10 could comprise originally-separate flap 332 that is permanently attached to the outer pouch distal layer 324 at the bottom edge of flap 332, and the flap 332 could be larger in both width and height than the opening in the outer pouch distal layer 324, thereby creating an overlap margin around the opening. The overlap margin between the flap 332 and the outer pouch distal layer 324 surrounding the opening may be coated with a peelable or repositionable adhesive. Such an adhesive may be applied as a coating on the margin area of the outer pouch distal layer 324, on the margin area of the flap 332, or both. The upper edge of the flap 332 could comprise a flap tab 333, wherein the flap tab 333 would not be coated with or exposed to the adhesive. During use, the flap tab 333 can be pulled away from the outer pouch 300 to separate the flap 332 from the distal pouch film to expose the opening and provide access to the interior of the outer pouch 300. The opening would be reclosed by replacing the flap 332 over the opening and applying pressure to the perimeter of the flap 332. To help control wrinkling and distortion of the flap 332 when it is reattached, the flap 332 may comprise thicker film or less flexible film than other parts of the outer pouch 300. Alternatively, other parts of the outer pouch 300 also may also comprise a thicker or more rigid film. For example, the distal film panel of the outer pouch 300 may be more rigid than would typically be required for outer pouch distal layer 324 in order to stabilize the film panel and flap 332. Attachment of the flap 332 to the rest of the outer pouch distal layer 324 effectively results in a hinge. Such attachment could be made by adhesive bonding, heat welding, laser welding, or any suitable methods for such attachment.

Inner Pouch

Figure 2A:
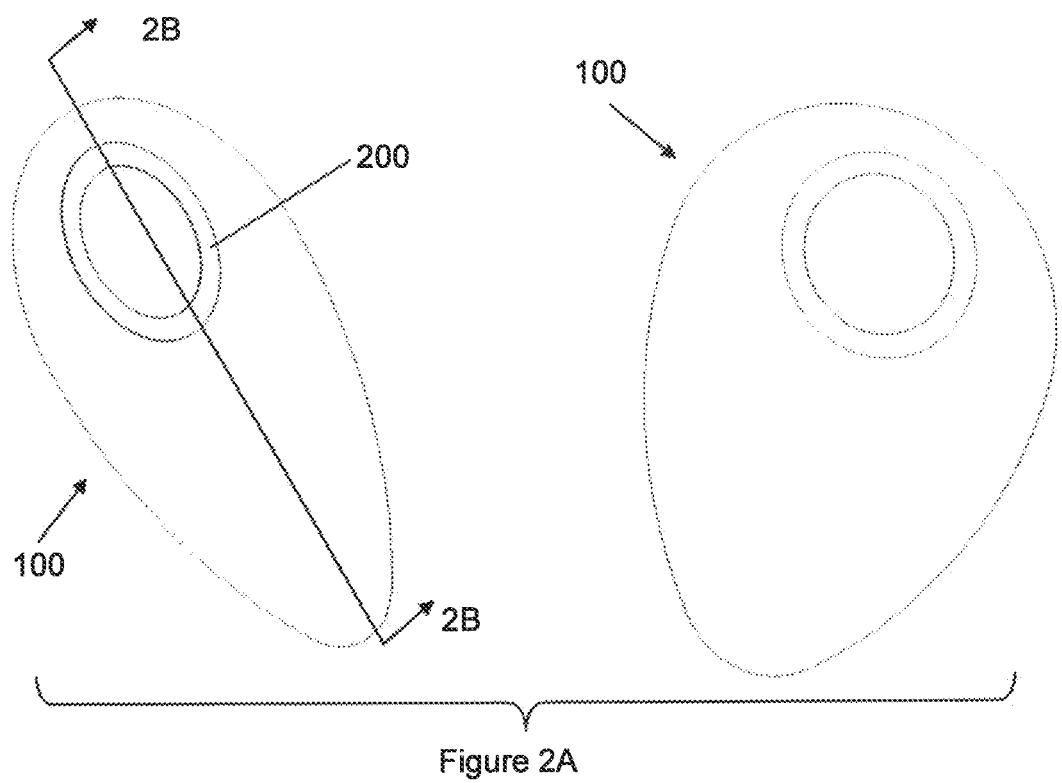
Figure 2B:
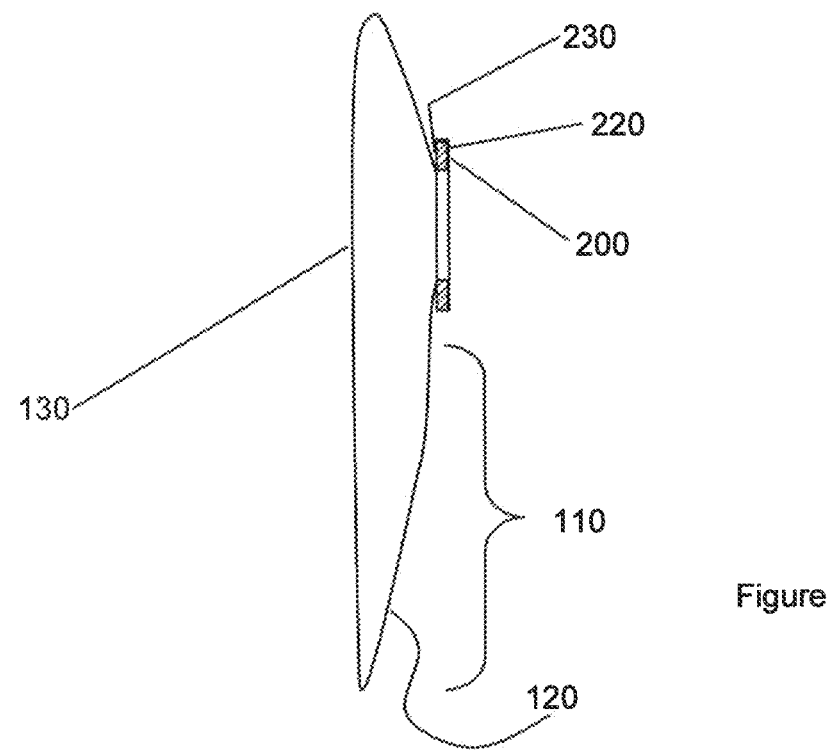
Figure 2C:
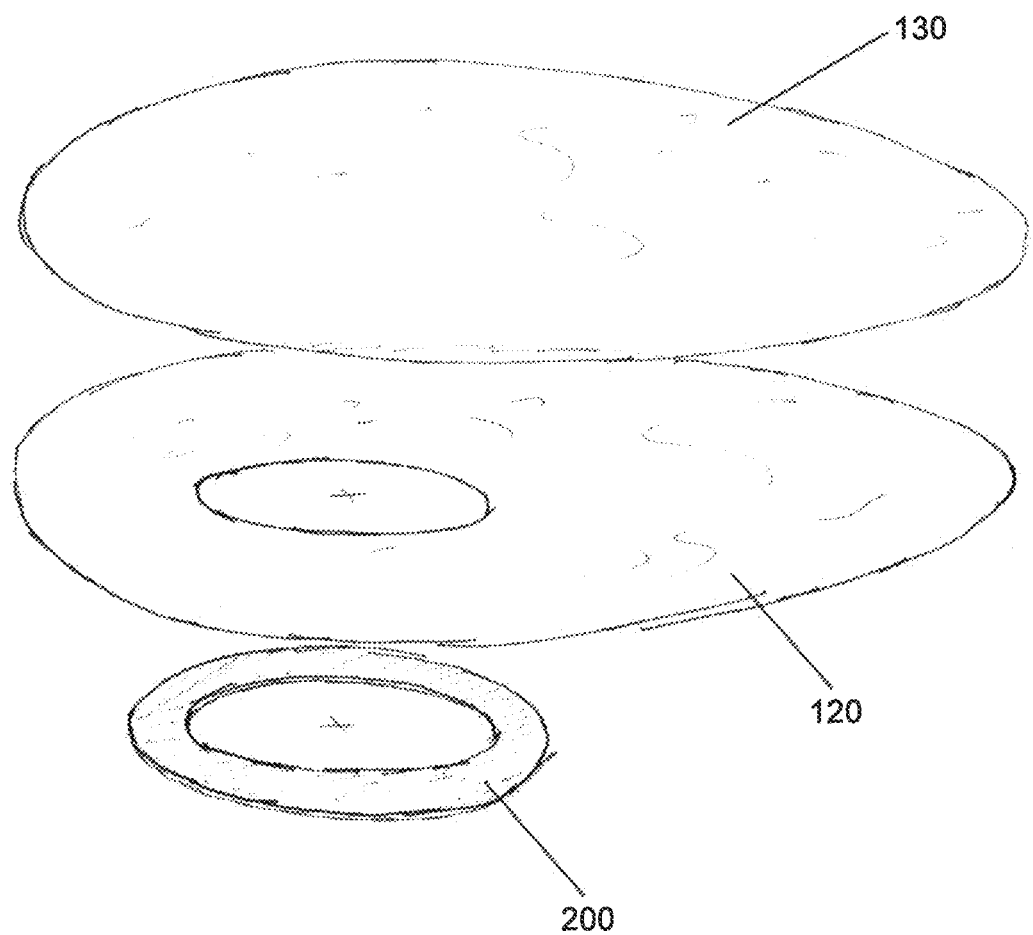

Referring now to FIGS. 2A-2C, the inner pouch 100 may be suitable to receive bodily waste from the ostomate. The inner pouch 100 may be flexible and may be generally tubular or elongated. The inner pouch 100 may generally comprise an inner pouch proximal layer 120 of flexible film material and an inner pouch distal layer 130 of flexible film material, with the inner pouch proximal layer 120 and the inner pouch distal layer 130 being attached to each other at their edges. Inner pouch proximal layer 120 and inner pouch distal layer 130 may be originally-separate pieces of material that are joined to each other to form inner pouch 100. Joining could be performed by thermal joining, laser welding, adhesive, stitching, or by other methods known in the relevant art. Alternatively, it is also possible that inner pouch 100 could be made as a unitary construct of appropriate shape, such as by blow-molding or by other methods.

The inner pouch proximal layer 120 of the inner pouch 100 may have a hole therethrough. The inner pouch 100 may further comprise a sealing member, which can be grasped by other components and participate in a seal arrangement. The sealing member could have any of several geometries. In particular, the sealing member may be a gasket 200. The gasket 200 may have a largest enveloping shape and may be generally of uniform thickness in a direction perpendicular to its largest enveloping shape. The gasket 200, in an undeformed and dry condition, may be substantially flat and may have an annular shape.

Gasket 200 may have a hole therethrough. The hole through the gasket 200 and the hole through the inner pouch proximal layer 120 may substantially align with or coincide with each other, and may be dimensioned and arranged such as to be able to fit around a patient's stoma and permit the passage of waste material therethrough.

Gasket 200 may be attached to or may be integral with the flexible film material of which inner pouch 100 is made. Gasket 200 and inner pouch proximal layer 120 may be attached to each other at the inner edges of their respective holes, or at a portion of the surface of gasket 200, or both. On a surface of gasket 200, there may be a portion of the surface of gasket 200 that is not attached to inner pouch proximal layer 120. As described elsewhere herein, it is possible that a portion of gasket 200 that does not have film material attached to it may be involved in a sealing relationship. It is further possible that a portion of gasket 200 that does have film material attached to it may be involved in a sealing relationship. Various such designs are illustrated in FIGS. 2D, 2E, 2F and 2G. In general, the film material may be attached to some or all of the surface of gasket 200 on one side or on the other side of gasket 200. The film material may be attached to the interior surface of the hole through gasket 200.

The inner pouch 100 and related components such as gasket 200 may be disposable and flushable in a toilet and may be made of a material that can dissolve or biodegrade after extended exposure to water such as in a sewer system, over a time period longer than the expected time period that a user would wear an individual pouch. For the inner pouch proximal layer 120 and the inner pouch distal layer 130, such material may be either biodegradable or nonbiodegradable. An example of such material is, but is not limited to, polyvinyl alcohol (PVA), or polylactic acid (PLA) or other materials which either may contain or might not contain biodegradable additives in a polymer matrix. Material for gasket 200 is discussed elsewhere herein.

Gasket and its Connection to Inner Pouch

In embodiments of the invention, the inner pouch 100 may comprise an elongated portion 110 and a gasket 200 located adjacent to a hole in inner pouch proximal layer 120. The gasket 200 may be generally flat and may be made from a sheet of gasket material of generally uniform thickness, such as by being stamped out of the sheet of gasket material. The gasket 200 may be of a dimension thicker than the thickness of the film material of which the elongated portion 110 of the inner pouch 100 is made. The gasket 200 may be of a generally ring-shaped or annular geometry having axisymmetry around a central axis. The gasket 200 may have surfaces that are non-adhesive with respect to stationary ring 500 and movable ring 600.

In some embodiments, the gasket 200 may have a generally flat gasket proximal surface 220 and a generally flat gasket distal surface 230, which surfaces may be substantially opposed to and parallel to each other. The gasket 200 may have a substantially uniform thickness as measured from the gasket proximal surface 220 to the gasket distal surface 230 along the generally axial direction of the gasket 200. The gasket 200 may have an inner edge that is generally circular, and may have an outer edge that is generally circular of a size greater than the size of the inner edge. The gasket 200 may be axisymmetric (of an annular shape). Features of the gasket 200 may extend substantially all the way around the perimeter of the gasket 200.

The inner pouch 100 may be made so that the elongated portion 110 of the inner pouch 100 is integral with or joined to the gasket 200. The elongated portion 110 of the inner pouch 100 and the gasket 200 could be made of the same material, or they could be made of different materials.

The gasket 200 may be joined to or integral with the remainder of the inner pouch 100. It is understood that if gasket 200 and inner pouch 100 are made of different materials, they may be joined to each other. The joint could be made by thermal processes, or could include adhesive, or could involve other processes as are known in the relevant arts. It is possible that some of the gasket 200 could be impregnated with a material that participates in the joining process. For example, some of the gasket 200 such as an appropriate surface or edge of the gasket 200 could be impregnated with polymer which may be the same as what the inner pouch 100 is made of. As still another alternative, it is possible that the inner pouch 100 could be attached to gasket 200 by an adhesive or by means of laser welding.

Figures 2D, 2E, 2F, 2G:
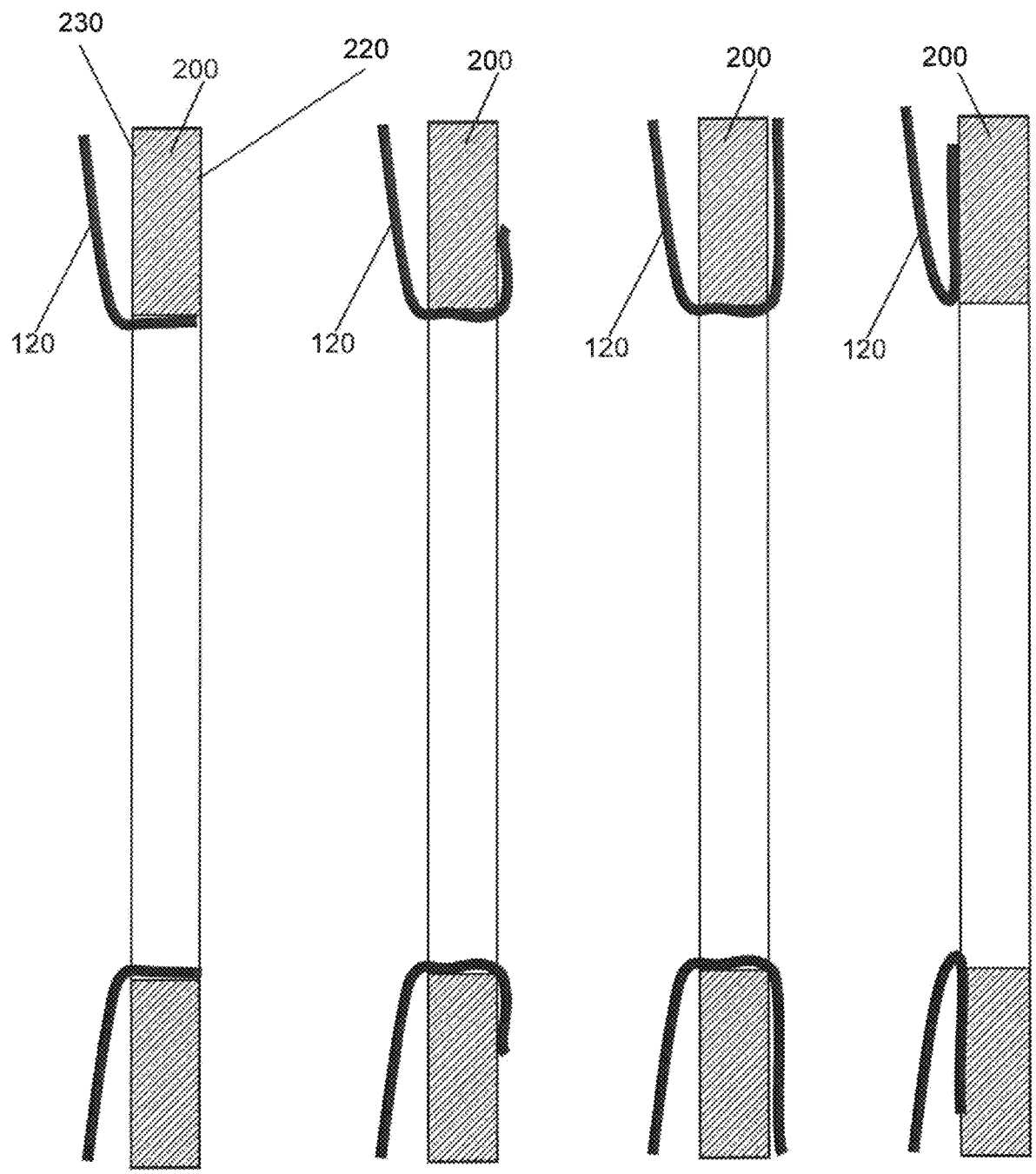

FIGS. 2D-2G show, in cross-section, various possible geometries by which the film material of inner pouch 100 may be joined to gasket 200. FIG. 2D illustrates a gasket 200 and joint such that the gasket 200, in an undeformed condition, has an inner radius and an inner radial surface and wherein the film material of inner pouch 100 is connected to the gasket 200 at the inner radius or inner radial surface of the gasket 200. The gasket 200 and the proximal layer of inner pouch 100 may be joined to each other at the inner perimeter of gasket 200, i.e., at the hole through gasket 200, and the perimeter of the hole through the proximal layer of inner pouch 100. FIG. 2E illustrates a gasket 200 and joint such that the film material is connected to the gasket 200 at a portion of the flat surface of the gasket 200, on the proximal (patient-facing) side of the gasket 200, and optionally could be connected also at the inner radius or inner radial surface of the gasket 200. FIG. 2F illustrates a gasket 200 and joint such that the film material is connected to the gasket 200 at substantially all of the flat surface of the gasket 200, on the proximal (patient-facing) side of the gasket 200, and optionally also at the inner radius or inner radial surface of the gasket 200. FIG. 2G illustrates a gasket 200 and joint such that the film material is connected to the gasket 200 at the distal (non-patient-facing) side of the gasket 200. Other geometries are also possible.

In general, the geometric interaction between gasket 200 and the proximal layer of inner pouch 100 may be such that when inner pouch 100 is in place in the appliance 10, creating the seal includes grasping gasket 200 rather than having the seal created directly by grasping the inner pouch film material in the absence of a gasket 200 or sealing member. For example, the seal might be created between the movable ring 600 and the stationary ring 500 without grasping the film material in the absence of the sealing member such as gasket 200. This would be in contrast to other known ostomy devices in which the film material of the pouch sometimes is grasped directly between two grasping surfaces. For example, in embodiments of the invention, one of the mating surfaces might contact one surface of gasket 200 and the other of the mating surfaces might contact an opposed surface of gasket 200. With reference to FIGS. 2D-2G, one of the mating surfaces might contact some inner pouch film material that is locally joined to a flat surface of gasket 200, while the other mating surface might contact the gasket 200 directly.

Figure 2H:
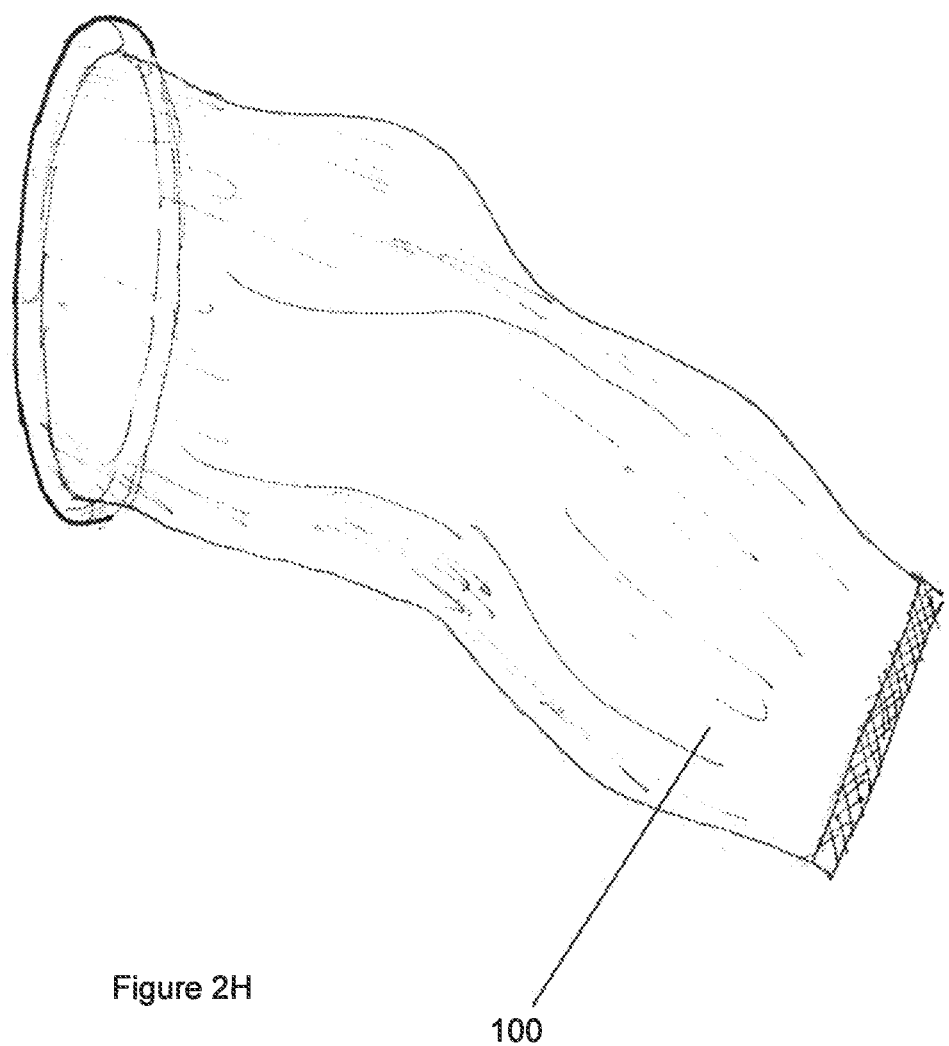

In still other embodiments, the sealing member need not be made of flat material, but rather could be an O-ring or similar structure. In such a situation, the inner pouch 100 overall may resemble a condom. This is illustrated in FIG. 2H. Surfaces of other parts of the appliance 10 that interact with the sealing member could be designed so that their shapes and dimensions are compatible with the sealing member. Still other geometries of sealing member or gasket 200 could also be considered.

Typical Dimensions and Material Properties

Dimensions that are discussed here are only for sake of example and it is to be understood that other dimensions are possible; for example, anatomically, stomas of different patients can be of different sizes and therefore it may be desirable to produce apparatus in correspondingly different sizes.

For the gasket 200, for its thickness, a typical range of thickness is from 0.25 mm to 1 mm. In regard to typical radial or diametral dimensions, the gasket 200 may, for example, have an Inside Diameter of approximately 57 mm. The inside diameter of the gasket 200 may be chosen in relation to typical anatomical dimensions of a human stoma. For the outside diameter of the gasket 200, a typical outside diameter would be approximately 74 mm. Typically, the outside diameter may be dimensioned so as to provide a reasonable amount of space for creating a joint between gasket 200 the film material of inner pouch 100, and to accommodate uncertainties in placement and tolerances in dimensions, and to provide sufficient space for lip 650 to press against, etc. These typical values of outside diameters and inside diameters imply that the width of the gasket 200, in the radial direction, would be between 5 mm and 12 mm (i.e., half of the difference between outside diameter and inside diameter). The gasket 200 and coupling may be scaled to a smaller or larger range of sizes to accommodate smaller or larger stomas. More generally, a useful range of inside diameters for the gasket 200 would be 32 mm to 100 mm.

Typical toilets have certain internal dimensions of the flowpath for the flow of waste through them. In the plumbing industry, the term describing the smallest inside diameter of the passageway through the toilet is trapway dimension. The trapway dimension is the diameter of the largest sphere that can pass through the passageway inside the toilet. The trapway dimension is roughly the inside diameter of the narrowest part of the flowpath inside the toilet. According to standards in the plumbing industry, typically the trapway dimension is at least 2 inches (51 mm), and for some toilets it can be as large as 2.375 inches (60.3 mm). Downstream of the internal passageway within the toilet, waste piping typically has a larger inside diameter than the trapway dimension, which means that the trapway dimension is the narrowest or most limiting dimension in the overall flowpath. In any event, it is quite possible that the outside diameter of gasket 200 could be larger than the inside diameter of the most limiting dimension of passageway through which the gasket 200 must flow, such as the trapway dimension of the toilet. This incentivizes that the gasket 200 be designed to be easily bendable in the out-of-plane direction, and especially to be easily bendable after it has been exposed to water such as the water of a toilet bowl, or the liquid component of stool as the appliance is worn by the patient.

In a preferred embodiment, gasket 200 is made of or comprises paper. Gasket 200 can be made of or can comprise a paper that has a high fiber content, wherein the fiber is cotton. It is believed that this helps to preserve the integrity of the gasket 200 after uptake of water. An example of a material that is suitable for use in the gasket 200 is paper that is commonly used for watercolor painting. Such paper becomes very flexible when it absorbs water but still retains its integrity. Furthermore, watercolor paper is typically impregnated with sizing that controls the rate of water uptake. This allows the gasket 200 to retain its shape if exposed to aqueous liquid during installation of the inner pouch. In an embodiment, the gasket 200 becomes flexible several minutes after installation of the inner pouch 100 as gasket 200 absorbs water in the environment inside the inner pouch 100.

In general, the gasket thickness of a "dry" unused gasket 200 can be approximately 0.45 mm, but it could range from 0.25 mm to 1 mm. A typical volumetric density of paper that can be used for gasket 200 is 0.025 lb/in$^3$, although a range of densities from 0.015 lb/in$^3$ to 0.035 lb/in$^3$ would be appropriate.

It is further possible that one side or one surface of gasket 200 could be slightly interpenetrated or laminated with a polymer, without the entire gasket 200 being impregnated with the polymer. The interpenetrated polymer or laminated polymer could provide a base that can be joined to by another polymer, or by another component made of the same polymer. Such joint could be made by heat-sealing in order to attach the inner pouch 100 to the gasket 200. The condition of being partially interpenetrated could mean being interpenetrated to less than all void volume of said material, or interpenetrated to less than an entire thickness of the gasket 200 with one surface of the gasket being free of the polymer. This also includes the concept that a layer or laminate could be bonded to the surface of the gasket 200, by any suitable method, and the film material of the inner pouch 100 could be bonded to that laminate or layer.

In many situations during use, the paper gasket would have absorbed at least some water and would have become flexible while the appliance 10 is being worn and prior to removal and disposal of inner pouch 100. In a preferred embodiment the gasket 200 can quickly absorb water or aqueous liquid if dropped into a toilet bowl and thereby, even if it had not already absorbed some water, it can quickly become soft enough to deform during flushing so that the gasket 200 can flow through the internal passageway of a toilet as well as through waste piping downstream of the toilet. As mentioned, it is possible that during use by the patient prior to flushing, the gasket 200 may also have absorbed some of the water that is a component of stool and may have become soft. It is desirable that under such conditions the gasket 200 retain its integrity and not break apart, while still becoming soft enough throughout its volume so that it can be easily deformed. It is possible that the gasket 200 becomes sufficiently flexible so that when the inner pouch 100 is full and needs to be removed, the gasket 200 can be easily pulled through the opening in the movable ring 600 when the movable ring 600 is moved out of engagement with stationary ring 500 so as to remove and replace inner pouch 100. Because the opening in the movable ring 600 is smaller in diameter than the outside diameter of the gasket 200, one reason for the usefulness of flexibility of gasket 200 can be understood.

While watercolor paper, or paper manufactured in a way similar to watercolor paper, is a preferred embodiment, other embodiments may comprise paper that comprises a different fiber from the cotton or rag used in watercolor paper. Still other embodiments may comprise different amounts of sizing, or no sizing.

Further in regard to suitable properties of the gasket material of gasket 200, it is possible to describe the gasket material as paper that has a high fiber content, and to specify it by its thickness, in points. Points is one of a variety of practical units that have come into use for describing properties of paper. In the Table 1, some of these units are tabulated and are converted to equivalent values in other units. A type of paper that has been found to work well has a thickness of approximately 0.018 inches, or 18 points. We could expect similar useful results from thicknesses in a range of +/−25% of the nominal 18 point thickness. In terms of density expressed in weight per unit area, a suitable paper for gasket 200 may have a weight of 380 g/sq m, again with a range of +/−25% with respect to the nominal value. Relationships among various units of measurement for paper properties are given in Table 1, as taken from the indicated website: https://www.google.com/search?q=Understanding+Paper+Weight+_+Support+_+OKI+Data+Americas&rlz=1C1CHBD_enUS698US699&oq=Understanding+Paper+Weight+_+Support+_+OKI+Data+Americas&aqs=chrome..69i57.2073j0j8&sourceid=chmome&ie=UTF-8

TABLE 1

| U.S. Basis Weights | | | | Caliper | Metric |
| --- | --- | --- | --- | --- | --- |
| Bond | Text | Cover | Index | 1 Point = 0.001" | GSM (g/m$^2$) |
| 20 | 50 | | | | 75 |
| 24 | 60 | | | | 90 |
| 28 | 70 | | | | 105 |
| 32 | 80 | | | | 120 |
| 36 | 90 | 50 | | | 136 |
| 38 | 100 | 55 | | 6.0 | 140 |
| 43 | 110 | 60 | 90 | | 162 |
| 47 | 120 | 65 | 97 | 8.0 | 177 |
| 54 | | 74 | 110 | | 199 |
| 58 | | 80 | 120 | 10.0 | 218 |
| | | 90 | 135 | | 245 |
| | | 93 | 140 | 12.0 | 253 |
| | | 100 | 150 | | 271 |
| | | 115 | 170 | 14.0 | 310 |
| | | 130 | 200 | 16.0 | 350 |

In yet another embodiment, the gasket 200 may be constructed from a closed cell foam or open cell foam. In such an embodiment, combinations of gasket thickness and gasket material, and foam density could be exploited to produce a gasket that is sufficiently rigid to allow convenient handling during installation and removal through the inside diameter of the movable ring 600. Materials that could be used for such a gasket include low density polyethylene, medium density polyethylene, polypropylene, or other elastomers. The foam could be flexible enough to be deformed so as to pass through the central opening 610 of movable ring 600, and to pass through a trapway of a toilet, in either a dry condition or a wet condition.

In regard to the composition of inner pouch proximal layer 120 and inner pouch distal layer 130, these components may be made of a film of polymer that is quite flexible and deformable, which contributes to making inner pouch 100 easy to flush and dispose of in a toilet. A typical thickness of the film material of which the inner pouch proximal layer 120 and inner pouch distal layer 130 could be made is 0.001 inch (25 microns), or more generally, in the range of 0.0007 inch (18 microns) to 0.003 inch (75 microns). As already described, the gasket 200 may comprise a flat sheet of a gasket material, and generally the gasket 200 would likely be thicker than the film material of which the inner pouch proximal layer 120 and inner pouch distal layer 130 are made. A typical thickness of gasket 200 is 0.25 mm to 1 mm. Thus, the gasket 200, especially when the gasket 200 is in a dry condition, might be less flexible or deformable than the inner pouch 100. Thus, there is reason to select the gasket material and to dimension the gasket 200 such that the gasket 200, upon immersion in water, quickly becomes softer or more flexible than it is in its dry condition.

Characterizing Bending Stiffness of Gasket Material

It may be desirable to further describe, evaluate or quantify stiffness properties of the gasket material, either in a dry condition or in a wet condition or both.

One criterion that affects the choice of gasket material has just been described, namely that the gasket when wet may need to deform in order to be able to be flushed in a typical toilet. This can be related to the ability of gasket 200 to deform in bending, such that an initially flat gasket 200 bends to a non-planar shape. It can be understood that the exact pattern of bending occurring in practice may be unpredictable and perhaps non-repeatable.

It is possible that when the inner pouch 100 is full or is being removed from the appliance 10, the user may need to pull gasket 200 through the central opening of movable ring 600. This may involve deforming the gasket 200 into a shape that is out-of-round or non-planar. Thus, the material for gasket 200 may be chosen so that is sufficiently flexible so that the gasket 200 can be easily pulled, in either a wet state or a dry state, through the opening in the movable ring 600 when the movable ring 600 and the stationary ring 500 are disengaged to change inner pouches 100. It can be understood that at the time of removal of inner pouch 100 from appliance 10, the gasket 200 could be in either a dry state or a wet state. In regard to the ability to flush inner pouch 100 in a toilet and pass through the trapway, the gasket 200 at that time would be in a wet state. Because usually the central opening 610 in the movable ring 600 is smaller in its inside diameter than the outside diameter of the gasket 200, the usefulness of gasket integrity and flexibility can be understood.

In connection with this criterion, it can be realized that it is possible that during use of the inner pouch 100 by the patient prior to removal and flushing of the inner pouch 100, the gasket 200 might also absorb some of the water that is a component of stool (especially for ileostomy patients), and could start to become soft. It is also possible that the gasket 200 or parts of it could remain dry. Thus, the just-described flexibility of the gasket material may be desired both in a dry condition and in a wet or partially-wet condition. At the same time, in the described wet or partially-wet condition, it may be desirable that the gasket 200 at least somewhat retain its integrity and not break apart, even though it may have become softer than in its dry state.

Figure 2I:
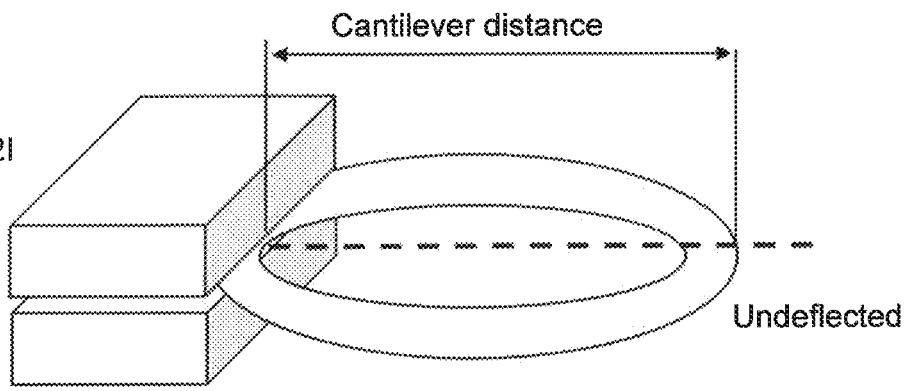
Figure 2J:
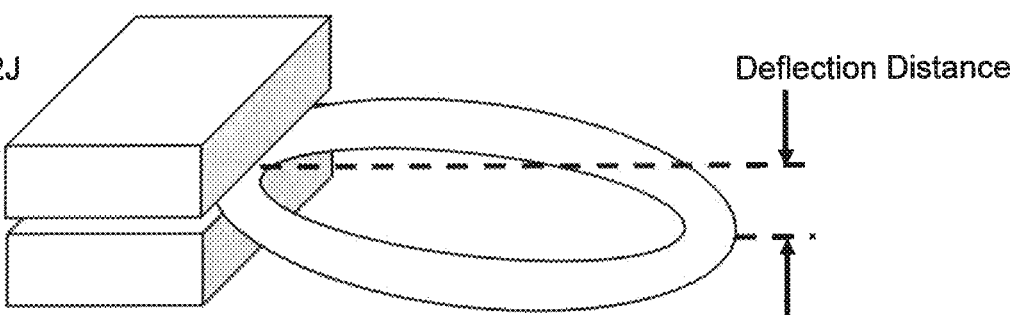
Figure 2K:
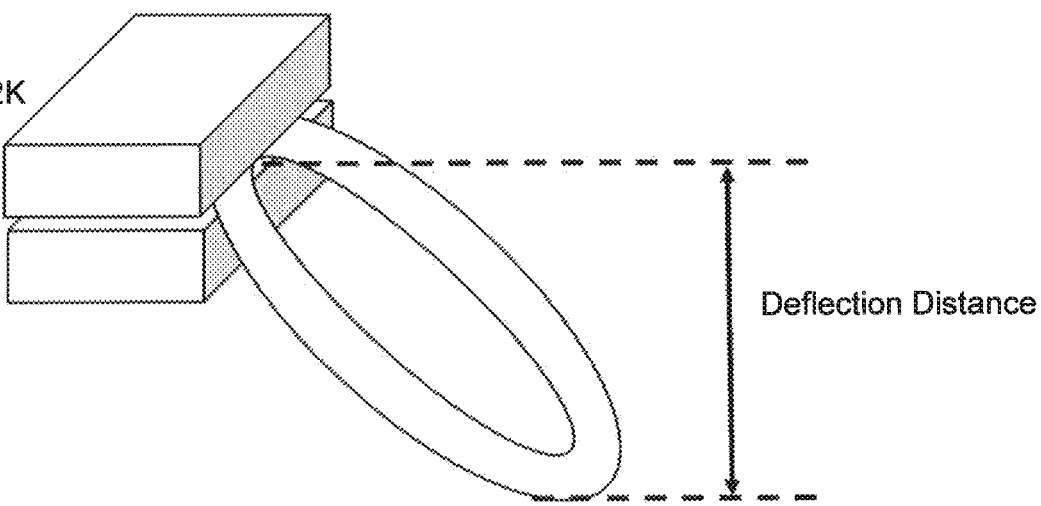

Referring now to FIGS. 2I-2K, there is illustrated an exemplary test that can be conducted to characterize prospective materials for construction of gasket 200 for embodiments of the invention. The gasket 200 may be gripped in a gripping fixture that grips a portion of the gasket 200 between flat horizontal surfaces, such that the gripped portion of the gasket 200 is in a horizontal orientation, while the remainder of the gasket 200 is cantilevered (unsupported) away from the gripping fixture, experiencing the weight of the unsupported or cantilevered portion of the gasket, in ordinary gravity. The gripping fixture may grip the gasket from one exterior edge of the gasket up to and ending at the inner circumference of the annularly shaped gasket 200. (Of course, other gripping dimensions or configurations could also be used.) FIG. 2I illustrates a gasket that is substantially undeflected, with the cantilever distance being labeled. FIG. 2J illustrates some deflection of the gasket, with the deflection distance being labeled. FIG. 2K illustrates a still greater deflection of the gasket. It is possible to compare the deflection distance to the cantilever distance in the form of a ratio of these two quantities. When the gasket 200 is in a dry condition, the weight acting to cause deflection is the weight of the unsupported portion of the gasket 200 in the dry condition. When the gasket 200 is in the wet condition, the weight acting to cause deflection includes not only the weight of the gasket material itself but also the weight of water that has been absorbed into the gasket material (and of course the gasket material becomes softer when wet). A criterion for selection of a suitable gasket material may be that when the gasket 200 is dry, its stiffness is such that the gasket 200, when held in the described fixture, either is substantially undeflected or deflects by a distance that is less than 10% of the cantilever distance. When the gasket 200 is wet, such as having been immersed in water at least 5 seconds or at least 10 seconds, the gasket stiffness may be such that the gasket 200, when held in the described fixture, deflects by more than 10% of the cantilever distance.

Flushability of Inner Pouch and Related Design Considerations

In addition to the just-described choice of gasket properties, it is possible to choose dimensions, aspect ratio, shape and design etc. of the inner pouch 100 so that the inner pouch 100 can be pulled into the toilet bowl vortex better than conventional pouches. The size and shape of an inner pouch 100 is relevant to balancing the need for the pouch to retain a sufficient volume of stool while still being able to be flushed in a toilet. In current usage, typical conventional ostomy pouches are uniform in width along their entire length so as to maximize internal volume and so that while the pouch is being worn it maintains a low center of gravity of the inner pouch 100 including its contents. However, in an embodiment of the invention, it has been found that in order to enhance flushability of the inner pouch 100, it is useful to provide an inverted teardrop shape of inner pouch 100, narrower at the bottom (away from gasket 200) than at the top (near gasket 200). When such an inner pouch 100 is dropped into a toilet, the weight of the stool contained therein, in combination with the volume of air entrained at the top of the inner pouch 100, serve to create for the inner pouch 100 a natural orientation in water wherein the narrow bottom of the inner pouch 100 is oriented toward the throat of the toilet, promoting entry of the inner pouch 100 with narrow end entering the vortex first. Such an orientation is believed to promote successful flushing of the pouch.

Figure 2L:
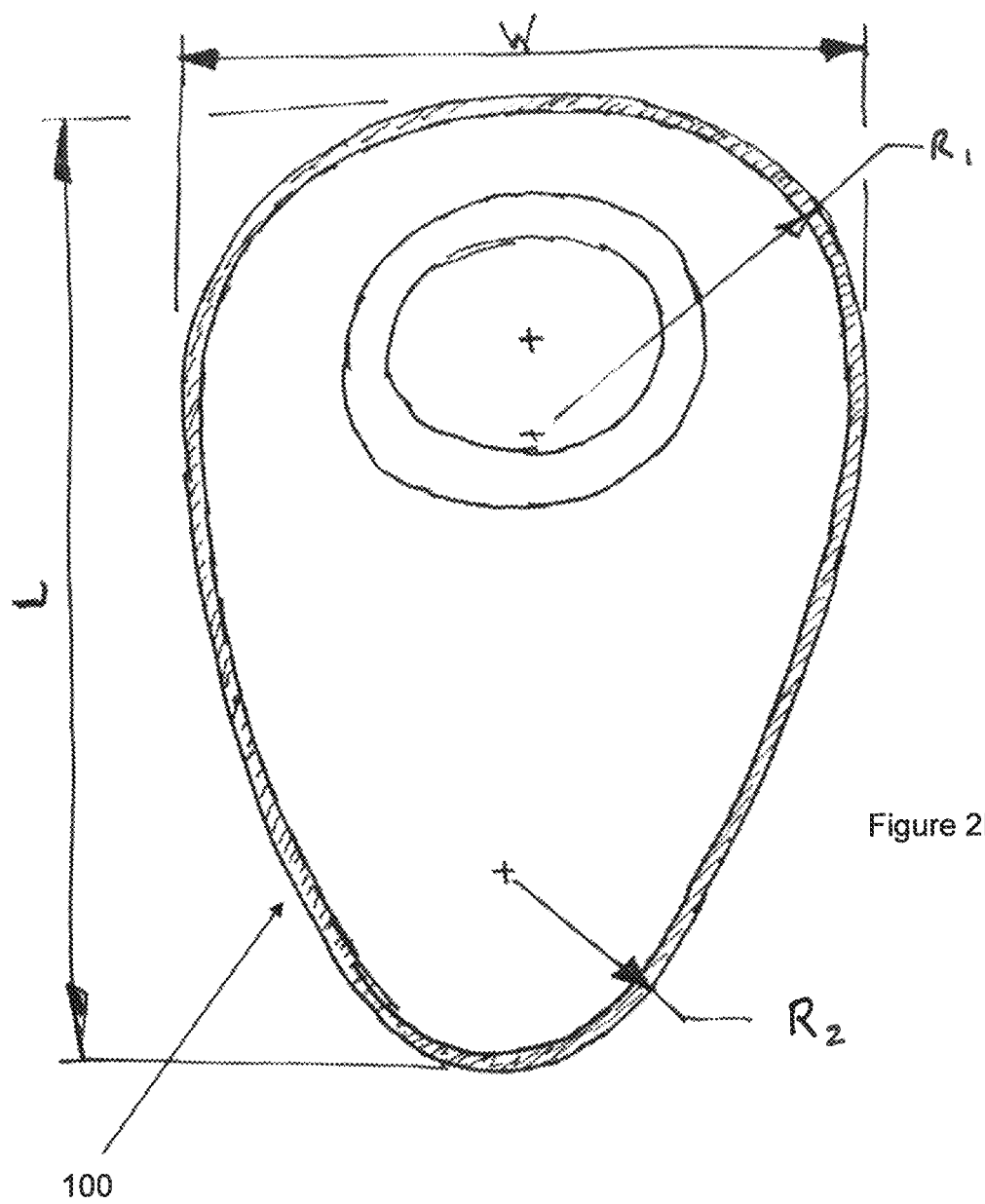

With reference now to FIG. 2L, non-limiting description is given here of possible dimensions of the inner pouch 100. These representative dimensions are believed to be helpful in regard to the ability of inner pouch 100 to flush easily and reliably in a typical toilet. R1 and R2 are descriptive of the perimeter at the outside of inner pouch 100 at the seam where a proximal layer and a distal layer of inner pouch 100 are joined to each other. If inner pouch 100 is made of some other construction, such as a unitary construction, then when inner pouch 100 is in a substantially flat condition its perimeter can be characterized by similar radii R1 and R2. R1 is a local radius of curvature of the perimeter of inner pouch 100 in the region where gasket 200 is located, or higher in the illustrated orientation. This region of inner pouch 100 can be referred to as the upper portion of inner pouch 100. R2 is a local radius of curvature of the perimeter of inner pouch 100 near or at its lowest point or bottom (with reference to typical conditions of wearing, when a patient is upright), i.e., far away from the hole and gasket 200. Dimension R1 can typically be 2.75 inch (70 mm), but can be as large as 3.25 inch (82.6 mm). Dimension R2 can typically be 1.13 inch (28.7 mm), but can be as large as 1.5 inch (38.1 mm). Dimension L can typically be 8.0 inch (203 mm), but can be as large as 10 inch (254 mm). Dimension W can typically be 5.5 inch (140 mm), but can be as large as 7 inch (178 mm). In regard to the larger values of these dimensional ranges, it cannot be guaranteed that the upper values of these dimensional ranges will work optimally in terms of performance during flushing, but they represent reasonable limits not to be exceeded. It is possible for the dimensions of inner pouch 100 to be much smaller than the values just mentioned, but those sizes would limit the volumetric capacity of the inner pouch 100, and therefore its usefulness.

Stationary Ring and Movable Ring

Referring now to FIG. 3A-3C, in one embodiment, the appliance 10 may comprise a stationary ring 500 and a movable ring 600, which in combination, in an appropriate configuration, may form an engagement with inner pouch 100. The stationary ring 500 is so called because it generally does not move, or does not move much, with respect to the patient's body. The movable ring 600 is so called because it can move (rotate) relative to the stationary ring 500. The movable ring 600 may be movable between a closed configuration, in which movable ring 600 is closely coupled to stationary ring 500, and an open configuration, in which movable ring 600 is swung away from stationary ring 500. FIG. 3A shows the assembly in a closed configuration, while FIG. 3B shows the assembly in an open configuration. FIG. 3C is a cross-section of FIG. 3B.

Stationary ring 500 may have a stationary ring central opening 510 therethrough, which may be suitable to align with the patient's stoma. The stationary ring central opening 510 may be dimensioned suitably to be larger than the patient's stoma.

Movable ring 600 may have a movable ring central opening 610 therethrough. The movable ring central opening 610 may be dimensioned suitably to be larger than the patient's stoma. When the apparatus is in the closed configuration, stationary ring central opening 510 and movable ring central opening 610 may be generally coaxial with each other.

The movable ring central opening 610 may be dimensioned suitably so that the elongated portion 110 of inner pouch 100 may be fed through the movable ring central opening 610, but the gasket 200 in its undeformed (planar) shape is larger than the movable ring central opening 610. In an assembled condition, the inner pouch 100 (elongated portion 110) may extend through the movable ring central opening 610 so that the majority of the inner pouch 100 exists on one side of movable ring central opening 610 and the gasket 200 exists on the opposite side of movable ring central opening 610.

Hinge

Figure 3D:
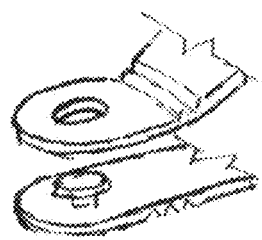
Figure 3E:
Figure 7A:
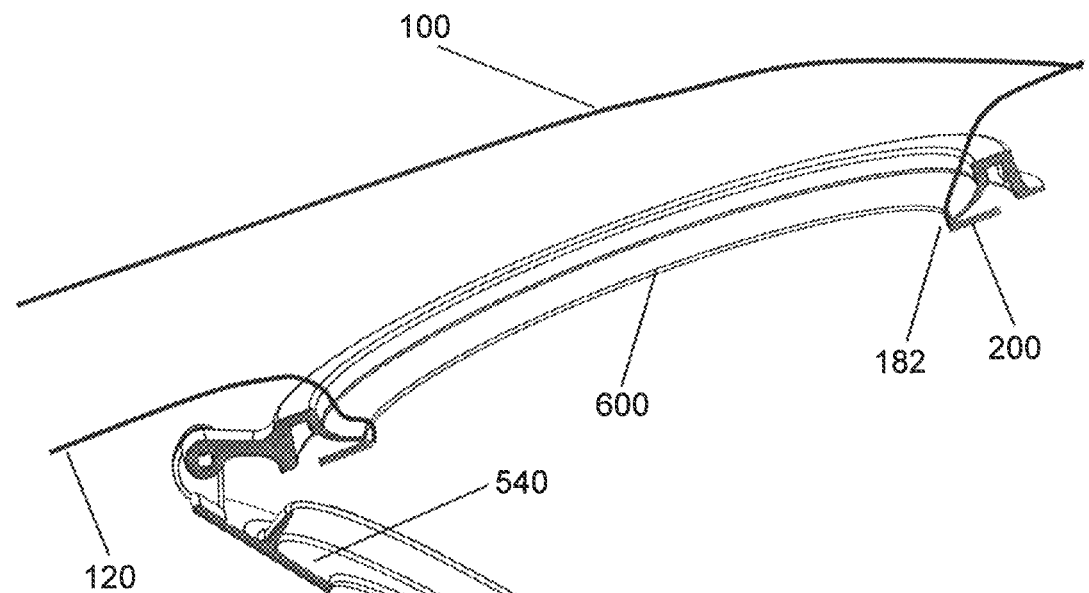

In embodiments of the invention, the stationary ring 500 and the movable ring 600 may be connected by a hinge 550. It is possible that the hinge 550 could be formed by a pin occupying holes in respective parts. A pinned hinge is illustrated in FIGS. 3A-3C. It is alternatively possible that the hinge 550 could be a living hinge 552 (FIG. 7J). In such a living hinge, the stationary ring 500, movable ring 600 and hinge 550 may all be made of the same polymeric material and may be molded in a single molding operation. The living hinge 552 may have a local region that is thinner and more flexible than stationary ring 500 and movable ring 600. In yet another embodiment, the stationary ring 500 and the movable ring 600 may be connected with a strap or living hinge or lanyard. The strap may be flat and constant in cross section along its entire length. Alternatively, the strap may be thinner at the point where it is expected to bend in the manner of a hinge. Alternatively, the strap may comprise a loop midway along its length to define a hinge. In an alternate embodiment, the stationary ring 500 and the movable ring 600 may be molded separately, and portions of the strap may subsequently be joined together by means of bonding, welding, a snap fit, or other means. FIG. 3D shows a snap-together strap. FIG. 3E shows a swaged strap. The hinge 550 may be selected from the group consisting of: a pinned hinge; a living hinge; a welded-together hinge; a snap-together hinge; a swaged strap; a snap-together strap; other forms of strap; and a lanyard. Still other hinge arrangements are also possible.

The hinge 550 may constrain movable ring 600 relative to stationary ring 500 such that substantially the only degree of freedom of motion permitted between the rings 600, 500 is rotation of movable ring 600 around the axis of rotation of hinge 550. Alternatively, it may be that some feature of the hinge permits some limited amounts of either translational or rotational relative motion in other degrees of freedom. For example, a living hinge might provide some amount flexibility in degrees of freedom other than the primary type of rotation, whereas a pinned hinge would provide little or no flexibility in degrees of freedom other than rotation around the pin axis of the pinned hinge.

The hinge 550 may define or constrain the alignment of movable ring 600 and stationary ring 500 with respect to each other. The hinge 550 may permit rotation around the hinge axis, but might permit little or no motion of any other type. For example, hinge 550 may constrain the positions of movable ring 600 and stationary ring 500 such that when movable ring 600 is swung close to stationary ring 500 typically with gasket 200 in place between rings 500, 600, the closure features of the respective rings 500, 600 are close to being in position to engage each other. Alternatively, the constraint could be looser than just described.

In relation to the overall appliance 10 and the patient in general, there are various possible angular locations, with respect to the wearer's body axes, of the hinge 550 between the stationary ring 500 and the movable ring 600. What is illustrated herein is that the hinge 550 is positioned below the patient's stoma, if the patient is in an upright position. Thus, the hinge 550 would be at the vertically lowest location of the rings 500, 600. This orientation should provide good access for the patient to change inner pouches 100. As a result, going from the closed configuration to the open configuration of the rings would involve swinging the movable ring 600 away from and downward with respect to the user's head or upper body. Going from the open configuration to the closed configuration would involve swinging the movable ring 600 toward and upward with respect to the user's head or upper body. Of course, other orientations of hinge 550 with respect to the user's body are also possible.

Figure 3F:
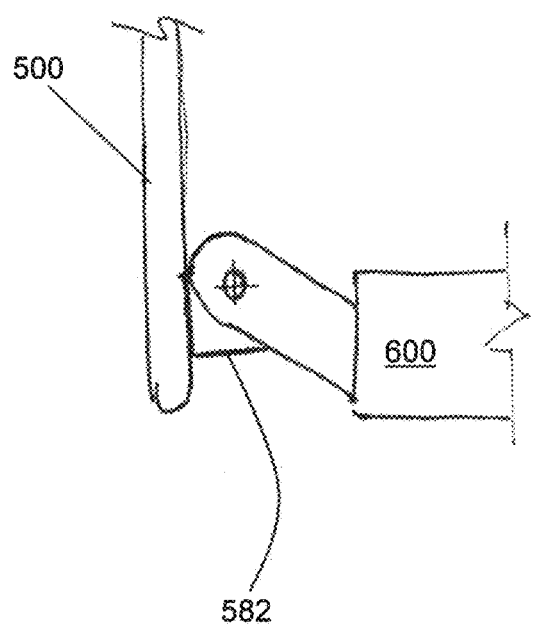

It is possible that the design could determine the angular extent of rotation of movable ring 600 that occurs in moving between the closed configuration and the open configuration. For example, it is possible that the position of movable ring 600 in its open orientation could be considered to be swung approximately 90 degrees from the position of movable ring 600 in its closed orientation. For example, if the position of movable ring 600 in its closed orientation is considered vertical (such as if the patient's body is considered to be upright), then the position of movable ring 600 in its open orientation could be considered horizontal. It is possible that some components of the system could be designed so as to define 90 degrees as a preferred or limiting position for installing or removing an inner pouch 100. For example, an angular stop or limit 582 could be built in to the system so that the movable ring 600 is prevented from rotating more than a defined amount, such as 90 degrees, away from stationary ring 500. Such an angular stop or limit 582 could be built into the hinge 550 or into the dimensions of outer pouch 300 or other components of the appliance 10. Such an angular stop or limit 582 is illustrated in FIG. 3F. The limit could be a corner or strut or similar geometric feature, and could be on either the stationary ring 500 or the movable ring 600 or both, typically located somewhere near the hinge 550.

Figure 3G:
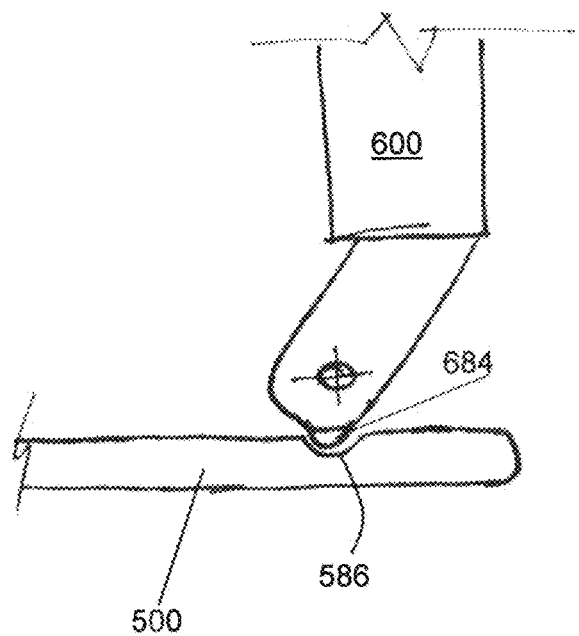

Referring now to FIG. 3G, as another alternative, it would be possible to provide a detent as part of hinge 550. A detent would provide a preferred angular position of movable ring 600 relative to movable ring 500, in the open configuration. An appropriate position could be 90 degrees of rotation of movable ring 600 as just described, but the detent might also allow motion beyond such point if the user exerts sufficient force or torque to pass the detent point. As illustrated, a detent could be formed by a detent bump or projection 684 in one of the rings 500, 600 near the hinge 550, and a corresponding detent recess 586 in the other of the rings 500, 600 near the hinge 550, at appropriate places on elements that participate in the hinge action. Either or both of the detent bump 684 or detent recess 586 could be deflectable sufficiently to allow the parts to enter the detent position or leave the detent position. It could be provided that the rotation could continue beyond the detent position if sufficient torque is exerted. Alternatively, the detent position could also be a limit of angular rotation.

The dimensions of the outer pouch 300 and of the purse handle segments 310A, 310B may be chosen appropriately so that when the purse handle segments 310A, 310B are open, there is enough space to allow swinging of the movable ring 600 through a sufficient range of angles so as to allow installation and removal of inner pouch 100.

Figure 4:
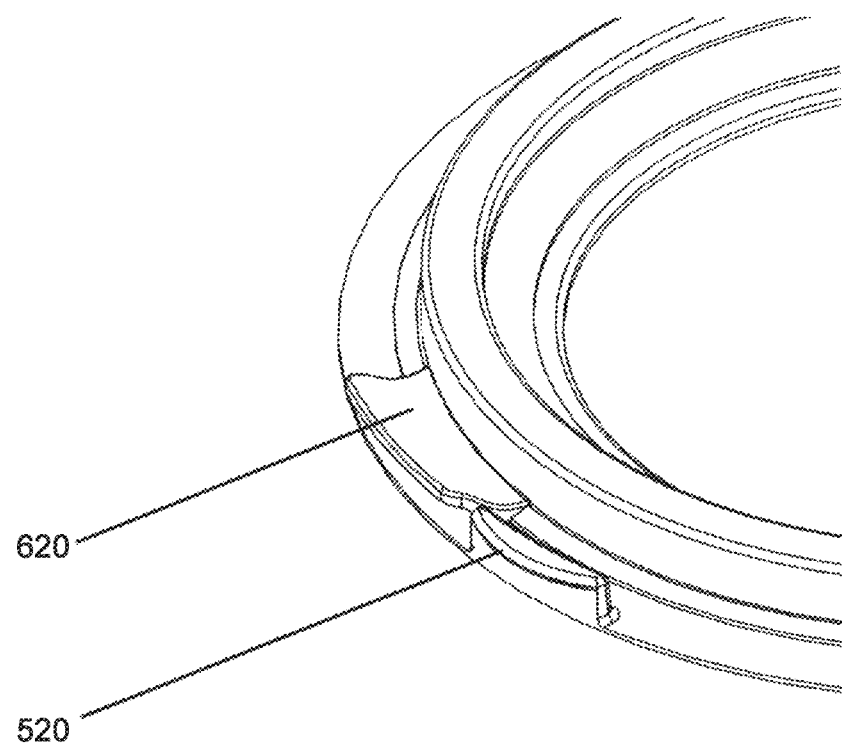

Referring now to FIG. 4, movable ring 600 and stationary ring 500 may comprise respective features such as finger-operable feature 520 on the stationary ring 500 and another finger-operable feature 620 on the movable ring 600. These features 520, 620 can be used in latching and unlatching movable ring 600 and stationary ring 500 to and from each other. These two finger-operable features 520, 620 may be near enough to each other so that they can be operated by the thumb and other fingers of one hand for latching, for unlatching, or for both. Finger-operable features 520, 620 may be slanted away from the patient's body, for convenience and access. In addition to being shown in FIG. 4, these are shown in FIGS. 3A, 3B and 3C.

Latching

Figure 5A:
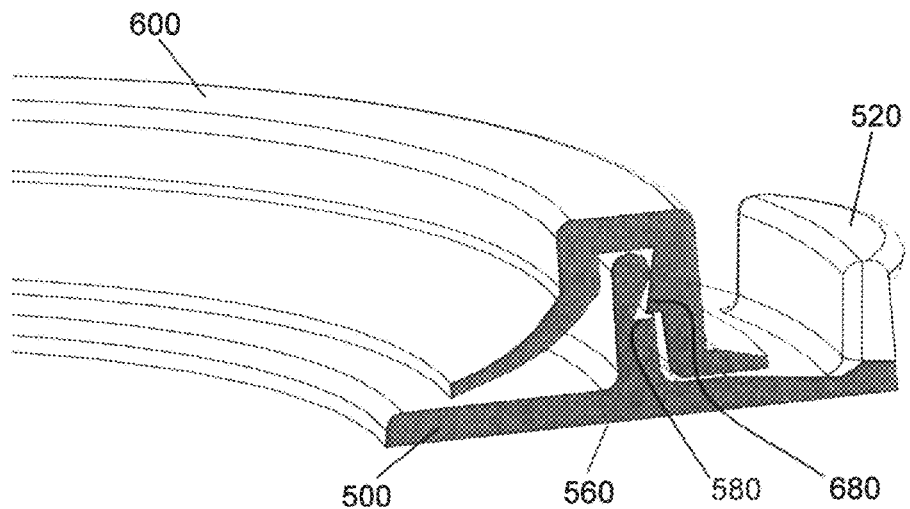
Figure 5B:
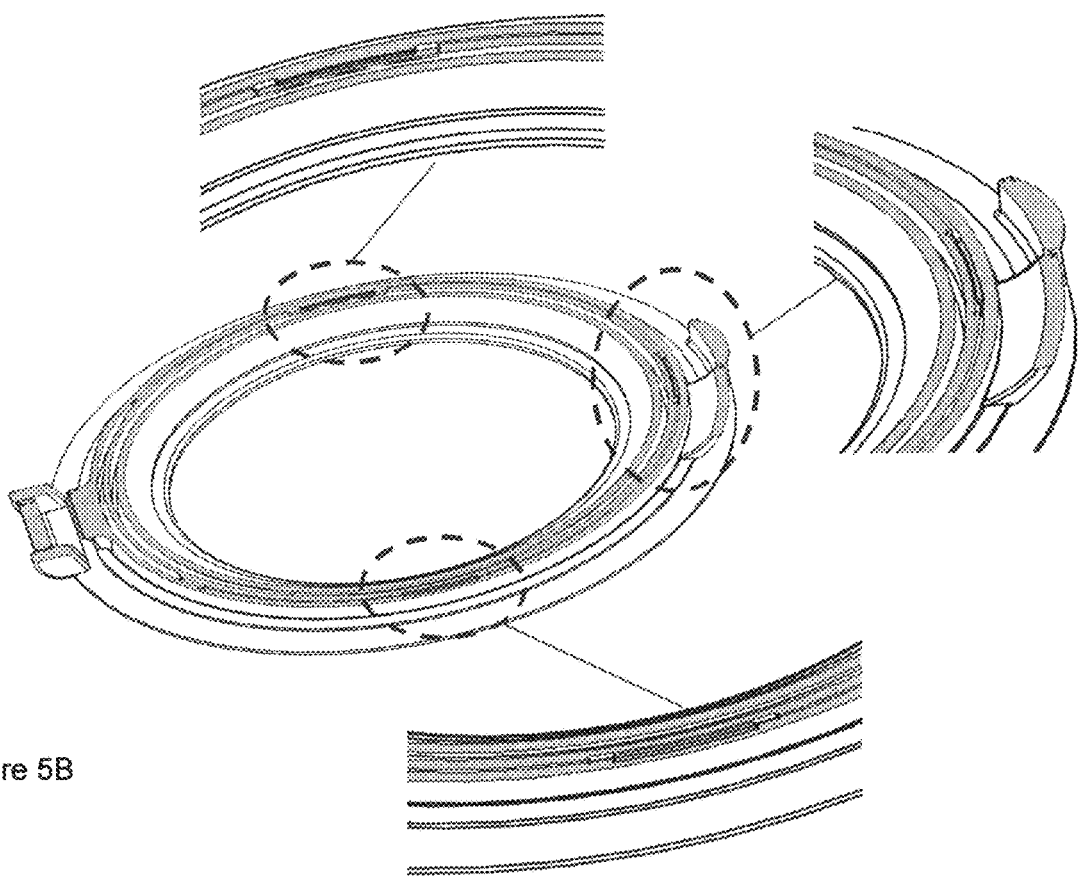
Figure 5C:
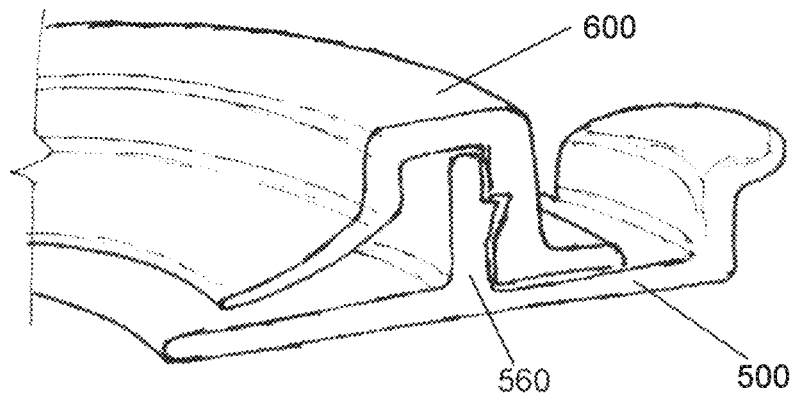

Referring now to FIGS. 5A-5C, it is illustrated that the stationary ring 500 may generally have a curved wall 560 extending outward (distally, away from the patient's body), The curved wall 560 either may be continuous around the circumference of the stationary ring or may be interrupted around the circumference of the stationary ring. A purpose of the curved wall 560 may be to participate in the latching action with the movable ring 600.

As illustrated, there are provided latches by which the movable ring 600 and the stationary ring 500 engage with each other when in the closed configuration. Stationary ring 500 and movable ring 600 may have respective latching features so that when the rings 500, 600 are in the closed configuration relative to each other, they are latched together or are in some way disposed to remain closed unless a positive action is taken to separate or release them. As illustrated, the latches are intermittent around the circumferences of rings 500, 600.

What is illustrated in FIG. 5A is a section cut through movable ring 600 and stationary ring 500 at an angular location where a latch 580 exists. As illustrated, the protrusion or wall 560 from the stationary ring 500 has a rounded top and has a wedge-shaped cutaway. The interior of movable ring 600 has an external wedge feature or protrusion 680.

When the movable ring 600 is moving toward the closed configuration, the protruding corner of the external wedge feature or protrusion 680 of movable ring 600 can ride on the curved exterior surface of the external wedge feature or protrusion 680 from stationary ring 500 as movable ring 600 moves toward stationary ring 500. In order for this to occur, either the movable ring 600 can locally deform outward, or at least a portion of the protrusion or wall 560 from stationary ring 500 can deform inward, or both of these types of deformation can occur. This can occur until the point of the external wedge feature 680 moves downward past the rounded top and into the recess, at which point there will be incentive for movable ring 600 to continue moving downward until complete latching occurs.

For unlatching, the movable ring 600 can be urged away from the stationary ring 500 using the finger tabs 520, 620. As this is happening, the sloping face of external wedge feature 680 on movable ring 600 can ride against the sloping surface of the wedge-shaped recess in stationary ring 500 until the vertex of the external wedge feature 680 on movable ring 600 passes the appropriate point on the curvature of the protrusion from stationary ring 500. Similar to what occurs during latching, either the movable ring 600 can locally deform outward, or the protrusion or wall 560 from stationary ring 500 can deform inward, or both of these types of deformation can occur. After the vertex of the external wedge on movable ring 600 passes the appropriate point on the curvature of the protrusion from stationary ring 500, movable ring 600 will be free to continue moving away from stationary ring 500, and unlatching will occur. The orientation of the slope of the mating surfaces, as shown, provides a ramp that reduces the amount of force required to separate the movable ring 600 and stationary ring 500 components.

As illustrated in FIG. 5B, the latches 580 are internal in the sense that they are not visible from the exterior of the movable ring 600. It can be noted that including latches in the wall 560 is only one of various possible ways of creating a latching interaction between the two rings 500, 600. Other designs are also possible.

As illustrated in FIG. 5B, the latching comprises latching features 580 at three discrete circumferential locations around the rings 500, 600. It is possible that a latch might not be required near the hinge 550, because the hinge 550 may serve some of the same structural or motion-constraining purposes as a latch. A latch is provided at or near the finger-operable disengagement features 520, 620, which are located 180 degrees away from the hinge 550. Additionally, latches are provided midway between the hinge 550 and the finger-operable disengagement features, in either direction away from the hinge 550. Thus, the three latching features 580 and the hinge 550 may be disposed at intervals of approximately 90 degrees around the circumference of the rings 500, 600. Other spacings and numbers of latching features 580 are also possible. The number and locations of latches may be chosen to achieve acceptable forces and feel for connection and disconnection of the movable ring 600 and the stationary ring 500. The quantity and positioning of such side latches is at the discretion of the designer and it is possible for there to be no such side latches at all.

Figure 5D:
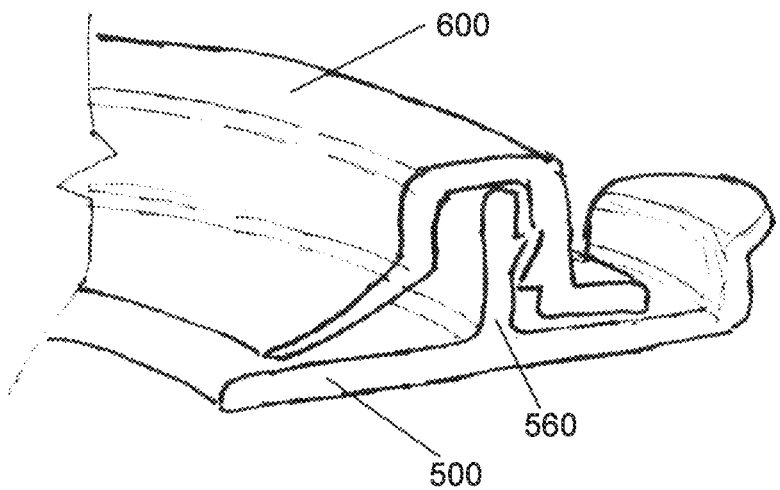
Figure 5E:
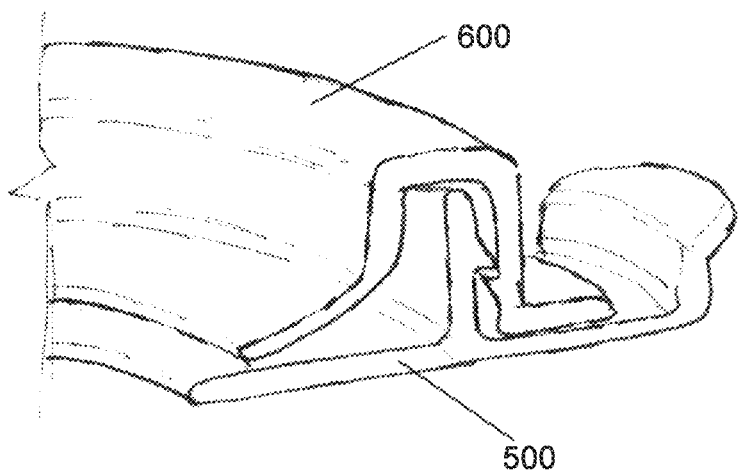

In general, the wedge shapes involved in the latching can be oriented with various slopes (angles) and in various directions, as desired. FIGS. 5C, 5D and 5E illustrate additional possible configurations of interacting shapes that can provide latching action. FIG. 5C shows the wedge in an orientation different from the orientation of FIG. 5A. In this embodiment, the interior of the movable ring 600 may have a cutaway and the protrusion from the stationary ring 500 may have a complementary protrusion. This change could result in latching and unlatching characteristics that are different from the characteristics of the latch illustrated in FIG. 5A. FIG. 5D is similar to FIG. 5C except for having external protrusions both in the mating surface on the stationary ring 500 and in the mating surface on the movable ring 600. In an embodiment as shown in FIG. 5E, the sloping surfaces may be configured to produce a relationship that requires a relatively small amount of force to engage movable ring 600 with stationary ring 500 and requires a relatively larger amount of force to disengage movable ring 600 from stationary ring 500. Still other configurations are also possible. The configuration of the shapes involved in latching can be substantially identical at various places around the circumferences of rings 500, 600, or if desired the configuration can change as a function of position on the circumference.

Figure 5F:
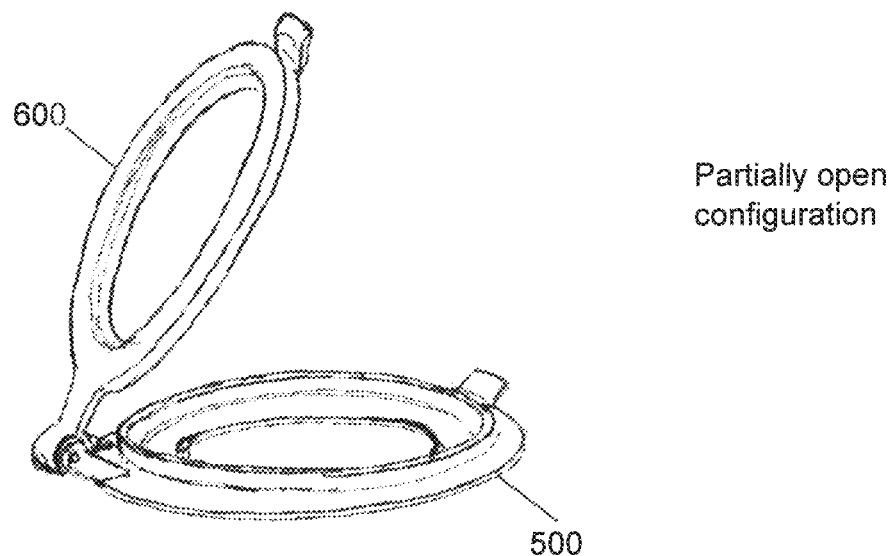
Figure 5G:
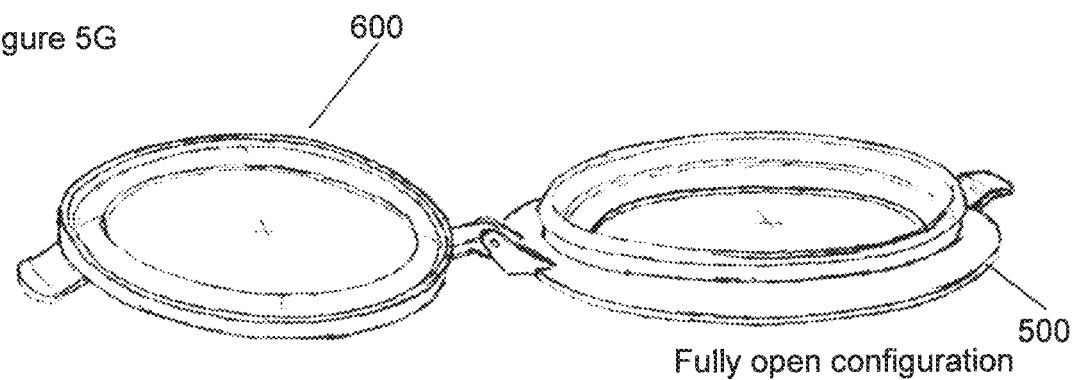
Figure 5H:
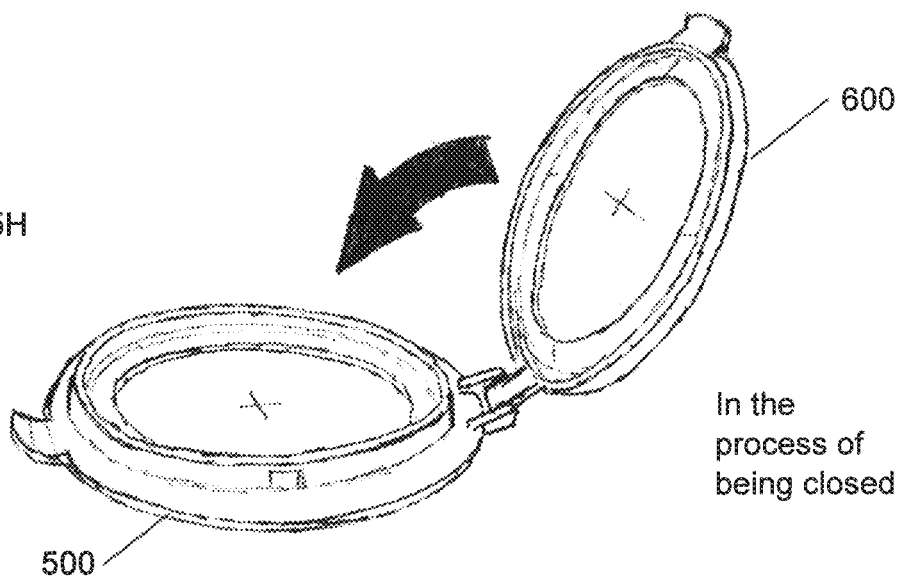

In still other embodiments, the latching features 580, 680 may extend continuously around the circumferences of stationary ring 500 and movable ring 600. Even if the latches do not extend continuously around the full circumference, they may extend continuously around at least 270 degrees of circumference. This is illustrated in FIGS. 5F-5H. These alternate embodiments may be chosen in combination with the choice of durometers of materials used to manufacture the components such as rings 500, 600. If the rings 500, 600 are less rigid, there may be more reason for the latches 580 to be continuous around the circumference or at least a large part of the circumference of rings 500, 600. Making the rings 500, 600 less rigid may improve patient comfort, as discussed elsewhere herein.

Sensory Indication of Engagement of Movable Ring with Stationary Ring

In embodiments of the invention, attachment of the inner pouch 100 to the appliance 10, such as the closure of movable ring 600 to stationary ring 500, may be accompanied by an indication that is apparent to one or more senses of a patient. For example, there may be an audible indication in the form of a snapping sound when correct latching or engagement is achieved. It is further possible that there could be provided a visual indication of correct latching or engagement. Another type of indication of engagement can be a tactile indication that is provided by an abrupt or noticeable change in the amount of force needed to urge respective parts toward engagement with each other. The sensory indication could be such as to be helpful to a patient who is installing or removing an inner pouch 100 even if the patient does not have the ability to directly see what he or she is doing at the appliance 10.

It can be noted that the force to urge respective parts toward and into engagement with each other can be applied without exerting significant unreacted force on the patient's abdomen. It can be desirable to avoid exerting significant unreacted force either directly or indirectly on the patient's abdomen, especially for patients whose stomas have not yet fully healed after surgery. As illustrated in FIG. 4, the force to achieve closure and engagement between the two rings 600, 500 can be provided by exerting force on a movable ring tab 620 that is structurally connected to movable ring 600 and on a stationary ring tab 520 that is structurally connected to stationary ring 500. The movable ring tab 620 and the stationary ring tab 520 may be located in close proximity to each other, such that force may be exerted on one of those tabs by a thumb or finger of a person's hand, and a similar opposed force (reaction force) may be exerted by a finger or thumb of the same hand. The two tabs 620, 520 may be approximately side-by-side in relation to each other. The two tabs 620, 520 may be spaced a short distance away from the patient's body to make it easy to place a thumb or a non-thumb finger in appropriate places to achieve the described exertion of forces. With such a geometry, it can be arranged that the forces exerted by the respective fingers approximately cancel each other out. As such, the only net force that need be transmitted to the patient's abdomen is the difference between those two forces, which is likely to be much smaller than the absolute magnitude of either of those forces. In fact, it could be arranged (although it is not illustrated herein) that one of the tabs 520, 620 could be a whole tab while the other tab 620, 520 is split into two half-tabs that are symmetrically located with respect to the whole tab and allow the whole tab to fit between them, with the two half-tabs being dimensioned such that a single finger or thumb can act on both of them. Such a design would be especially useful for purposes of aligning the lines of actions of the finger and thumb so as to avoid creating an unbalanced moment during the described latching/unlatching activity. There could also be still other alternative designs and configurations that could achieve similar results.

The materials of construction of the stationary ring 500 and the movable ring 600 can cover a wide range, especially in terms of properties such as Elastic Modulus or Flexural Modulus. For example, the stationary ring 500 and the movable ring 600 may comprise a relatively rigid material such as Nylon, Acrylonitrile Butadiene Styrene, or Polycarbonate, which could result in the latches providing an audible and tactile snap response when closed. Such resins or other resins having similarly rigid properties may be desirable for ostomates who have little or no abdominal muscle tone or who have hernias. In such cases, a somewhat rigid stationary ring 500 and movable ring 600 may serve to stabilize the peristomal skin around the stoma, thereby extending the wear time of the appliance 10. Such a material may be chosen so as to have a Shore durometer property of 30A to 60A.

In other situations, however, a more flexible material for rings 500, 600 may allow more freedom of movement and greater comfort for the ostomate. Such flexibility can be enabled by manufacturing the stationary ring 500 and the movable ring 600 of a material having a relatively lower flexural modulus, such as Polypropylene, High Density Polyethylene, Low Density Polyethylene, or Ethylene Vinyl Acetate. For example, if a relatively soft material is desired, it may be chosen so as to have a Shore durometer property of 50A or softer, or 40A or softer, or 30A or softer. There are also other suitable resins, which also would be within the scope of the invention. When a relatively flexible material is used, it may be desirable that the latches 580, 680 comprise mating features with more geometric interference or which extend individually over longer circumferential arcs, or which extend around the entire circumference of the stationary ring 500 and movable ring 600. Such latches, when created with such soft materials, might provide reduced tactile and audible feedback, which might be a trade-off for the desired feature of greater flexibility of stationary ring 500 and movable ring 600 and their combination.

Geometric Configurations of Lip and Seal

Various designs are discussed that illustrate lip and seal configurations and other design features.

The movable ring 600 and the stationary ring 500 may comprise features that cooperate to create or improve a seal between the inner pouch 100 and the appliance 10. Features of the rings 500, 600 that are involved in the seal may extend substantially all the way around the perimeter of the rings 500, 600. One possibility (not illustrated herein) is that stationary ring 500 and movable ring 600 could both have respective generally flat surfaces that contact opposed surfaces of gasket 200 thereby creating a seal.

Figure 6A:
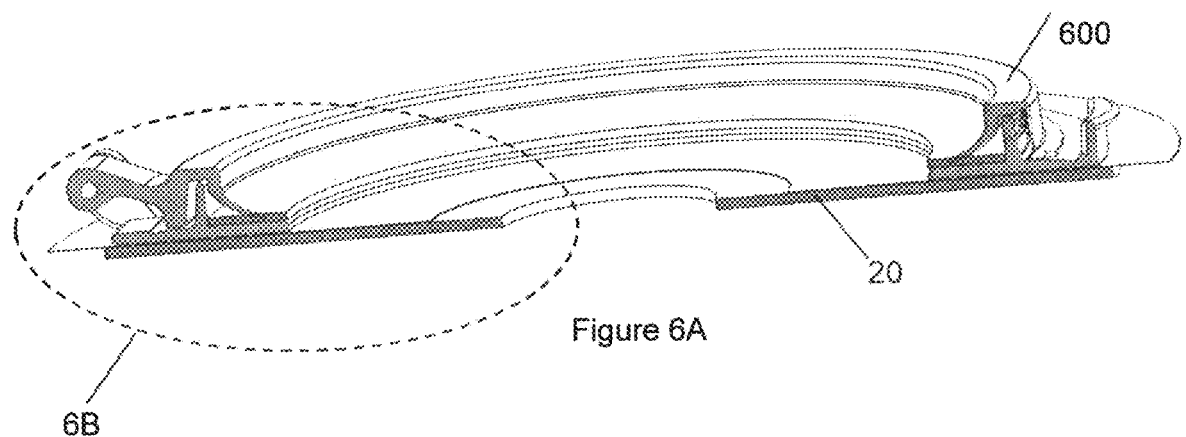
Figure 6B:
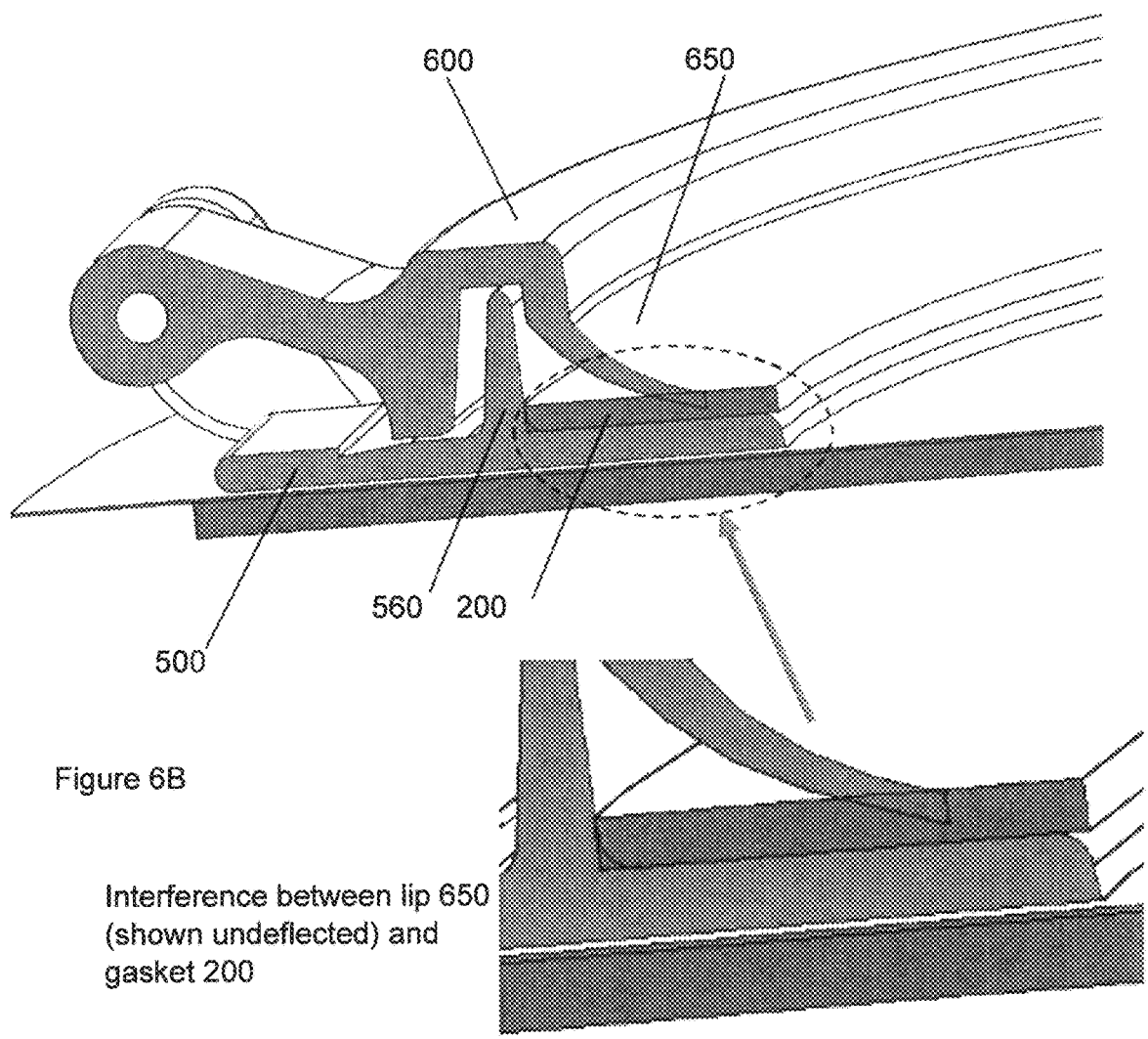

As illustrated in FIGS. 6A and 6B, the seal may be created by virtue of the one of the surfaces of sealing member such as gasket 200 resting against a substantially flat surface (in this case, a substantially flat surface 540 of stationary ring 500) while the opposite surface of sealing member such as gasket 200 is pressed upon in a somewhat narrow band that extends generally around a full circumference of the gasket 200. The component, such as lip 650, exerting the pressing force in the narrow band going around the circumference of gasket 200 may be relatively flexible, in comparison to other components of the system.

The gasket 200 may be flat. Stationary ring 500 may have a generally flat surface 540 that is dimensioned appropriately for gasket 200 to seat against the generally flat surface. Movable ring 600 may comprise a lip 650 that is dimensioned and designed to exert force on gasket 200 in a localized path so as to create a defined location of seal. Lip 650 of movable ring 600 may press gasket 200 against flat surface 540 of stationary ring 500. In connection with the lip 650 pressing on the gasket 200, it is illustrated in FIGS. 3A-3C and 6A-6B that the lip 650 is continuous around a full circumference of the movable ring 600. That may be done because in order to create a seal, it can be helpful to provide continuous sealing pressure around a circumference.

As illustrated especially in FIGS. 3C and 6B, in cross-section as illustrated, lip 650 is somewhat tapered, becoming thinner as it extends away from the parts of the movable ring 600 from which it extends. Lip 650 also is illustrated as being curved, although this is not necessary. Curvature and/or tapering of lip 650 in its undeformed shape, as illustrated, may help achieve the desired flexibility so that some of the deflection of lip 650 is achieved by bending of lip 650. However, alternatively lip 650 could be straight in its undeformed shape. At its tip which bears upon gasket 200, lip 650 could have a desired radius of curvature or could have a bead 656 or other shape.

The lip 650 may be one of the more compliant components in the load path for exerting the sealing pressure on gasket 200. Such pressure may serve to maintain a seal even in the presence of possible dimensional inaccuracies or misalignment or possible change in properties of the gasket 200 as a result of possible absorption of liquid during the time that it is in place in the appliance 10. For purposes of creating a seal as illustrated, the bending of lip 650 that is relevant is bending in a plane that contains the axis of symmetry 630 of movable ring 600. In regard to bending in this direction of bending, lip 650 may be essentially a cantilever extending away from the rest of movable ring 600. As a result of the cantilever arrangement and possible detailed shaping of lip 650, lip 650 may be less stiff than other parts of movable ring 600. Such flexibility may be achieved by lip 650 being tapered in a direction away from the rest of movable ring 600, although it would also be possible for lip 650 to be of uniform cross-sectional shape.

In an embodiment of the invention, it may be provided that the stiffness of the lip 650 and the relevant dimensions are such that the lip deflects by half of the thickness of gasket 200, or at least one-quarter of the thickness of the gasket 200, when the appliance 10 is in its closed configuration. The stiffness of the relevant components may be such that this deflection may be accomplished by a force that can be comfortably exerted with the fingers of one hand as described herein in connection with the tabs 520, 620. In FIG. 6B it is illustrated that in the absence of deflection, gasket 200 and lip 650 would interfere with each other in the sense that they are both illustrated as occupying some of the same space. It can be understood that in practice, interference is accommodated by deflection of the lip 650, and it is also possible that some local deformation of gasket 200 could occur where lip 650 presses on gasket 200.

As yet another possibility, it would be possible (FIG. 7G) that stationary ring 500 could contain a small bump 594 on the surface that faces and contacts gasket 200. The bump 594 could extend substantially around the full circumference of the stationary ring 500 and at about the same radius as the tip of the lip 650, so that the bump 594 would help to cause deflection of the tip of the lip 650. The bump 594 would contact one side of the gasket 200 and the lip 650 would contact the other side of the gasket 200.

The stationary ring 500 and the movable ring 600 may cooperate with each other to grasp gasket 200 to form a seal with gasket 200. It is possible that the pressing force exerted by lip 650 only acts on gasket 200 and does not act on any film material that makes up inner pouch 100. It is possible, although optional, that some film material may be attached to gasket 200 and may be pressed upon together with gasket 200 between movable ring 600 and stationary ring 500. Various of these possibilities are illustrated in FIGS. 7A, 7C, 7F, 7G and 2D-2G. However, as illustrated, this grasping of gasket 200 between movable ring 600 and stationary ring 500 does not grasp isolated film material between movable ring 600 and stationary ring 500 in the absence of gasket 200. In other words, in this embodiment of the invention, nowhere is there a place where one of the rings 500, 600 touches one side of the film material and the other of the rings 500, 600 touches the other side of the same film material. This is in contrast to what occurs in some conventional ostomy devices. The presence of gasket 200, which is somewhat compressible and thicker than the film material of the rest of inner pouch 100, should produce a better seal than would be achieved simply by grasping the pouch film material between two opposed surfaces.

Although generally, to create a good seal, it is desirable for lip 650 to be continuous around a circumference, in some embodiments, it is possible that the lip 650 could still produce a useful seal even if it is interrupted by some very thin slits. For example, if lip 650 contained slits thinner than the material thickness of gasket 200, there still might result in a reasonably good seal for present purposes. Such slits could be molded into the lip 650. Alternatively, slits with minimal thickness could be created through die-cutting or laser cutting.

Yet another alternative is that, instead of trying to achieve a perfect seal, there may be a usefulness to providing a passageway or path for flatus gas somewhere in the system. So, it is possible that for such reason one might deliberately design a feature in the gasket/lip interaction that amounts to a tortuous path or deliberate leak path for exit of gas.

Figure 6C:
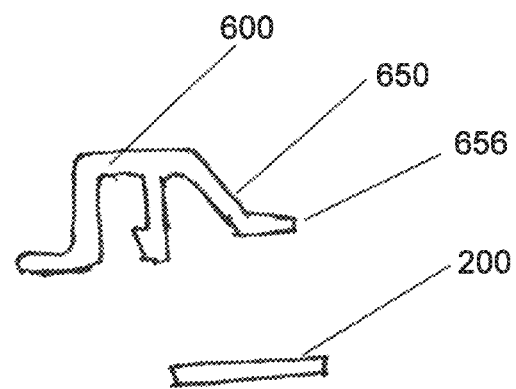
Figure 6C:
Figure 6D:
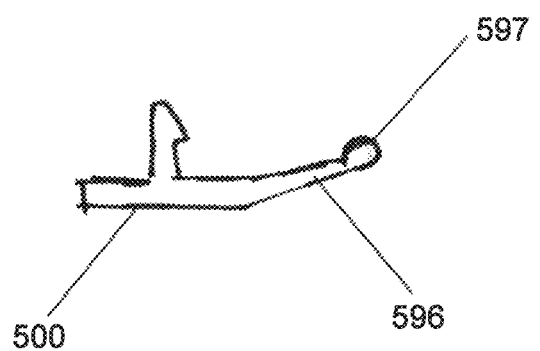

In illustrations herein such as FIGS. 3C and 6B, it is illustrated that the movable ring 600 comprises a lip 650, which in bending is more flexible than other nearby parts of movable ring 600. Another possibility, in embodiments of the invention, is that a flexible lip 596 can instead (or additionally) be provided on the stationary ring 500. This is illustrated in FIG. 6C-6D. Movable ring 600 may have a seating surface 656, which may be generally flat. It is further illustrated in FIG. 6D that if there is a flexible lip 596 on the stationary ring 500, which means that the flexible lip 550 might be close to the patient's stoma without any intervening layer of inner pouch 100, there may be provided a bead 597 at end of flexible lip 596 on stationary ring 500. The bead 597 may have a desired radius so as to not create any risk of irritating the tissue of the stoma or similar tissues. (In other designs, a similar bead could be provided at the tip of lip 650.)

In general, the relation and interaction between the inner pouch 100 and the movable ring 600 can be such as to provide any one or more or all of the following purposes:

(a) approximate positioning of the inner pouch 100 including its gasket 200, with respect to movable ring 600 at an early time, during the swinging of movable ring 600;

(b) positional locating of the gasket 200 at a relatively late time, which is the time of closure of the movable ring 600 to the stationary ring 500 (at the end of the swinging action of movable ring 600);

(c) precise positional locating of the gasket 200 with respect to movable ring 600 at an earlier time, when the movable ring 600 is not engaged with stationary ring 500 (during the swinging action of movable ring 600); and (d) frictional retention of the gasket 200 itself in movable ring 600 at that earlier time, when the movable ring 600 is not engaged with stationary ring 500 (during the swinging action of movable ring 600).

Locating and Retaining Gasket with Respect to Movable Ring

There are various possible ways of determining the location of the gasket 200 relative to movable ring 600 when the apparatus is in its open configuration. Referring now to FIG. 7A, one way of determining location is simply that where the gasket 200, at its inner perimeter, joins the associated inner pouch proximal layer 120 of the inner pouch 100, there is a neck 182 in the sense that outer regions of the gasket 200 extend more radially outward than the neck 182, and the inner pouch proximal layer 120 also extends outward from the neck 182. When the inner pouch 100 is in place in the movable ring 600 prior to swinging the movable ring 600 toward the stationary ring 500, this neck 182 resides in the central opening 610 of the movable ring 600. This neck 182 may be defined partly by the inside diameter of the gasket 200. The relation between the neck 182 and the central opening 610 of the movable ring 600 may at least loosely trap or capture the inner pouch 100 in the movable ring 600 and may at least approximately define the position of the inner pouch 100 with respect to the movable ring 600. It can be understood, however, that there might be a designed-in dimensional difference by which the neck 182 is smaller than the central opening 610 of the movable ring 600, and there also could be some dimensional tolerance of neck 182 and related dimensions. As a result, the neck 182 itself might not precisely define the location, in the radial direction, of the gasket 200 with respect to the movable ring 600. This would result in some range (possibly a small range) of possible positions for the actual location of the gasket 200 relative to the movable ring 600, such as in the radial direction. This can be referred to as a "floating" relationship. Therefore, the relationship between the neck 182 and the central opening 610 of the movable ring 600 might be relied on for a capturing of the inner pouch 100 with respect to the movable ring 600, and might be relied on for an approximate locating of the gasket 200 relative to the movable ring 600.

Figure 7B:
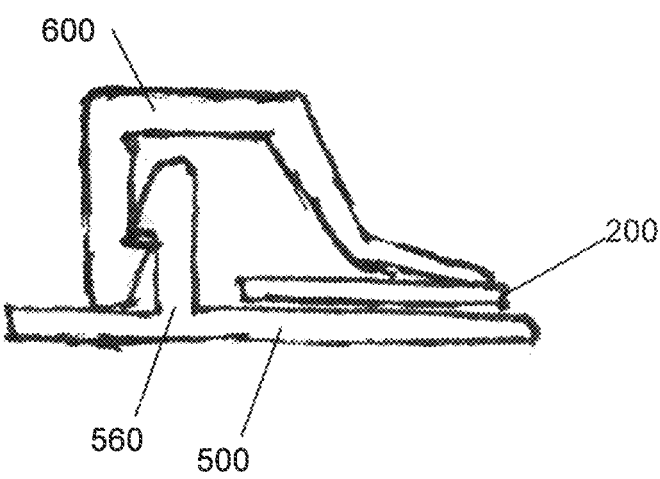

FIG. 7B shows a situation in which, in the closed configuration, the outer surface of gasket 200 is not in contact with a feature of the stationary ring 500. In such a situation, the location of the gasket 200 relative to stationary ring 500 and movable ring 600 may be determined primarily by the neck 182 of inner pouch 100 in relation to movable ring 600, especially during the swinging of movable ring 600 when the system is not in its closed configuration.

In order to achieve a greater degree of precision in locating the gasket 200 with respect to some other component, it is possible that there can be a snug fit between gasket 200 and some other component of the movable ring 600 or the stationary ring 500. A snug fit can be considered to be a fit such that even if the fit were just between the gasket 200 and the respective ring (without any benefit of the neck 182 of inner pouch 100 possibly helping to keep the gasket 200 in place by virtue of the neck of inner pouch 100 being positioned in the central hole of one of the rings), with the gasket 200 being in a dry condition, if the ring 500 or 600 were in an orientation such that the weight of the gasket 200 due to gravity would act to cause the gasket 200 to fall out of the ring 500 or 600, the snugness of fit may be sufficient so that the gasket 200 does not fall out due to gravity.

Figure 7C:
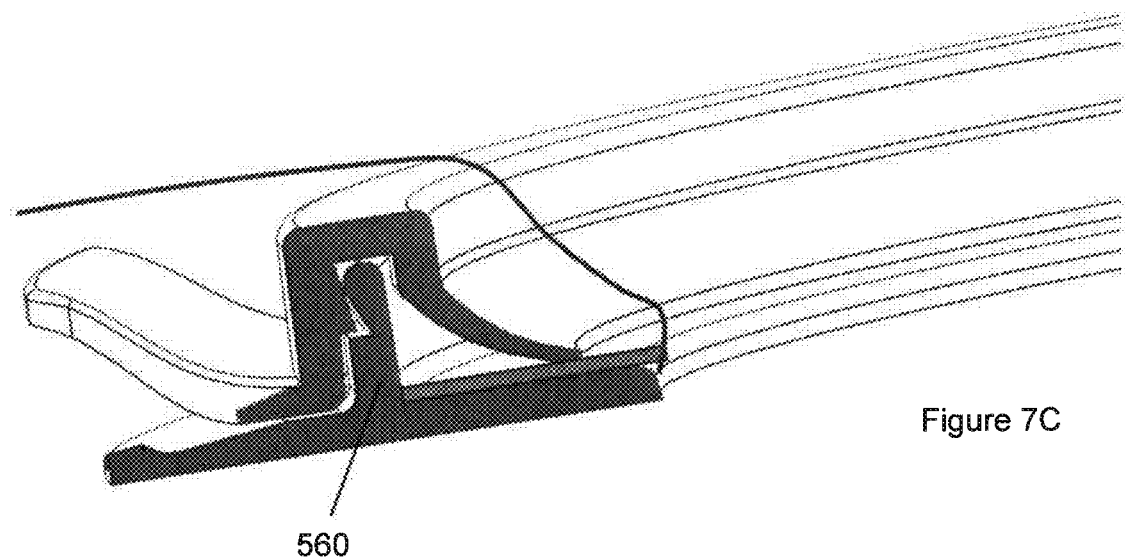

In one embodiment, FIG. 7C shows, in cross-section, a possible location of the gasket 200 in the closed configuration, such that the outer surface of gasket 200 is in continuous contact with a feature of the stationary ring 500. In this illustration, the feature that the outer surface of gasket 200 is in contact with is a continuous wall 560 of stationary ring 500. This contact can serve to determine the position of gasket 200, especially in the plane of stationary ring 500. It is possible that when the system is in its closed configuration, depending on the design of the stationary ring 500, the stationary ring 500 might define the location of the gasket 200, such as in the radial direction, fairly precisely, depending on how the various parts are dimensioned. However, this locating would only take place when the system is in or nearly in its closed configuration.

Figure 7D:
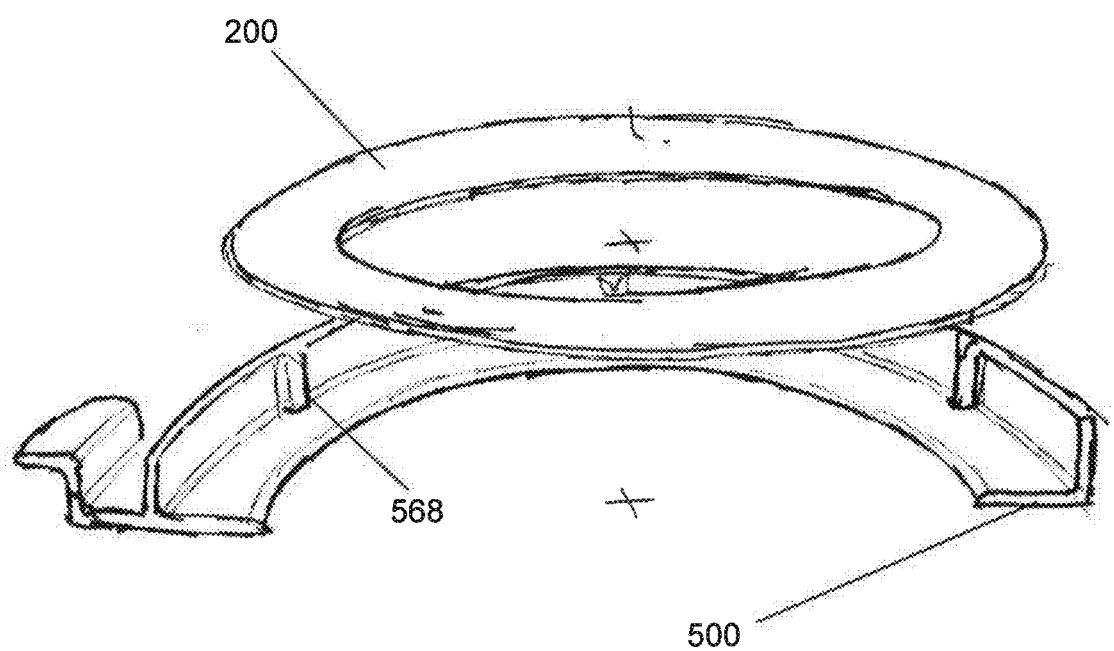

FIG. 7D shows a similar situation in which the gasket outer surface is about to be in contact with isolated features (ribs) 568 of the stationary ring 500, rather than being in continuous contact with a wall.

Figure 7E:
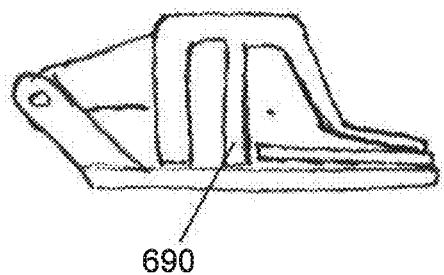

Referring now to FIG. 7E, in embodiments of the invention, in order to better define the location of the gasket 200 relative to the movable ring 600 when the movable ring 600 is not engaged with the stationary ring 500, such as during swinging of the movable ring 600, the movable ring 600 may have a gasket-locating feature 690. The gasket-locating feature 690 may serve to locate the gasket 200 relative to the movable ring 600, especially with respect to the radial direction, at those times when the gasket 200 is in the movable ring 600 and the movable ring 600 is not close to the stationary ring 500.

Figure 7F:
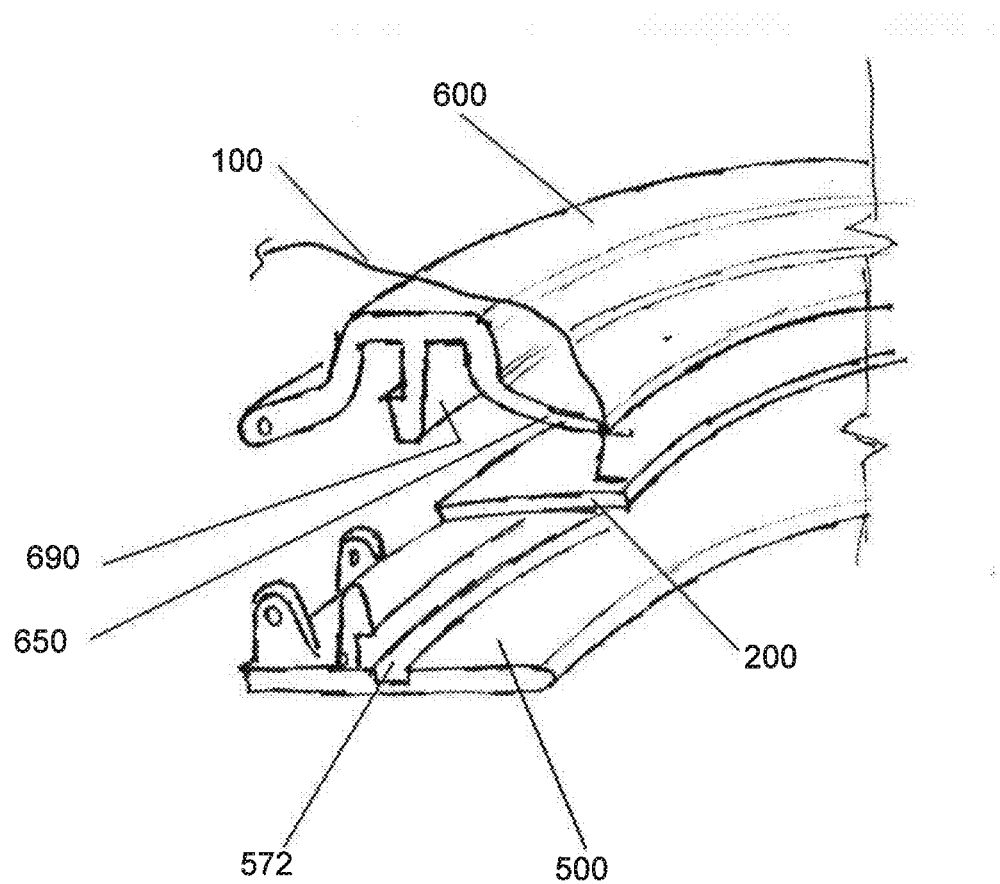

In embodiments of the invention, the gasket-locating feature 690 can be continuous around the circumference of the movable ring 600, in which case the gasket-retaining feature may be a snug fit or interference fit with respect to the outside diameter or outer edge surface of the gasket 200. In the situation shown in FIG. 7E, the gasket-locating feature 690 in the form of a wall might extend only a short distance beyond lip (downward, in the illustrated orientation) 650. The distance of overlap with gasket 200, along the axial direction of movable ring 600, might only be the thickness of gasket 200 or even only a portion of the thickness of gasket 200. Accordingly, FIG. 7F shows a similar situation further including a groove 572 in the stationary ring 500 so as to provide a receiving space for the wall or gasket-locating feature 690. This allows the wall or gasket-locating feature 690 to be longer in the axial direction of movable ring 600, allowing greater engagement with gasket 200. Having the gasket-locating feature 690 bear against the entire thickness of gasket 200 (rather than only a portion of the gasket thickness) would provide more robust engagement and locating of gasket 200. It also would provide more assurance of good retention of gasket 200 in the face of possible dimensional variations or imperfections in how the patient installs the inner pouch 100 and particularly gasket 200 into movable ring 600.

FIGS. 7G1 and 7G2 shows a partially disassembled assembly including a circumferential bump 594. Bump 594, which may extend continuously around the circumference of stationary ring 500, may be located at approximately the same radial dimension (with respect to the center of stationary ring 500) as the tip of lip 650. Bump 594 can participate in the seal involving gasket 200, and can help allow for receiving space for wall or gasket-locating feature 690 similar to what was provided by the groove 572.

Figure 7H:
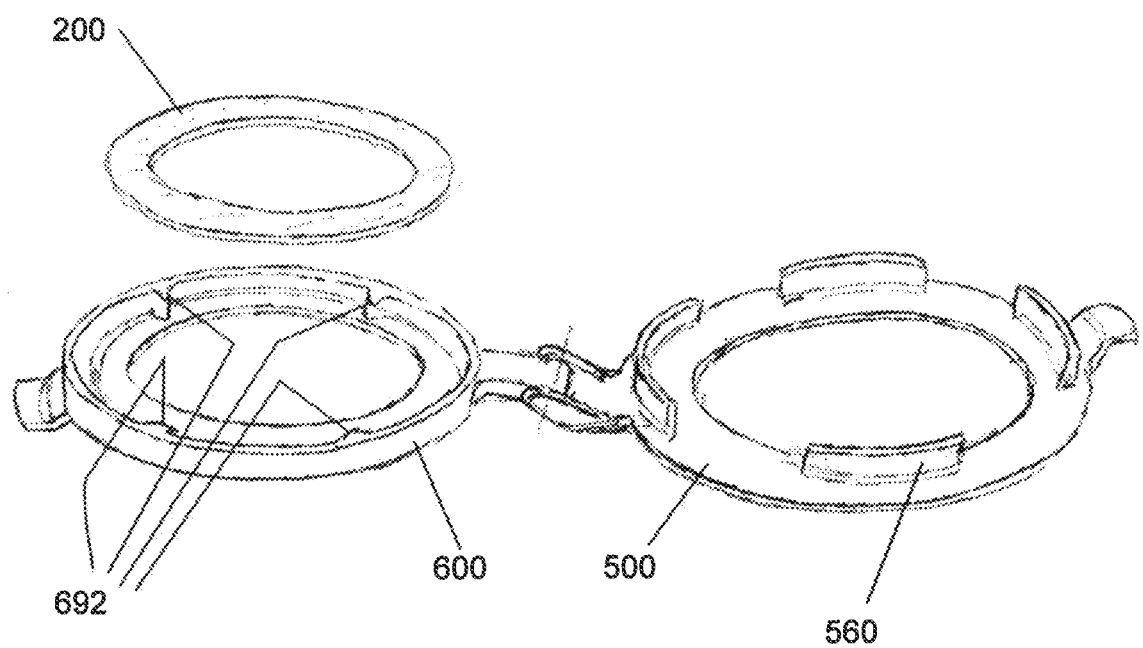

Alternatively, in still other embodiments, the gasket-locating feature 690 in movable ring 600 may be interrupted or intermittent around the circumference of the movable ring 600. In such a situation, the gasket-retaining or gasket-locating feature 690 may be gasket locating features such as tabs or ribs on the respective rings. FIG. 7G2 shows the gasket-retaining or gasket-locating feature 690 having a further gasket retaining feature 690A locally projecting radially inward. FIG. 7H shows an assembly in which the movable ring 600 has gasket locators 692 that are intermittent and are localized ribs, and the wall 560 in the stationary ring 500 has interruptions suitable to accommodate the ribs or gasket locator features 692 when movable ring 600 closes onto stationary ring 500. There could be an interference fit or snug fit between gasket 200 and the retention ribs or gasket locating feature 692 on movable ring 600.

Figure 7I:
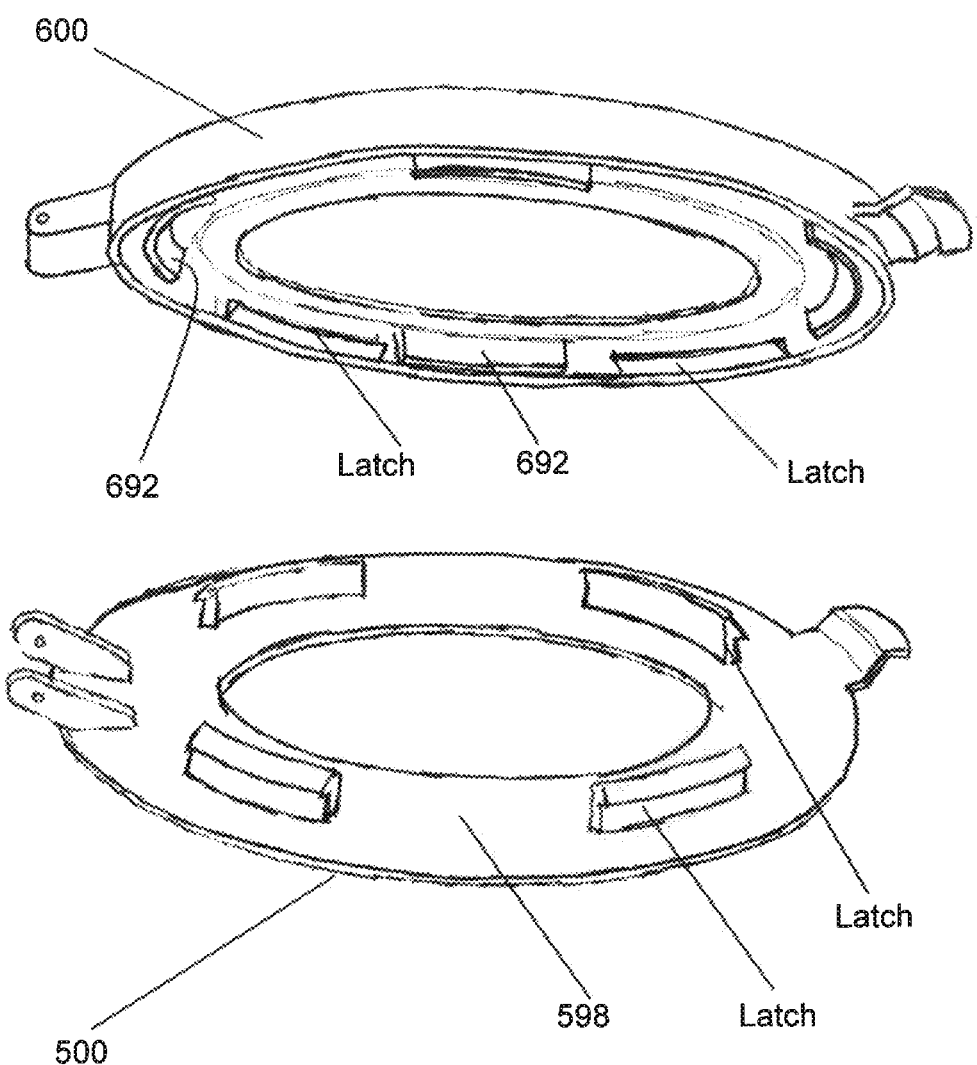
Figure 7J:
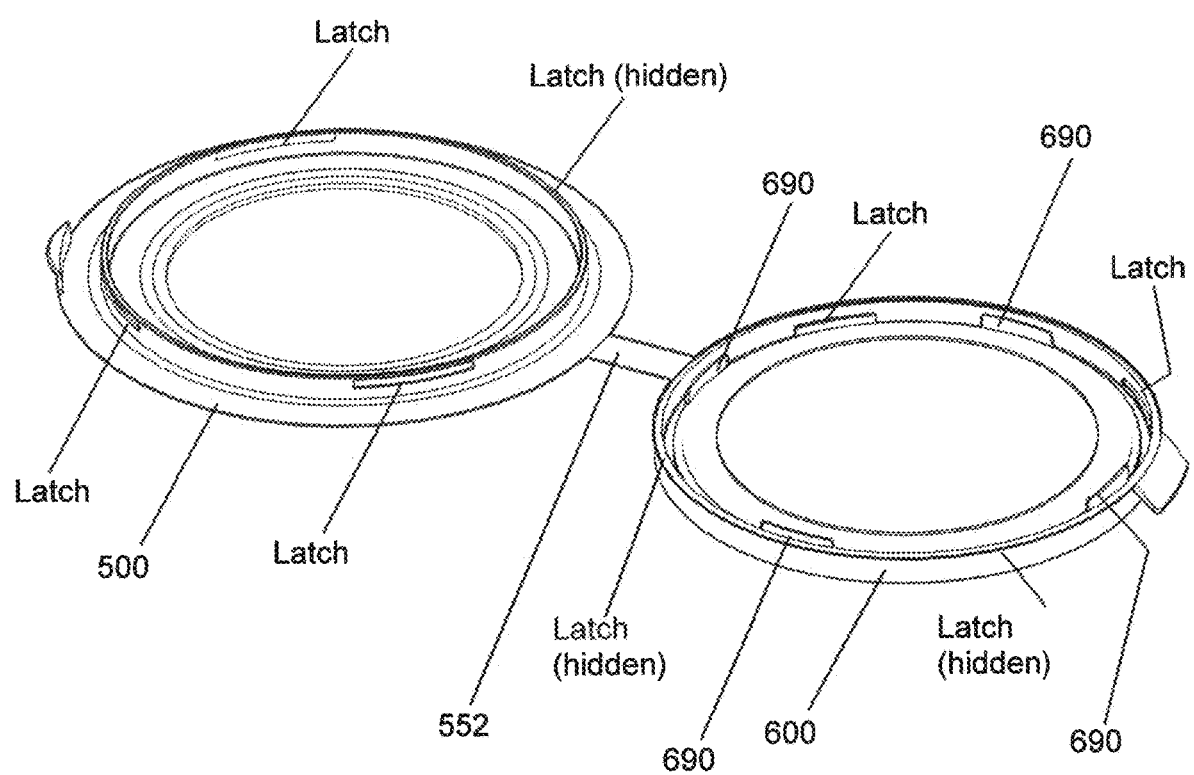

FIG. 7I shows an assembly (exploded) in which the movable ring intermittent gasket locating features 692 are an interrupted wall, and the wall in the stationary ring 500 has interruptions 598 suitable to accommodate the gasket locating features 692. Also shown in FIG. 7I are latch components on respective rings 500, 600.

FIG. 7J shows an assembly similar to FIGS. 7G and 7H but with a living hinge 552. In this illustration, the latch segments are at a larger radius than the gasket-locating segments. The latch segments are interspersed with the gasket-locating segments.

In embodiments of the invention, the gasket-locating feature 690 can have a rounded edge or corner (facing the stationary ring 500) to make it easier for the user to insert or introduce the gasket 200 into its installed position in movable ring 600. However, it would not be desirable for the rounded edge or corner to be too large, because space devoted to the rounded edge or corner is unavailable for frictional engagement with the outer edge of gasket 200

It is further possible that the gasket-locating feature 690 or 692 may also be a gasket-retaining feature such as to discourage the gasket 200 from falling or moving out of position in movable ring 600. For example, the gasket-retaining feature can also provide a snug fit with the exterior of the gasket 200 so as to grip or retain the gasket 200 during the swinging of the movable ring 600 from the open configuration to the closed configuration.

Dimensional Interrelationships

Certain dimensional relationships may exist for there to be a desired relationship between the movable ring 600 and the stationary ring 500 and gasket-locating feature 690 or 692 and features of the inner pouch 100 such as gasket 200.

In embodiments of the invention, certain dimensional relationships may exist between the gasket 200, the inner pouch 100 and components of the appliance 10 such as rings 500, 600. First of all, stationary ring 500 may have an inside dimension larger than the dimension of a stoma and suitable for the passage of waste material through the inside dimension of the stationary ring 500. Also, the movable ring 600 may have an inside dimension such that the elongated portion 110 of inner pouch 100, when inner pouch 100 is in an unfolded and empty configuration, may be suitable to pass through the central opening 610. At the same time, the inside dimension of movable ring 600 may be smaller than the largest dimension of the gasket 200, so that when gasket 200 is in a flat state gasket 200 is not able, or at least not easily able, to pass through movable ring 600 when it is initially installed in the movable ring 600. It is possible that both stationary ring 500 and movable ring 600 may be of or similar or even identical overall dimensions such as the diameters of the respective central openings 510, 610 therethrough, although this is not essential. Both stationary ring 500 and movable ring 600 may be generally axisymmetric in their overall features, as illustrated, although this is not essential.

Seating of Gasket in Movable Ring

Relevant components of the system may have dimensional relationships such that the interior surface (inside diameter) of gasket 200 is narrower than the inside diameter of the edge of the lip 650. This relationship ensures that the place where the hole through inner pouch proximal layer 120 and the hole in the interior of the gasket 200 will be able to exist in the interior of space defined by lip 650. This allows the gasket 200 to exist on the body-facing side of the movable ring 600 and allows the membrane of the inner pouch 100 to exist on the exterior side of movable ring 600 when the inner pouch 100 is in its installed position in movable ring 600.

The movable ring 600 may comprise a ring structure that extends completely around a perimeter of the movable ring 600, and movable ring 600 may comprise a deformable lip 650 connected to or integral with the ring structure of movable ring 600. Lip 650 is illustrated as being tapered, being thicker near where lip 650 joins the rest of movable ring 600, and thinner away from where lip 650 joins the rest of movable ring 600. Lip 650 may have a tip radius, which may be a bead, which may press against gasket 200 when the assembly is in the closed configuration.

The movable ring 600 may have a longitudinal axis 630 as illustrated in FIG. 3C, and some features of the movable ring 600 may be axisymmetric about the longitudinal axis 630. A plane of bending of lip 650 may be defined as including the longitudinal axis 630 of the movable ring 600. For bending of the lip 650 that occurs in that plane, the lip 650 may be more flexible than the circumferential ring structure to which it is connected or is integral with. For bending that occurs in a plane that contains a longitudinal axis 630 of the movable ring 600, the lip 650 can be more flexible than the rest of the structure of movable ring 600.

As shown in FIG. 7F (which is exploded by disassembling the hinge), it is illustrated that movable ring 600 can contain a gasket-locating wall 690. Gasket-locating wall 690 can also serve to retain gasket 200 when movable ring 600 and stationary ring 500 are in their open configuration with respect to each other. It is further illustrated that stationary ring 500 can contain a groove 572 so that gasket-locating wall 690 from movable ring 600 can, in the closed configuration, extend further along the direction of the thickness of the gasket 200 (the vertical direction as illustrated here) than would be possible without such groove 572. This gives more distance for engagement between gasket 200 and gasket-locating wall 690. This is relevant because the lip 650 is likely to deflect during closure, which means that without the extended length of wall 690 made possible by the presence of groove 572, there might be only a limited amount of space for wall 690 to engage with the thickness of gasket 200. Providing the groove 572 in stationary ring 500 provides more possible extent of wall 690 and therefore more possible engagement of wall 690 with gasket 200 along the edge or thickness dimension of gasket 200.

Relationship of Gasket to Wall on Stationary Ring

As illustrated in FIGS. 6A and 6B, the stationary ring 500 may have a wall 560. In embodiments of the invention, there can be various dimensional relationships between the exterior of gasket 200 and this wall 560 in stationary ring 500. As illustrated in the embodiment in FIGS. 6A-6B, the wall 560 of stationary ring 500 may have an inner surface that is a snug or nearly-snug fit with the outside of the gasket 200. Such a fit can help to locate gasket 200 with respect to various parts of the assembly. (It can be appreciated that this locating and fit only occurs when the movable ring 600 is in or near its closed configuration with respect to stationary ring 500. This locating function would not be available when movable ring 600 is swung away from stationary ring 500.) In fact, it is possible that the fit between gasket 200 and the wall 560 in stationary ring 500 can be more precise than the fit between the neck 182 of inner pouch 100 and movable ring central opening 610. However, if this just-described fit is excessively snug, it could complicate removing the gasket 200 and the inner pouch 100 from the stationary ring 500 when movable ring 600 is swung away from stationary ring 500. Thus, it may be desirable to dimension the respective parts so that the fit is not so snug as to create excessive friction between the gasket 200 and the wall 560 of stationary ring 500. Alternately, it would be possible for the fit between the gasket 200 and the wall in the stationary ring 500 to be a clearance (slightly loose) fit, and the inner surface of the wall 560 in the stationary ring 500 could have three or more ribs 568 spaced around the circumference of the wall 560, wherein an inscribed circle touching the inner walls of the ribs is slightly smaller than the outer diameter of the gasket. Such a geometry could retain the gasket 200 in place.

Seating of Gasket Outer Surface Against a Feature of the Movable Ring

In other embodiments of the invention, it is possible that the movable ring 600 comprises a gasket-locating feature 690 that has an inner surface that is close-fitting, in the radial direction, with respect to the outer perimeter of the gasket 200. In such a design, some other provision (not illustrated) could be made for where and how the latching occurs between the movable ring 600 and the stationary ring 500. FIG. 7E illustrates a snug fit between the exterior of the gasket 200 and an internal surface of gasket locating feature 690 of movable ring 600. The snug fit could serve both to locate the gasket 200 with respect to the movable ring 600 and also to retain the gasket 200 and inner pouch 100 while the movable ring 600 is being swung from the open configuration to the closed configuration. This close fit can be continuous around the perimeter of the gasket or can be intermittent around the perimeter of the gasket. This close or snug fit can provide both gasket locating and gasket retention.

Seating of Gasket Outer Surface Against a Dedicated Feature of the Movable Ring

FIGS. 7E and 7F show designs that provide dimensional registration and snugness using the outer surface of the gasket in combination with a wall 690. In either of these designs, what the patient sees when loading the gasket 200 and inner pouch 100 into the movable ring 600 would be completely axisymmetric and simple to look at. Also, the radial interference between the gasket 200 and the gasket-locating features 690 for locating the gasket 200 is from the exterior of the gasket 200. This minimizes opportunities for pockets of waste to become trapped.

In FIG. 7E, the gasket-locating feature 690 would engage with the gasket 200 only for a portion of the thickness of the gasket 200. The gasket 200 itself already may be fairly thin (such as 0.75 mm or about 1/32 of an inch), and therefore engaging with only a portion of the already-small thickness of the gasket 200 might not be as robust as might be desired in terms of practical usage. Therefore, another design detail, which is shown in FIG. 7F, is that the gasket-locating feature 690 from the movable ring 600 could extend downward a little bit further than the flexible lip 650 extends downward (in its undeformed condition). This is consistent with the purpose of the gasket-locating feature 690 to locate and hold the gasket 200 during swinging/closing of movable ring 600 toward stationary ring 500. In order to make this gasket engagement easier to happen and to allow the gasket-locating feature 690 to at least engage the entire thickness of the gasket 200 (rather than only a partial thickness), it would be possible to provide small recesses or a continuous groove 572 in the stationary ring 500 where the gasket-locating feature 690 would land. In FIG. 7F, a groove 572 is shown. This would make it possible for the gasket-locating feature 690 to be a little bit longer than it would be able to be in the absence of groove 572. Such extra length would improve engagement of the gasket-locating feature 690 with the gasket 200.

In a similar spirit, it would be possible to simply build up the thickness of the stationary ring 500 (around the entire circumference of the stationary ring 500) where useful such as near the radial location of the lip 650, and to avoid building up the thickness of the stationary ring 500 at radial dimensions where that build-up would be undesired for the gasket-locating feature 690 to be able to land. In yet another embodiment there could be a slight clearance between the bottom surface of the gasket retaining feature 690 in the movable ring 600 and the seating surface 540 of the stationary ring 500. The seating surface of the stationary ring 500 that contacts the proximal surface of the gasket 200 could further comprise a distally-projecting rib or bump 594 extending around the circumference. The dimensions of the rib or bump 594 could be sized to interact with the flexible lip 650 on the movable ring 600 to form a seal with the gasket 200. In still other embodiments, there may be more than one bump 594 projecting distally from the surface of the stationary ring 500, such as at different radial locations.

In still other embodiments, as illustrated in FIGS. 6C-6D, the flexible element or lip could be located on the stationary ring 500 and the rigid element of the gasket seal could be located on the movable ring 600. In such an embodiment, the flexible seal element could be raised or angled away from the surface of the ostomy wafer to allow for movement of the flexible element or lip. In such an embodiment, as shown in FIG. 6D, the tip of the flexible element could comprise a bead 556, rounded in cross section such as approximately twice in cross sectional dimension compared to the thickness of the nearby tip, to prevent possible trauma to stoma tissue upon repeated contact with the flexible element.

It can be kept in mind that many of these features discussed here, especially features of the movable ring 600, will be outside the fluid seal/containment boundary, because upon closure of the rings 500, 600, that boundary of the interior of inner pouch 100 is defined by where the lip 650 presses on the gasket 200.

As illustrated in FIG. 7H and FIG. 7I, it is possible that gasket-locating features 690 on the movable ring 600 could be interspersed (in angular location) with features on the stationary ring 500 that participate in the latching. The inner surface of the gasket-locating features on the movable ring 600 could have the same radial dimension as the features on the stationary ring 500 that participate in the latching, or alternatively these features could have different radial dimensions. For example, the gasket-locating features 690 could be snug with the outer surface of the gasket 200 while the features on the stationary ring 500 that participate in the latching might not interact with the outer surface of the gasket 200. It is also possible that gasket-locating features in movable ring 600 could be ribs.

In an embodiment of the invention, the movable ring 600 and the stationary ring 500 can have complementary features, one of them convex and the other concave, that may locally deform the gasket 200. One of those features can be male and the other can be female, such as a bump and a corresponding depression. These features could be thought of as corrugations (either single or multiple). In an embodiment of the invention, there could be provided corrugation such as multiple concentric grooves or ridges (some more radially inward, others more radially outward) extending substantially all the way around the circumference of either or both of the stationary ring 500 and the movable ring 600. These multiple features such as grooves or ridges could in effect provide multiple seals in succession, thereby improving the overall quality of sealing.

Stiffness or Flexibility of Stationary Ring and Movable Ring for Out-of-Plane Bending The stationary ring 500 and the movable ring 600 may be considered to be at least approximately planar, in their relaxed or undeformed state. A relevant design parameter is how stiff or flexible the stationary ring 500 and the movable ring 600 are in terms of out-of-plane bending. This is relevant when an appliance of an embodiment of the invention is attached to the patient, and if the patient bends or moves or even if the patient's abdomen expands and contracts during breathing. If the stationary ring 500 is substantially stiff, or the stationary ring 500 and the movable ring 600 together are fairly stiff, the patient's movements might be hindered by it and the patient might perhaps be bothered by it, such as when the patient's abdomen moves. On the other hand, if the stationary ring 500 and the movable ring 600 have some flexibility, the stationary ring 500 and the movable ring 600 might bend at least somewhat when the patient's abdomen moves or changes shape. This could improve comfort for the patient, in comparison to a stationary ring 500 and movable ring 600 that are quite rigid. The stiffnesses of these two rings 500, 600 for out-of-plane bending is influenced by the dimensions of the rings 500, 600 and by the mechanical properties of the materials of which they are made.

In a situation of somewhat flexible stationary ring 500 and movable ring 600 which undergo out-of-plane bending while latched together, the lip 650 could still exert pressure on the gasket 200 but the lip 650 would have to accommodate the described bending along the length of lip 650 while latched.

Figure 7K:
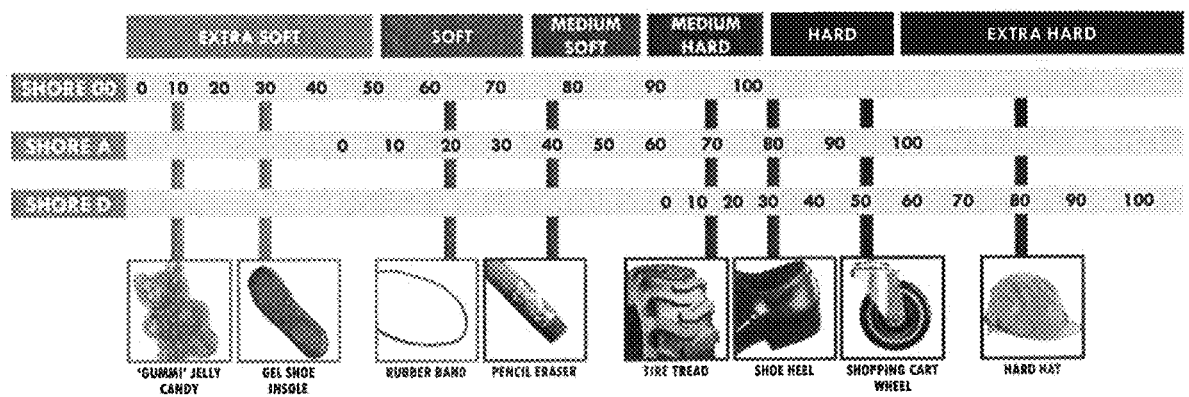

Description of softness or hardness of rubbers and other polymeric materials is given in FIG. 7K (which is taken from https://www.smooth-on.com/page/durometer-shore-hardness-scale/). In an embodiment of the invention in which it is desired that the rings 500, 600 should at least somewhat bend with the patient's motions, the material of which the stationary ring 500 and movable ring 600 are made can have a durometer of approximately Shore A30 or softer. If such bending is not desired, the material of which the stationary ring 500 and movable ring 600 are made can have a durometer of between approximately Shore A30 and Shore A60.

The stiffness of the stationary ring 500 and the movable ring 600 for out-of-plane bending may influence the design of the latch between the movable ring 600 and the stationary ring 500. It is possible that in a flexible design it might be less useful to use discrete latch mechanisms as have already been described herein, because the relative location of and between the discrete latch components as previously described could become more uncertain during bending, and such change of location could possibly cause unlatching. Instead, in the situation of somewhat flexible rings 500, 600 it might be desirable to use a latching feature between the two rings 500, 600 that is more continuous along the circumference of the rings 500, 600. For example, such a latching feature could extend continuously around the circumference of rings 500, 600, or continuously around a majority of the circumference, such as continuously except near hinge 550.

Figure 7L:
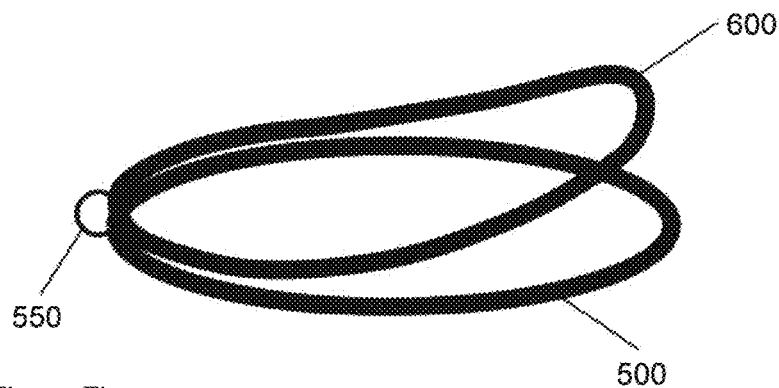
Figure 7M:
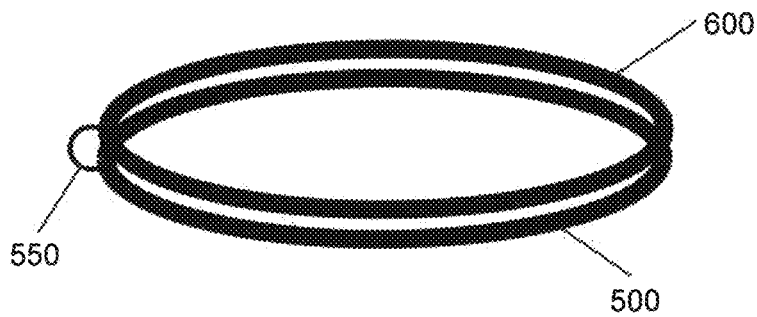

Embodiments of the invention herein have illustrated the stationary ring 500 and the movable ring 600 as being substantially planar in their overall shape and in the shapes that interact with each other, and it is illustrated that during the process of closing the movable ring 600 to the stationary ring 500, the overall ring shape of the stationary ring 500 and the movable ring 600 do not undergo any significant change of shape such as overall bending of the ring shape. However, other designs are also possible. It is possible that movable ring 600 could have a natural shape and that in order to complete its engagement with stationary ring 500, movable ring 600 would have to undergo some overall bending into a shape that is different from its natural shape. This would be especially applicable if the hinge 550 is a joint that rotates around a hinge pin. For example, referring ow to FIGS. 7L and 7M, it is possible that, if the stationary ring 500 and movable ring 600 are viewed from the side such as 90 degrees away (around axis 630) from hinge 550, stationary ring 500 may be flat, and movable ring 600 in its natural shape could be curved, and movable ring 600 when engaged with stationary ring 500 would be bent out of its natural shape into a flat shape. The natural curvature of movable ring 600 could be such that in the unlatched condition, even if movable ring 600 is in contact with stationary ring 500 at a place near hinge 550, if one starts at the hinge 550 and proceeds away from the hinge 550, the distance between the rings 600, 500 increases due to the natural curvature of movable ring 600 away from stationary ring 500. In order to complete the engagement of movable ring 600 with stationary ring 500, it would be necessary to unbend movable ring 600, followed by latching of movable ring 600 and stationary ring 500 with each other. Such a situation could help to provide consistent pressure of lip 650 or any other feature of movable ring 600, on gasket 200, for purposes of establishing a seal. This is illustrated schematically in FIGS. 7L and 7M, using schematic versions of stationary ring 500, movable ring 600 and hinge 550. FIG. 7L shows a situation in which movable ring 600 is disengaged from stationary ring 500 although being close to the engaged position. Stationary ring 500 is generally flat or planar, and movable ring 600 is shown in its natural shape as being curved in an out-of-plane manner. FIG. 7M shows the corresponding engaged position, in which movable ring 600 is bent out of its natural shape into a planar shape to achieve engagement with stationary ring 500. For purposes of this illustration it can be assumed that stationary ring 500 is sufficiently stiff to not significantly bend, in comparison to the bending of movable ring 600. Variations of this principle are also possible, involving other shapes and other amounts of bending of either or both of the rings 500, 600.

Exit of Gas Through Features of Inner Pouch

In embodiments of the invention, the inner pouch 100 may comprise an inner pouch proximal layer 120 and an inner pouch distal layer 130 that may be joined to each other at an edge, such as by thermal welding or alternatively by adhesive or other method. In some embodiments of the invention, the joint may form a fully continuous perimeter around or near the exterior of the inner pouch 100.

In general, it is desirable to provide some provision for exit of flatus gas from the interior of inner pouch 100. Accordingly, in an embodiment of the invention, as illustrated in FIG. 8A, it may be provided that the joint around the edge of inner pouch 100 may be continuous around a vast majority of the perimeter of the inner pouch 100, but may have a slight interruption. The slight interruption may provide an exit path for flatus gas to exit from the inner pouch 100. It is further possible that in this slight interruption may be provided in the form of a tortuous path 182. The presence of the tortuous path 182 may help to retain any liquid or solid waste matter that may be present inside the inner pouch 100. This is especially true if the tortuous path 182 contains some changes of direction that proceed downward followed by upward when the patient is in a typical upright position. It may also be provided that there is more than one such tortuous path 182, with such tortuous paths 182 being located at different positions around the perimeter of the inner pouch 100. In such a situation, it could be provided that different tortuous paths 182 could be located at different elevations or different angular positions around the inner pouch 100 so that if liquid is present inside the inner pouch 100 (as is commonly the case for ileostomy patients), for a variety of positions of the patient's body there would still be at least one tortuous path 182 that is at a relatively high elevation and likely to permit the flow of flatus gas. The dimensions of the tortuous path 182 could be chosen to be sufficiently small as to discourage the flow of liquid through them.

An alternate embodiment of an exit path is shown in a different part of FIG. 8A and also in FIG. 8B. In this embodiment, the joint around the inner pouch 100 may be completely continuous, and the exit path for gas from within the inner pouch 100 could be through one or more small holes 186 created in one or both film layers 120, 130 of inner pouch 100. The holes 186 may typically be generated by mechanically piercing one or both layers of the inner pouch 100, although alternate means, such as laser cutting, could be employed. Such exit holes 186 could be in series with a tortuous path, which could be produced, as described herein, in connection with the perimeter joint or weld of the inner pouch 100.

Yet another alternative for exit of flatus gas is that it is possible to design a feature in the gasket/lip interaction that amounts to a tortuous path or deliberate leak for gas exit while maintaining a seal against the solid and liquid components of stool. Embodiments are illustrated in FIG. 8C-8F.

As illustrated in FIG. 8C, it is possible that the lip 650 could be interrupted in isolated places so that in those isolated places there is not pressure on gasket 200 as effectively as is provided by lip 650 in most other places. Such interruptions could be small in their extent in the circumferential direction, such as less than the thickness of the gasket 200. Lip 650 is illustrated as being continuous around the circumference of movable ring 600. Such continuity is believed to be useful and a good practice for establishing the desired seal against leakage of solid stool or the fluid component of stool. Nevertheless, it is possible that the lip 650 might be interrupted by some very thin slits and it might still produce a useful seal. For example, if the lip 650 contained slits that were thinner than the gasket material thickness, there might still be achieved a seal that is reasonable for present purposes. If the slits were relatively larger, they might weaken the seal in isolated places so as to allow passage of flatus gas.

As illustrated in FIG. 8D, a further possibility is that the seating surface 540 of stationary ring 500 could contain one or more small grooves 542. Such grooves 542 could be permanent features of stationary ring 500, such as being made by molding at the same time as the rest of stationary ring 500 is molded. Such grooves 542 could be tortuous in shape. There could be several such grooves created in the stationary ring 500. Placement of such grooves 542 would be most effective when placed at points on the stationary ring 500 where the solid and liquid components of stool are less likely to collect, such as the upper portion of the stationary ring 500 and movable ring 600 (when the patient is upright), which could be approximately 180 degrees away from the location of the hinge 550.

As illustrated in FIG. 8E, such a function may be achieved by features such as a recess or groove 222 in the surface of gasket 200. The recess or groove 222 may extend from an inner perimeter of gasket 200 to an outer perimeter of gasket 200.

In another embodiment, such tortuous paths 222 can be embossed in the mating surface of the gasket 200. In another alternate embodiment, such tortuous paths may be defined by the application of a substance with higher rigidity than the gasket material to prevent occlusion of the tortuous path when the gasket 200 is clamped between movable ring 600 and stationary ring 500. In one embodiment, the substance can be a plastic film applied in a pattern. In another embodiment, the substance could be a hot melt adhesive. In still other embodiments, the substance could be spray-coated through a mask or in a controlled means of controlled droplet deposition similar to ink-jet printing. The gasket 200 could be more rigid away from the tortuous path than it is where the tortuous path is located.

As yet another example, it is possible that the gasket 200 could have an interruption in the form of a slight gap going from its interior to its exterior, as a passageway for gas. Such a gap could be created in the proximal surface of the gasket 200 by means of coining during die-cutting of the gasket, or by means of a partial cut if the gasket 200 is laser cut. It is also possible that a small passageway could be molded into the lip 650 or some other part that contacts the gasket 200 and is involved in the seal, so as to provide a passageway for gas. For example, such passageways can be small in cross section, ranging from an edge-to-edge distance of 0.1 mm to 1 mm so as to allow flatus gas to escape through them but not liquid.

It is further possible that gasket 200 could be less than a full complete ring. Gasket 200 could have a small gap connecting the interior of the gasket 200 with the exterior of the gasket 200. Such gap could serve as a passageway for passage of gas such as flatus gas. The gasket 200 would still maintain contact with inner pouch 100, which would help to maintain the overall shape and dimensions of gasket 200. Such a situation is included in the meaning of gasket.

As illustrated in FIG. 8F, yet another possibility is that pinholes 652 could be provided in lip 650, with such pinholes 652 being used in conjunction with any of the other embodiments or features.

Blister or Pleat in Outer Pouch

Figure 9A:
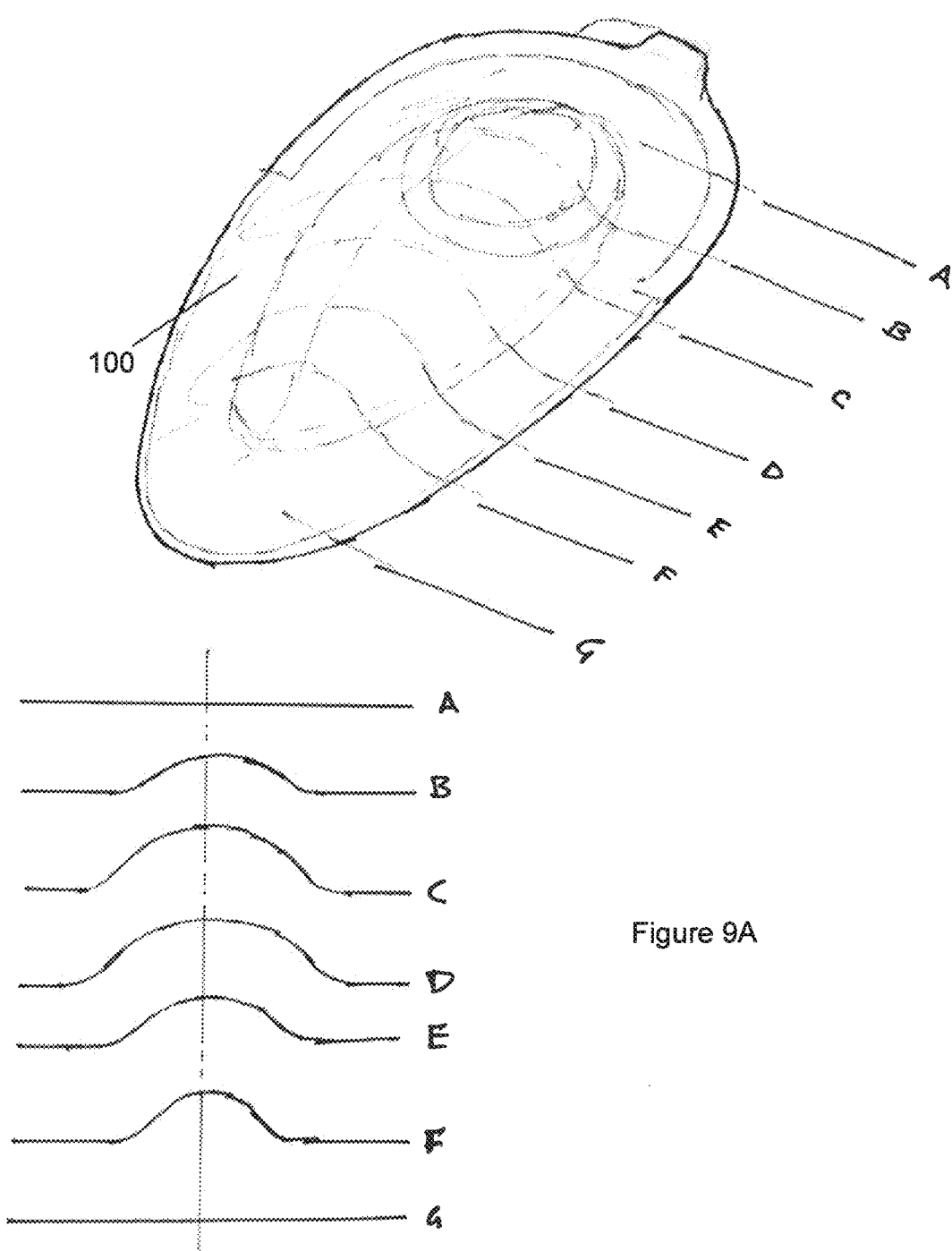
FIG. 9A shows an outer pouch with a blister to accommodate expansion of the inner pouch as it fills with waste.
Figure 9B:
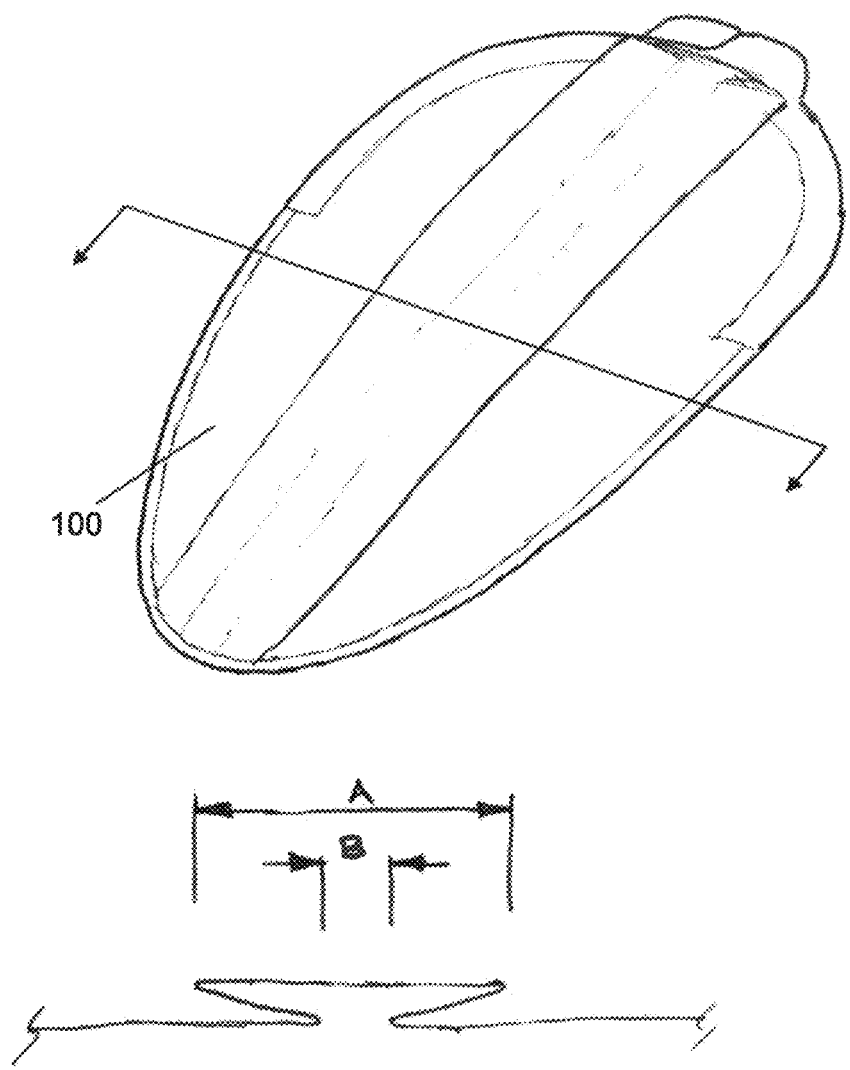
FIG. 9B shows an outer pouch with a pleat for expansion.

Reference is now made to FIGS. 9A-9B illustrating outer pouch 300. In an embodiment of the invention, the outer pouch 300 may have an outer surface (away from the patient's body) that comprises a blister 360. The blister 360 may be capable of having an outwardly bulged configuration at least when needed to permit the passage of waste material into or storage of waste material in inner pouch 100. Whether the blister 360 has an outwardly bulged configuration at other times is optional. The blister 360 may be sufficiently flexible that it can be crushed or compacted, such as by the user's clothing, if the space inside blister 360 is not needed FIG. 9A illustrates an outer pouch 300 containing thereon a blister 360. In FIG. 9A, for the situation in which blister 360 is in its outwardly-bulged configuration, there are illustrated various sections through outer pouch 300. The sections are taken in a generally horizontal plane (with respect to a patient who is considered to be in an upright orientation). The sectioning plane could be approximately a transverse or horizontal section according to standard anatomical terminology. In a section taken below the blister 360, such as section G, there is a shape of the outer surface of the outer pouch 300 in which there is little or no bulging out. In intermediate sections taken in the region of the blister 360, such as sections B-F, there is a possible shape that includes a bulging-out of the blister 360. In a section taken at a still higher elevation, such as section A, there is a shape that has little or no bulging-out compared to the shape taken at the intermediate sections.

It is possible that when the blister 360 is in the not-bulged configuration, the blister 360 may have a shape that is somewhat buckled, and that shape may be somewhat unpredictable or random depending on the details of the buckling, the details of the patient's clothing, or other factors.

Blister 360 may be made of the same material as nearby portions of outer pouch 300. In such case, the outer pouch distal layer 324 may have the blister 360 formed in it, such as by thermoforming. Alternatively, blister 360 could be made of a different material. In such case, the blister 360 may be formed from a separate piece of film and bonded to the outer pouch distal layer 324 in a separate operation.

In regard to the rigidity of the blister 360, the blister 360 may be sufficiently rigid that it maintains its outward bulge in most normal conditions of wearing and usage. Alternatively, it is possible that the blister is sufficiently flexible that in many normal conditions of wearing and usage, the blister may be collapsed or partially collapsed or buckled, so that the appliance 10 is relatively flat in that situation, but blister 360 still may be able to bulge outward when necessary to permit the passage of waste past the blister 360 or to aid in the storage of waste within the inner pouch 100. It also is possible that the blister 360 could participate in the bending that occurs when outer pouch distal layer 324 is opened at purse handle segments 310A, 310B for accessing inner pouch 100. For this purpose, the flexibility properties of blister 360 may be appropriate to easily allow the bending of outer pouch distal layer 324 that is involved in opening outer pouch 300. Depending on what is desired, the blister 360 may have the same or similar rigidity or flexibility as the nearby material of outer pouch 300, or alternatively it could have a different rigidity or flexibility. For example, the blister may have a bending stiffness that is between 50% and 200% of a bending stiffness of the outer pouch proximal layer 322. Such rigidity or flexibility can be a function of material properties, thickness of material, and other geometric details. The blister 360 could comprise either the same material as nearby portions of outer pouch 300, or a different material.

As an example, regarding dimensions of the blister 360, the blister 360 could have a lengthwise extent that is less than 90% or less than 80%, of an overall lengthwise extent of the outer pouch 300. The blister 360 could have a width extent that is less than 90%, or less than 80%, of an overall width of the outer pouch 300. The blister 360 could have a depth (bulge dimension of the blister 360, i.e., outward protrusion, in a proximal-distal direction, compared to an unblistered surface) that is less than 2 inches (51 mm). Such a design would provide useful space for passing or storing waste matter.

In yet another embodiment of the invention, the outer pouch 300 may have a pleat 370 that is able to change its shape by bending at defined creases or folds so as to provide some ability for outer pouch 300 to expand when needed. Such a pleat 370 is illustrated in FIG. 9B. The pleat 370 is illustrated in a compact configuration in which its dimension and the dimension of outer pouch 300, in the proximal-distal direction, is relatively small. The pleat 370 may have an expanded configuration in which its dimension in the proximal-distal direction is greater than for its compact configuration. As illustrated, the pleat 370 may include four folds, of which two folds are concave or interior-facing and two are convex or exterior-facing.

In FIG. 9B, Dimension "A" and Dimension "B" are labeled. Dimension "A" (the larger dimension of the pleat 370) may have a value that is approximately 0.3 times the width of the outer pouch 300 (at the maximum width of outer pouch 300 or the location at which dimension "A" is measured). More generally this dimension "A" may range from 0.2 to 0.6 times the width of the outer pouch 300. Dimension "B" (the smaller or opening dimension of the pleat 370) may have a value that is approximately 0.2 times the width of the outer pouch 300 (at the maximum width of outer pouch 300 or the location at which dimension "B" is measured). More generally this dimension "B" may range from 0.1 to 0.4 times the width of the outer pouch 300.

The pleat 370, in cross-section, is shown as being symmetrical about the midline of outer pouch 300, and is shown as having constant dimensions along its length. However, alternate embodiments could be asymmetrical, with the pleat on one side of the midline being different from the pleat on the opposite side of the midline, or with a pleat on only one side and not the other. In still other embodiments, the dimensions of the pleat 370 could change along the lengthwise direction of the pleat 370 to create a pleat that is tapered.

Storage Region for Additional Inner Pouches

Figure 10A:
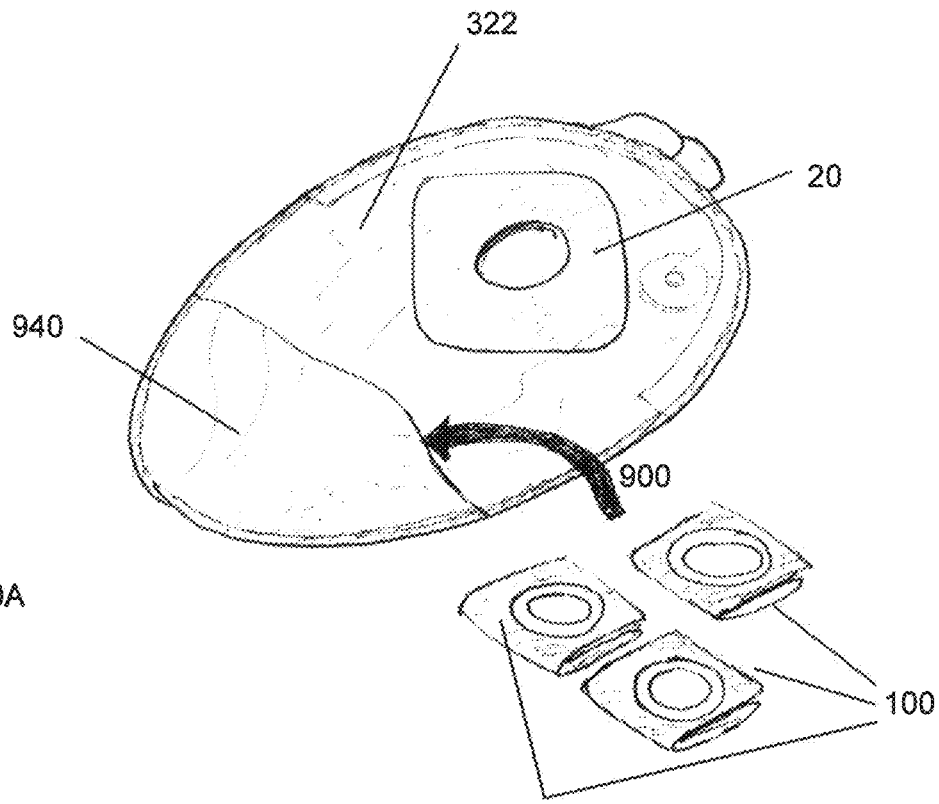
FIG. 10A shows an outer pouch having a storage region.
Figure 10B:
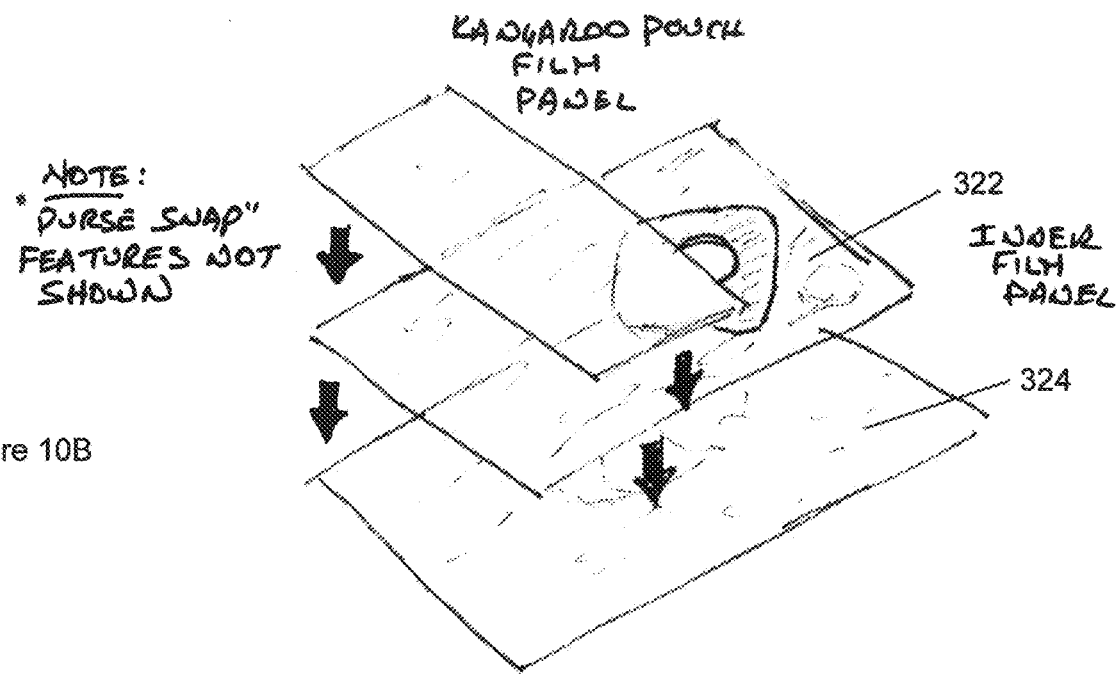
FIG. 10B is an exploded view showing construction of such an outer pouch and storage region.

In an embodiment of the invention, it is further possible that the appliance 10 may comprise a storage region 900, which may be suitable for storing extra unused inner pouches 100. This may be a convenience feature for the user. The storage region 900 may comprise an extra layer of material, which may be the same material of which other parts of the appliance 10 are made. This is illustrated in FIGS. 10A and 10B.

The storage region 900 may be located either on an exterior surface of one of the layers of the outer pouch 300, or on an interior surface of one of the layers of the outer pouch 300, so that the storage region 900 may be outside or inside appliance 10, as desired. If the storage region is interior, the outer pouch 300 may have within it enough space to contain a full inner pouch 100 and additionally enough space to contain several empty unused inner pouches 100, which may be in a folded or compact or empty condition. What is illustrated and currently preferred is the storage region 900 being on the exterior. As illustrated here, the storage pouch 900 is on the exterior of outer pouch 300, and it is located on the proximal side of outer pouch 300, i.e., between outer pouch 300 and the user's abdomen. This choice of storage location would avoid creating possible complications with respect to the storage pouch and the blister 360 or pleats 370 that might be located on the distal side of outer pouch 300, as well as possible interference with the opening of purse handle segments 310A or 310B.

The extra layer of material 940 may, for example, have four edges, such as a rectangular shape. Of these edges, three of these edges may be attached to the outer pouch 300 while the fourth edge may remain unattached to provide an opening for inserting or removing stored items into or from the storage region 900. As illustrated, the storage region 900 might be non-rectangular and some edges of the storage region 900 may coincide with edges of the outer pouch 300. Furthermore, if desired, there may also be provided a closure flap (not illustrated) associated with the storage region. The closure flap may be flexible so as to either cover or expose the entrance to the storage region 900. If desired, attachment means may be provided for releasably attaching the closure flap to the extra layer of material 940 that forms the storage region.

Filtration of Gas

Figure 11:
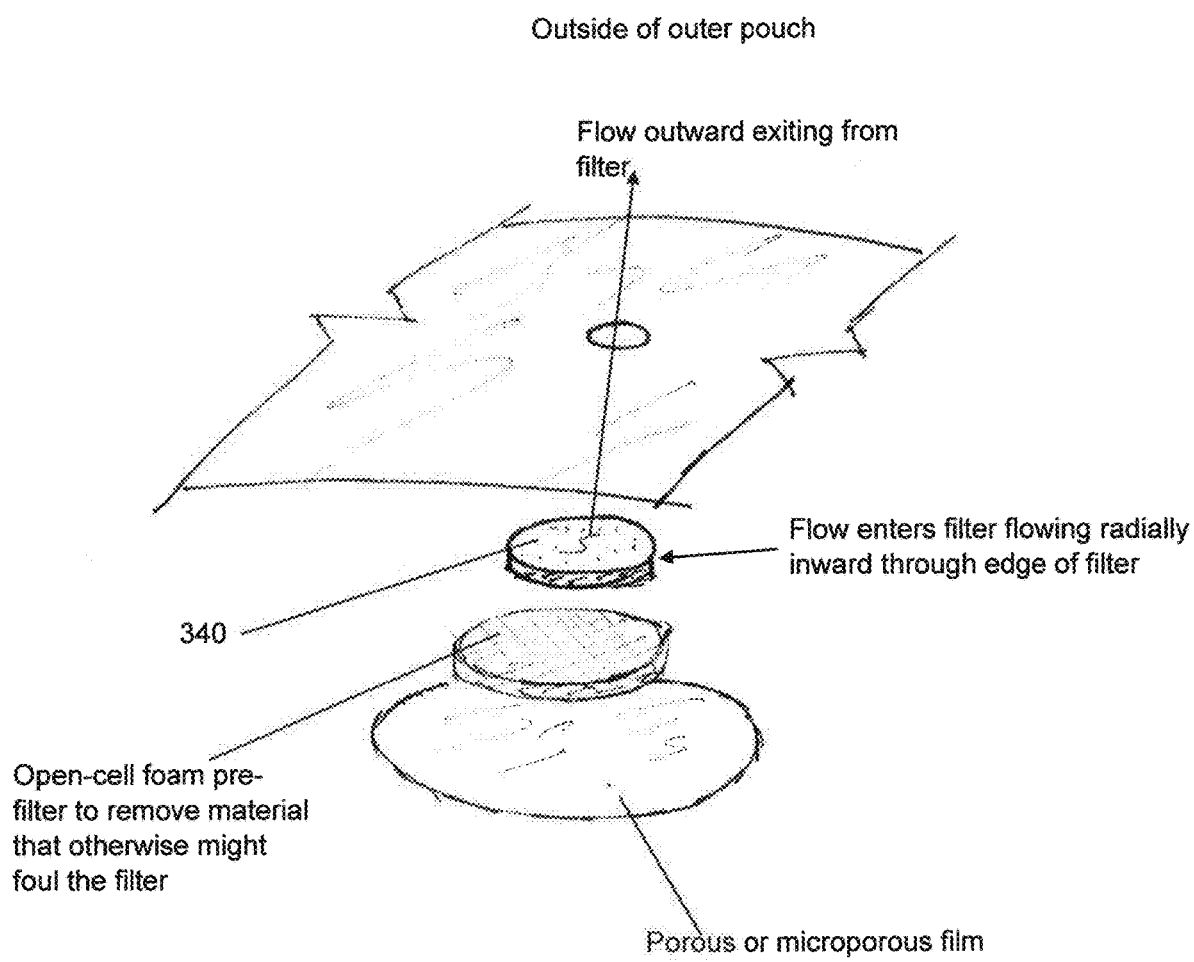
FIG. 11 shows a filter that may be part of an outer pouch.

As described elsewhere herein, in an embodiment, the inner pouch 100 may comprise a vent and tortuous path for release of accumulated flatus gas from the inner pouch 100. In an embodiment of the outer pouch 300, gas released from the inner pouch 100 may, in turn, be released through venting means in the outer pouch 300. Referring now to FIG. 11, the vent could comprise a filter 340. The filter 340 could comprise an activated charcoal filtration means. The filter 340 could be bonded to the pouch film by heat welding or adhesive bonding, and gas expelled from the filter 340 would vent through a hole in the outer pouch film. The filter 340 would be attached to either the outer pouch proximal layer 322 or the outer pouch distal layer 324 of the outer pouch 300.

In an embodiment, the filter 340 may be protected by pre-filtration means comprising one or more of open cell foam, perforated film, or a separate film panel welded or bonded to the pouch film wherein the pattern of welding or bonding comprises a tortuous path to the filter 340.

Thus, the complete filtration path could comprise: a perforated film panel that serves to further separate out liquid and solid phases of stool before any material reaches the pre-filter, a pre-filter comprising an open cell foam or plastic mesh; and the filter 340 such as an activated charcoal filer. The perforated film panel can be significantly larger in area than the prefilter, so that it can be bonded to the surface of the film of outer pouch 300, thereby trapping the prefilter in place between the perforated film and charcoal filter. The filter 340, or the filter subassembly, may be attached to an internal surface of the outer pouch 300, although it would also be possible for the filter 340 to be mounted to an external surface of the outer pouch 300.

Coupling Between Wafer Assembly and Appliance

Another aspect of an ostomy system of an embodiment of the invention is the wafer that joins the ostomy system to the patient's skin. In an embodiment of the invention, there may be provided a wafer assembly 1500, with the wafer assembly 1500 being joinable to and separable from the remainder of appliance 10. In such an embodiment, the wafer assembly 1500 may have a wafer coupling 1550 and the patient-facing aide of appliance 10 may have an appliance coupling 1600, and the wafer coupling 1550 and the appliance coupling 1600 may be engageable with each other. It can be understood that what is engageable with the wafer assembly 1500 is the entire appliance 10 (rather than simply a pouch as is the case in some known devices), and furthermore the appliance 10 can, as described elsewhere herein, replaceably accept an inner pouch 100 within the appliance 10. In such a system, it is possible to remove the appliance 10 from the patient's body while leaving the wafer assembly 1500 attached to the patient's body. Thus, it is possible to change or replace the appliance 10 without replacing the wafer assembly 1500, and it is possible to remove and replace inner pouch 100 within appliance 10. Thus, the timing and frequency of replacement of each of those respective items could be different from each other.

Such a system is illustrated in FIGS. 12A-12D. In these illustrations, the outer pouch is omitted for clarity of illustration. FIG. 12A is an exploded view, from the body-facing side, of the wafer assembly 1500 and the combination of stationary ring 500 and movable ring 600 hingedly joined to each other. FIG. 12B is a similar view, from a vantage point away from the user's body. FIG. 12C is a cross-section of FIG. 12B. FIG. 12D is a close-up of the wafer assembly 1500 in cross-section. FIG. 12E is a sketch of the wafer assembly and the appliance about to be assembled to each other, with the outer pouch distal panel being shown semi-transparent.

In an embodiment, the adhesive wafer 20 may be made of hydrocolloid adhesive with a cover layer of low density polyethylene film laminated to its exposed side. The adhesive may be a hydrocolloid adhesive, an acrylic adhesive, a combination of hydrocolloid sections and acrylic sections, or other adhesives typically used in attachment of ostomy appliances. The cover layer or film may range in thickness from 0.0005 inch to 0.015 inch. Such film may comprise a smooth surface or may be embossed. Such film may function to protect the appliance 10 and the ostomate from unwanted contact with the adhesive. Attachment means can include, but are not limited to, ultrasonic welding, heat welding, laser welding, adhesive bonding, or pressure-sensitive adhesives.

Still other embodiments may comprise a central section of hydrocolloid adhesive surrounding the stoma, wherein attached to and surrounding the hydrocolloid central section is a collar which may comprise a nonwoven fabric comprising an adhesive layer, wherein the adhesive layer may be acrylic pressure-sensitive adhesive, a thinner and more flexible hydrocolloid adhesive, a urethane adhesive, or a silicone adhesive.

In an embodiment, the system may comprise two separate couplings, i.e., a first coupling for removably securing the inner pouch 100 in its local place of installation (referring to the stationary ring 500 and the moveable ring 600), and a second coupling for removably attaching the outer pouch 300 to the adhesive wafer 20. The second coupling would typically be larger in diameter than the first coupling. In practice, the adhesive wafer 20 would be attached to the ostomate's peristomal area, with the moveable ring 600 and the stationary ring 500 in a closed configuration. After the outer pouch 300 is secured to the adhesive wafer 20 by means of the second coupling, the ostomate can open the outer pouch 300, open the movable ring 600 from the stationary ring 500, and insert the inner pouch 100 as described elsewhere herein. The options for design of the second coupling are similar to those for the first coupling with respect to latch configuration and materials. Exceptions, however, would be the absence of a hinge or strap, because the two coupling halves would be separate components, and the absence of a gasket, because the two coupling halves would seal directly against each other.

Referring to the wafer assembly 1500, as shown in FIG. 12D, wafer assembly 1500 may comprise an adhesive layer 1510, and a film layer 1520 adjacent to the adhesive layer 1510. There may be a central hole through the adhesive layer 1510 and the film layer 1520. As illustrated, the diameters of these holes do not have to be equal to each other. These diameters can be sized according to the dimensions of a patient's stoma. In FIGS. 12A-12D, it is illustrated that the adhesive layer 1510 and the film layer 1520 can have an external shape that is a square with rounded corners. Of course, other shapes are also possible.

In FIGS. 12A-12C, it is shown that stationary ring 500 can have, on its body-facing side, appliance coupling 1600. Appliance coupling 1600 may be continuous in a circular path around the circumference of stationary ring 500 on the proximal (patient-facing) side of stationary ring 500, although it can be understood that other shapes are also possible. In FIG. 12C, it is shown that appliance coupling 1600 has a cross-sectional shape that is in the shape of a groove.

Wafer assembly may further comprise wafer coupling 1550, which may be adjacent to or attached to film layer 1520. Wafer coupling 1550 may be continuous in a circular path around the circumference of wafer assembly 1500, similar to the nature of appliance coupling 1600, although it can be understood that other shapes are also possible. The dimensions of appliance coupling 1600 and wafer coupling 1550 may be such that appliance coupling 1600 and wafer coupling 1550 can engage with each other. The engagement may be robust but removable.

As mentioned, appliance coupling 1600 may have a cross-sectional shape that is in the shape of a groove 1610. Wafer coupling 1550 may have a cross-sectional shape that is in the shape of a projection that is engageable with the groove 1610 in appliance coupling 1600. The projection may have a wall 1560 and may have a lip 1570 that extends away from the wall 1560. Lip 1570 may be curved and may be tapered in a direction extending away from the wall. Lip 1570 may be deformable so as to create frictional engagement with appliance coupling 1600. It is possible, as illustrated, that during engagement, the wall 1560 of the projection bears against one side of the groove 1610 in appliance coupling 1600 while lip 1570 bears against another side of the groove 1610. The frictional engagement may be such that the engagement resists accidental dislodgement to a desired extent, yet also is sufficient to create engagement when desired and also is sufficiently easy to disengage when desired. The elasticity and material properties of appliance coupling 1600 and of wafer coupling 1550 may be chosen to facilitate these engagement characteristics. These elasticity and material properties could be either the same as each other or different. The materials of which the appliance coupling 1600 and the wafer coupling 1550 are made could be either the same as each other or different. As discussed elsewhere herein in connection with other components, an appliance coupling 1600 and wafer coupling 1550 that are somewhat rigid may serve to stabilize the peristomal skin around the stoma, thereby extending the wear time of the appliance 10. Such may be desirable for ostomates with little or no abdominal muscle tone or who have hernias. In other situations, a more flexible material for appliance coupling 1600 and wafer coupling 1550 may allow more freedom of movement and greater comfort for the ostomate.

It can be understood that the positions of groove and projection could be reversed, i.e., either the groove or the projection could be on the wafer coupling 1550 and the opposite could be on the appliance coupling 1600. Other geometric designs are also possible.

Methods of Use

With reference now to FIGS. 13A-13F, an embodiment of the invention can comprise a method of use of the described apparatus. In such a method, the user can start with the appliance 10, which for purpose of this description can be assumed not to contain an inner pouch initially. The user can apply the appliance 10 around the stoma and to the peristomal skin by means of an attached adhesive wafer, as illustrated in FIG. 13A. The attachment could be using a one-time adhesive, as illustrated, or alternatively could be made involving a reusable joint as discussed in connection with FIGS. 12A-12D. After the appliance 10 is secured to the user's body, the user can open one of the purse handle segments 310A, 310B, if it is not already open, and can introduce the inner pouch 100, as shown in FIG. 13B. The user can then swing the movable ring 600 away from the stationary ring 500 as shown in FIG. 13C. In a typical installation, the hinge 550 could be at a low point (when the patient is in an upright position), such that the movable ring 600 swings generally downward upon opening. However, other orientations are also possible. The swinging action could be free-swinging or it could be limited by either a stop or a detent, as described elsewhere herein. Upon opening the movable ring 600 as described, the movable ring 600 can be oriented somewhere around 90 degrees away from to the stationary ring 500, although a wide range of angles would be acceptable.

Referring now to FIG. 13D, the inner pouch 100 can have a gasket end (the end that the gasket 200 and associated hole are closest to) and can have a non-gasket end or elongated portion 110 that is opposed to the gasket end. The user can feed the non-gasket end, which is the elongated portion 110 of the inner pouch 100, through the central opening 610 in the movable ring 600 appropriately, depending on the actual angular position of the movable ring 600. As an alternative, it is possible that the inner pouch 100 could be placed into movable ring 600 in a direction opposite the just-described direction, involving deformation of the gasket 200 so that gasket 200 can pass through central opening 610 in movable ring 600. After the inner pouch 100 is approximately in place in movable ring 600, the user can press the gasket 200 into its designated seating place (if such is provided) in movable ring 600. As described elsewhere herein, the geometric relation between gasket 200 and features of movable ring 600 can be such that the gasket 200 either is captured in the central opening 610 of movable ring 600 by its neck 182, or maintains a well-defined position in movable ring 600, or is snugly retained in movable ring 600. Then, the user can swing movable ring 600 upward to reach a closed configuration with respect to stationary ring 500, and the latch feature on movable ring 600 can engage with the latch feature on stationary ring 500. Regardless of the details of insertion of inner pouch 100, when the rings 500, 600 are in the eventual closed configuration, the gasket 200 will be trapped between surfaces of stationary ring 500 and surfaces of movable ring 600, and the elongated portion 110 of the inner pouch 100 will extend away from the patient's body.

If the elongated portion 110 of the inner pouch 100 has not already been stowed inside the outer pouch 300, the patient can stow it appropriately. Then, the outer pouch 300 can be closed and the purse handle segments 310A, 310B on the outer pouch 300 can be mated together, closing the outer pouch 300, as illustrated in FIG. 13E.

When it is desired to remove inner pouch 100, the above sequence of steps can generally be reversed. However, there is one possible exception to a precise reversal of steps. Instead of passing the waste-containing inner pouch 100 through the central opening 610 in movable ring 600, it is possible that the gasket 200 may have geometric dimensions and flexibility properties such that it can be bent or squeezed into an out-of-plane shape, such as into a shape that could be described as a potato chip shape, and the gasket 200 could be squeezed or bent into such a shape and could be passed forward through the central opening 610 in the movable ring 600 in order to remove inner pouch 100 from the appliance 10. This is illustrated in FIG. 13F. The inner pouch 100 could then be disposed of by flushing in a toilet.

NUMBERED EMBODIMENTS

Embodiments of the invention can be further described with reference to the following numbered embodiments:

Embodiment A1: An ostomy system, comprising:
an inner pouch, said inner pouch comprising a film material defining an interior volume and comprising a sealing member, different from said film material in either its material composition or its thickness dimension or both, said sealing member being connected to or integral with said film material, said sealing member having a hole therethrough connecting with said interior volume, said inner pouch being suitable to receive waste matter from said patient;

a stationary ring; and a movable ring hingedly connected to said stationary ring, said movable ring being movable between a closed configuration and an open configuration, wherein in said closed configuration said movable ring and said stationary ring cooperate suitably to grasp said sealing member between said movable ring and said stationary ring suitably to form a desired seal, without grasping said film material between said movable ring and said stationary ring in the absence of said sealing member.

Embodiment A2: The system of Embodiment A1, wherein said sealing member is an O-ring.

Embodiment A3: The system of Embodiment A1, wherein said sealing member is a gasket that has a largest enveloping shape and is generally of uniform thickness in a direction perpendicular to said largest enveloping shape.

Embodiment A4: The system of Embodiment A3, wherein said gasket, in an undeformed condition, is substantially flat and has an annular shape.

Embodiment A5: The system of Embodiment A3, wherein said gasket, in an undeformed condition, is substantially flat, having a flat surface that is parallel to another opposed flat surface of said gasket.

Embodiment A6: The system of Embodiment A3, wherein said gasket, in an undeformed condition, has an inner radius and wherein said gasket and said film material are connected to each other at said inner radius of said gasket.

Embodiment A7: The system of Embodiment A3, wherein said gasket, in an undeformed condition, has a flat surface and wherein said gasket and said film material are connected to each other at a portion of said flat surface of said gasket, but not all of said flat surface of said gasket.

Embodiment A8: The system of Embodiment A3, wherein said gasket, in an undeformed condition, has a flat surface and wherein said gasket and said film material are connected to each other at an entirety of one flat surface of said gasket.

Embodiment A9: The system of Embodiment A3, wherein said film material is connected to said gasket at a side of said gasket that faces toward said movable ring.

Embodiment A10: The system of Embodiment A3, wherein said film material is connected to said gasket at a side of said gasket that faces away from said movable ring.

Embodiment A11: The system of Embodiment A3, wherein said gasket comprises a porous material and an interpenetrating material that partially interpenetrates said porous material, and said film material is connected to said interpenetrating material.

Embodiment A12: The system of Embodiment A3, wherein when said movable ring is in said open configuration and said inner pouch is installed in said movable ring, a joint between said film material and said gasket is at a radius smaller than an inner radius of said lip, and said gasket is on one side of said movable ring and said interior volume of said inner pouch is on an opposite side of said movable ring, whereby said inner pouch is at least somewhat constrained against some degrees of motion with respect to said movable ring.

Embodiment A13: The system of Embodiment A3, wherein said movable ring comprises a gasket-locating feature suitable to locate said gasket in a radial direction with respect to said movable ring when said movable ring is in said open configuration.

Embodiment A14: The system of Embodiment A3, wherein said movable ring comprises a gasket-retaining feature suitable to retain said gasket with respect to said movable ring when said system is in said open configuration such that if said gasket is in said gasket-retaining feature in an orientation such that gravity would urge said gasket out of said gasket-retaining feature, said gasket in a dry condition experiencing the weight of said gasket does not fall out of said gasket-retaining feature.

Embodiment A15: The system of Embodiment A14, wherein said gasket-retaining feature of said movable ring is dimensioned such as to create a frictional fit between an outside surface of said gasket and an inside surface of said gasket-retaining feature.

Embodiment A16: The system of Embodiment A15, wherein said gasket has an exterior that is circular and said frictional fit is against an entirety of said circular exterior of said gasket.

Embodiment A17: The system of Embodiment A14, wherein said gasket-retaining feature comprises discrete features that contact an outside surface of said gasket.

Embodiment A18: The system of Embodiment A14, wherein said gasket-retaining feature contacts an outside surface of said gasket around substantially an entire perimeter of said gasket.

Embodiment A19: The system of Embodiment A1, wherein said seal is continuous around a circumference of said sealing member.

Embodiment A20: The system of Embodiment A1, wherein said seal is intermittent around a circumference of said sealing member.

Embodiment A21: The system of Embodiment A1, wherein said movable ring comprises a circumferential ring structure that is continuous around a circumference of said movable ring and comprises a lip connected to said circumferential ring structure, said lip being more flexible in bending than said circumferential ring structure, said bending being in a plane that contains a longitudinal axis of said movable ring, said lip being configured to contact said sealing member when said system is in said closed configuration.

Embodiment A22: The system of Embodiment A1, wherein said lip extends entirely around a circumference of said movable ring.

Embodiment A23: The system of Embodiment A1, wherein said lip occupies at least a majority of a circumference of said movable ring.

Embodiment A24: The system of Embodiment A3, wherein said movable ring comprises a gasket-locating wall and said gasket-locating wall contacts said gasket continuously around a perimeter of said gasket.

Embodiment A25: The system of Embodiment A3, wherein said movable ring comprises a gasket-locating wall and said gasket-locating wall contacts said gasket intermittently around a perimeter of said gasket.

Embodiment A26: The system of Embodiment A3, wherein said movable ring comprises a gasket-locating wall and wherein in said open configuration, said gasket-locating wall of said movable ring engages an entire thickness of said gasket.

Embodiment A27: The system of Embodiment A3, wherein said movable ring comprises a gasket-locating wall and wherein in said open configuration, said gasket-locating wall of said movable ring engages a portion of a thickness of said gasket.

Embodiment A28: The system of Embodiment A3, wherein said movable ring comprises a gasket-locating wall and said stationary ring contains a groove or recess suitable to receive said gasket-locating wall of said movable ring.

Embodiment A29: The system of Embodiment A1, wherein a seating surface on said stationary ring is flat.

Embodiment A30: The system of Embodiment A1, wherein a seating surface on said stationary ring has one or more bumps that extend continuously around a perimeter of said stationary ring.

Embodiment A31: The system of Embodiment A3, wherein a seating surface on said stationary ring has one or more bumps whose radial locations overlap with radial location(s) where said lip contacts said gasket.

Embodiment A32: The system of Embodiment A1, wherein said system provides a sensory indication of when said movable ring becomes latched to said stationary ring.

Embodiment A33: The system of Embodiment A1, wherein said movable ring and said stationary ring are hingedly connected to each other by a hinge selected from the group consisting of: a pinned hinge; a living hinge; a welded-together hinge; a snap-together hinge; a swaged strap; a snap-together strap; other forms of strap; and a lanyard.

Embodiment A34: The system of Embodiment A1, further comprising a latch between said movable ring and said stationary ring.

Embodiment A35: The system of Embodiment A1, further comprising an outer pouch that generally surrounds said inner pouch.

Embodiment A36: The system of Embodiment A3, wherein in said closed configuration, surfaces of said movable ring and of said stationary ring that are in contact with opposed sides of said gasket include combinations of complementary convex and concave surfaces, or corrugations.

Embodiment B1: An ostomy system, comprising:
an appliance that is suitable to attach or adhere to a body of an ostomy patient;
an inner pouch assembly, disposed within or connected to said appliance, comprising an inner pouch, said inner pouch being suitable to receive waste matter from said patient and contain said waste matter within said inner pouch,
wherein said appliance comprises a stationary ring and a movable ring, said stationary ring and said movable ring being hingedly connected to each other, said movable ring being movable between a closed configuration and an open configuration,
wherein said movable ring comprises a ring structure that extends generally around a perimeter of said movable ring and comprises a deformable lip connected to or integral with said ring structure,
wherein said lip and said movable ring and said stationary ring and said inner pouch assembly are disposed relative to each other such that when said movable ring and said stationary ring are in said closed configuration, a portion of said inner pouch assembly is squeezed between said lip and said stationary ring so as to create a desired seal involving said inner pouch assembly.

Embodiment B2: The system of Embodiment B1, wherein, for bending that occurs in a plane that contains a longitudinal axis of said movable ring, said lip is more flexible than said ring structure.

Embodiment B3: The system of Embodiment B1,
wherein said inner pouch assembly comprises a flexible film material portion,
wherein said inner pouch assembly comprises a gasket, said gasket being generally planar and extending around an entire perimeter and defining a gasket hole therethrough,
wherein said gasket is connected to said flexible film material portion and said gasket hole is an entrance to an interior volume of said inner pouch, wherein said lip presses on said gasket.

Embodiment B4: The system of Embodiment B1, wherein said lip is continuous around a circumference of said movable ring.

Embodiment B5: The system of Embodiment B1, wherein said lip has at least one interruption whose circumferential extent is less than a thickness of said gasket.

Embodiment B6: The system of Embodiment B1, wherein said gasket has an interruption or feature suitable to allow passage of gas therethrough.

Embodiment B7: The system of Embodiment B1, wherein in said closed configuration in an absence of deformation of said lip, there would be an interference between said gasket and said lip, and wherein a majority of deformation toward resolving said interference comes from deformation of said lip.

Embodiment B8: The system of Embodiment B1, wherein said lip deflects by at least one-quarter of a thickness of said gasket when said appliance is in said closed configuration.

Embodiment B9: The system of Embodiment B8, wherein said deflection can be accomplished by a force that can be comfortably exerted with the fingers of one hand.

Embodiment B10: The system of Embodiment B1, wherein said lip is tapered along a direction going from an attachment point of said lip to said ring structure of said movable ring, to an end of said lip that contacts said gasket.

Embodiment B11: The system of Embodiment B1, wherein said lip is curved along a direction going from a meeting point of said lip to said movable ring, to an end of said lip that contacts said gasket.

Embodiment B12: The system of Embodiment B1, wherein said lip comprises, on its end, a bead, said bead being larger than a thickness of said lip immediately adjacent to said bead.

Embodiment B13: The system of Embodiment B1, wherein said stationary ring comprises a bump that is generally opposed to said lip and is continuous around a circumference of said stationary ring.

Embodiment B14: The system of Embodiment B1, wherein said movable ring and said stationary ring comprise complementary convex and concave surfaces, which may extend completely around respective circumferences of said rings, one on said movable ring and the other on said stationary ring, said surfaces being opposed to and complementary to each other.

Embodiment B15: The system of Embodiment B14, wherein said movable ring and said stationary ring comprise a plurality, proceeding in a radial direction, of said complementary convex and concave surfaces.

Embodiment C1: 51. An ostomy system, comprising:
an appliance that is suitable to attach or adhere to a body of an ostomy patient;
an inner pouch assembly, disposed within or connected to said appliance, comprising an inner pouch, said inner pouch being suitable to receive waste matter from said patient and contain said waste matter within said inner pouch, wherein said appliance comprises a stationary ring and a movable ring, said stationary ring and said movable ring being hingedly connected to each other, said movable ring being movable between a closed configuration and an open configuration, wherein said stationary ring comprises a ring structure that extends generally around a perimeter of said stationary ring and comprises a deformable lip connected to or integral with said ring structure, wherein said lip and said movable ring and said stationary ring and said inner pouch assembly are disposed relative to each other such that when said movable ring and said stationary ring are in said closed configuration, a portion of said inner pouch assembly is squeezed between said lip and said movable ring so as to create a desired seal involving said inner pouch assembly.

Embodiment C2: The system of Embodiment C1, wherein said lip comprises, on its end, a bead, said bead being larger than a thickness of said lip immediately adjacent to said bead.

Embodiment D1: An ostomy system, comprising:
an appliance that is suitable to attach or adhere to a body of an ostomy patient;
an inner pouch within said appliance, said inner pouch being suitable to receive waste matter from said patient and contain said waste matter within said inner pouch,
wherein said inner pouch comprises an inner pouch proximal layer and an inner pouch distal layer joined to each other,
wherein said inner pouch comprises a gasket connected to said inner pouch proximal layer and shares a common hole with said inner pouch proximal layer,
wherein said gasket defines a closed ring shape lying in a plane and said gasket has a bending stiffness for said out-of-plane bending,
wherein, in a dry state, said bending stiffness of said gasket for said out-of-plane bending that is greater than a stiffness of said inner pouch proximal layer,
wherein said gasket, in a dry state, when grasped at an edge in a horizontally cantilevered configuration bearing its own weight, said gasket deflects by less than 10% of a cantilever distance, and
wherein said gasket, after having been immersed in water for at least 5 seconds, when grasped at said edge in said horizontally cantilevered configuration bearing its own weight including weight of any water absorbed into said gasket, deflects by more than 10% of said cantilever distance.

Embodiment D2: The system of Embodiment D1, wherein a cantilever distance is defined by a boundary between said grasped portion of said gasket and said cantilevered portion of said gasket, and said boundary is tangent to an inner circumference of said gasket.

Embodiment D3: The system of Embodiment D1, wherein said gasket comprises a fibrous material.

Embodiment D4: The system of Embodiment D1, wherein said gasket comprises paper having a density of between 0.015 lb/inch^3 and 0.035 lb/inch^3.

Embodiment D5: The system of Embodiment D1, wherein said gasket comprises paper having a thickness of between 0.25 mm and 1 mm.

Embodiment D6: The system of Embodiment D1, wherein said gasket comprises paper suitable for water color painting.

Embodiment D7: The system of Embodiment D1, wherein said gasket comprises a paper-like or fibrous material that is partially interpenetrated by a polymer, and wherein said inner pouch is joined to said interpenetrated polymer.

Embodiment D8: The system of Embodiment D7, wherein said partially interpenetrated condition is interpenetrated to less than all void volume of said material, or is interpenetrated to less than an entire thickness of said gasket with one surface of said gasket being free of said polymer.

Embodiment D9: The system of Embodiment D1, wherein said gasket and said inner pouch are joined by an adhesive.

Embodiment D10: The system of Embodiment D1, wherein said gasket and said inner pouch are joined by a melting process or a solvent process.

Embodiment D11: The system of Embodiment D1, wherein said gasket comprises an open-celled foam.

Embodiment D12: The system of Embodiment D1, wherein said gasket comprises at least one groove in its surface, said groove extending from an inner perimeter of said gasket to an outer perimeter of said gasket.

Embodiment E1: An ostomy system, comprising:
an appliance that is suitable to attach or adhere to a body of an ostomy patient, said appliance comprising an outer pouch and an inner pouch;
wherein said inner pouch is disposed suitably to receive waste matter from said patient and contain said waste matter within said inner pouch,
wherein said outer pouch generally surrounds said inner pouch,
wherein said outer pouch comprises an outer pouch proximal layer and an outer pouch distal layer opposed to said outer pouch proximal layer, and wherein said outer pouch distal layer comprises a deformable surface that is larger than a corresponding surface on said outer pouch proximal layer,
wherein said deformable surface is flexible and deformable between a compact position and an extended position, and when in said extended position has a surface length that is greater than a surface length of a corresponding region on said outer pouch proximal layer.

Embodiment E2: The system of Embodiment E1, wherein said deformable surface comprises a blister.

Embodiment E3: The system of Embodiment E2, wherein a lengthwise extent of said blister is less than 90% of an overall lengthwise extent of said outer pouch, and a width extent of said blister is less than 90% of an overall width of said outer pouch, and a depth of said blister is less than 2 inches.

Embodiment E4: The system of Embodiment E2, wherein said blister has a bending stiffness that is between 50% and 200% of a bending stiffness of said outer pouch proximal layer.

Embodiment E5: The system of Embodiment E1, wherein said deformable surface comprises a pleat having at least one concave fold and at least one convex fold.

Embodiment E6: The system of Embodiment E5, wherein said pleat has a transverse larger dimension that is from 0.2 to 0.6 times a width of said outer pouch, and said pleat has a transverse smaller dimension that is from 0.1 to 0.4 times said width of said outer pouch.

Embodiment F1: 71. An ostomy system, comprising:
an appliance that is suitable to attach or adhere to a body of an ostomy patient, said appliance comprising an outer pouch and an inner pouch said inner pouch being generally surrounded by said outer pouch;

wherein said inner pouch is disposed suitably to receive waste matter from said patient and contain said waste matter within said inner pouch, wherein said outer pouch comprises a storage region comprising an additional layer connected to said outer pouch, said storage region being dimensioned appropriately to contain at least one unused inner pouch.

Embodiment F2: The ostomy system of Embodiment F1, wherein said storage region further comprises a cover flap suitable to overlap said additional layer.

Embodiment F3: The ostomy system of Embodiment F1, wherein said storage region is located on a same side of said appliance as is configured to be attached to said body of said patient.

Embodiment G1: An ostomy system, comprising:

an inner pouch, said inner pouch comprising a film material defining an interior volume and comprising a sealing member, different from said film material, connected to or integral with said film material, said film material and said sealing member having a common hole therethrough suitable to receive waste matter from said patient such that said waste matter can be contained within said interior volume;

a stationary ring; and a movable ring hingedly connected to said stationary ring, said movable ring being movable between a closed configuration and an open configuration, wherein in said closed configuration said movable ring and said stationary ring cooperate suitably to grasp said sealing member between said movable ring and said stationary ring suitably to form a desired seal, wherein in said closed configuration said movable ring and said stationary ring engage each other with a latch, wherein said stationary ring and said movable ring comprise a material having a Shore durometer property of Shore A50 or softer, and wherein said latch extends around at least 270 degrees of circumference of said stationary ring and said movable ring.

Embodiment G2: The system of Embodiment G1, wherein said stationary ring or said movable ring comprise a material having a Shore durometer property of Shore A40 or softer.

Embodiment G3: The system of Embodiment G1, wherein said stationary ring or said movable ring comprise a material having a Shore durometer property of Shore A30 or softer.

Embodiment H1: An ostomy system, said system comprising:

a wafer assembly attachable to a patient's skin, said wafer assembly comprising a wafer coupling; and an appliance comprising an appliance coupling engageable with said wafer coupling, said appliance further comprising a gripping mechanism that, while said appliance coupling is engaged with said wafer coupling, has a closed configuration in which said appliance grips an inner pouch and an open configuration in which said inner pouch is not gripped.

Embodiment H2: The system of Embodiment H1, wherein said gripping mechanism comprises a stationary ring and a movable ring engageable with each other.

Embodiment H3: The system of Embodiment H1, wherein said gripping mechanism comprises a stationary ring and a movable ring that are engageable with each other and are hingedly connected to each other.

Embodiment H4: The system of Embodiment H1, wherein said appliance coupling has a groove and said wafer coupling fits resiliently within said groove.

Embodiment H5: The system of Embodiment H1, wherein said wafer coupling has a groove and said appliance coupling fits resiliently within said groove.

Embodiment H6: The system of Embodiment H1, wherein said appliance coupling has a groove, and wherein said wafer coupling has a wall and a lip attached to or continuous with said wall, and said lip in an undeformed condition has a curved path.

Embodiment H7: The system of Embodiment H1, wherein said appliance coupling has a groove, and wherein said wafer coupling has a wall and a lip attached to or continuous with said wall, and said lip is tapered.

Embodiment I1: A method of installing an inner pouch in an ostomy appliance, said method comprising:

providing an appliance comprising an outer pouch, a stationary ring and a movable ring hingedly connected to said stationary ring, said stationary ring and said movable ring having respective central openings therethrough, said movable ring being movable between a closed configuration and an open configuration, said outer pouch having a reclosable opening;

providing an inner pouch, said inner pouch comprising a sealing member and film material connected to or integral with said sealing member, at least a portion of said inner pouch being suitable to pass through said central opening of said movable ring;

with said movable ring being in said open configuration, passing a portion of said inner pouch through said central opening in said movable ring;

moving said movable ring to said closed configuration such that said sealing member is grasped between said movable ring and said stationary ring; and closing said reclosable opening in said outer pouch.

Embodiment I2: The method of Embodiment I2, wherein said sealing member comprises a gasket.

Further Remarks

The stationary ring 500 and the movable ring 600 may be made of a polymeric material and may be made, for example by injection molding. Other manufacturing methods, such as additive manufacturing, are also possible.

The term "sealing member" is intended to encompass gaskets, which may be flat; O-rings; and generally any other geometry of deformable member, different in some way from the film material of which the inner pouch 100 is made, that can be grasped between stationary ring 500 and movable ring 600 to create a seal. The term "hingedly" is intended to include components that provide for geometric rotation about an axis, but more broadly, it is intended also to include components that, in addition to providing single-axis rotation, also allow some other forms of motion, such as translation or rotation about other axes.

Discussion herein has illustrated embodiments in which, when the assembly is in its closed configuration, the gasket 200 is substantially flat and rests against a seating surface, in stationary ring 500, that also is flat. There may be localized deformation of gasket 200 where lip 650 presses against it, but generally gasket 200 remains flat at least to the extent that its shape is defined by the flat seating surface. It is also possible to consider complementary convex and concave features, which may cooperate with each other so as to deform gasket 200 when gasket 200 is clamped between rings 500, 600 so as to create or enhance a seal. These could resemble corrugations.

In general, localized features that have been described, such as sealing surfaces, gasket-locating features, gasket-retaining features, lips, corrugations, beads, bumps, etc. could be on either the movable ring or the stationary ring, as desired.

Dimensions and numerical values discussed herein are not intended to be limiting, but rather merely exemplary.

All cited references are incorporated by reference herein in their entirety. Embodiments of the invention can also include variations and combinations of what has been disclosed, in any combination that is physically possible. In method claims, the order of performing steps could be any order that is physically possible. Although embodiments of the invention have been disclosed, it is not desired to be limited thereby. Rather it is desired that the scope be limited only by the attached claims.

We claim:

1. An ostomy system, comprising:
   an inner pouch, said inner pouch comprising:
      an inner pouch proximal layer and an inner pouch distal layer, each made of a film material and joined together at their peripheries to define an interior volume,
      a first hole in the inner pouch proximal layer; and
      a sealing member different from said film material in either its material composition or its thickness dimension or both, said sealing member being connected to or integral with said film material and said sealing member having a second hole therethrough that substantially aligns with the first hole of the inner pouch proximal layer, such that the sealing member and the inner pouch proximal layer are attached to each other to form distal and/or proximal attached portions adjacent to inner edges of their respective second and first holes that are connecting with said interior volume,
   said inner pouch configured to receive waste matter from said patient when sealingly attached around a stoma of the patient;
   a stationary ring; and
   a movable ring hingedly connected to said stationary ring, said movable ring being movable between a closed configuration and an open configuration,
   wherein in said closed configuration said movable ring and said stationary ring cooperate suitably to grasp said distal and/or proximal attached portions of said inner pouch proximal layer and said sealing member between said movable ring and said stationary ring suitably to form a seal; such that there is no grasping of said film material between said movable ring and said stationary ring without said sealing member also being grasped at the same place between said movable ring and said stationary ring.

2. The system of claim 1, wherein said sealing member further comprises a gasket that is generally of uniform thickness in a direction perpendicular to a plane of said gasket.

3. The system of claim 2, wherein said gasket, in an undeformed condition, has an inner circumference and wherein said gasket and said film material are connected to each other at said inner circumference of said gasket, or at a portion of a flat surface of said gasket, or at an entirety of said flat surface of said gasket, or combinations thereof.

4. The system of claim 2, wherein when said movable ring is in said open configuration, said inner pouch is able to be placed in said movable ring such that at least a portion of a joint or connection between said film material and said gasket is at a radius smaller than an inner radius of said movable ring, and when said gasket is on one side of said movable ring and said interior volume of said inner pouch is on an opposite side of said movable ring, said inner pouch is at least somewhat constrained against some degrees of motion with respect to said movable ring.

5. The system of claim 1, further comprising a latch suitable to latch said movable ring and said stationary ring to each other.

6. The system of claim 5, wherein said latch provides a sensory indication of when said movable ring and said stationary ring become latched together.

* * * * *